(12) United States Patent
Luecking et al.

(10) Patent No.: US 7,943,629 B2
(45) Date of Patent: May 17, 2011

(54) SULPHIMIDES AS PROTEIN KINASE INHIBITORS

(75) Inventors: Ulrich Luecking, Berlin (DE); Duy Nguyen, Berlin (DE); Arne von Bonin, Glienicke-Nordbahn (DE); Oliver von Ahsen, Berlin (DE); Gerhard Siemeister, Berlin (DE); Rolf Jautelat, Berlin (DE); Wolf-Dietrich Doecke, Berlin (DE)

(73) Assignee: Bayer Schering Pharma AG, Berlin (DE)

( * ) Notice: Subject to any disclaimer, the term of this patent is extended or adjusted under 35 U.S.C. 154(b) by 1001 days.

(21) Appl. No.: 11/759,479

(22) Filed: Jun. 7, 2007

(65) Prior Publication Data
US 2008/0058358 A1  Mar. 6, 2008

Related U.S. Application Data

(60) Provisional application No. 60/814,525, filed on Jun. 19, 2006.

(30) Foreign Application Priority Data

Jun. 8, 2006  (DE) .......................... 10 2006 027 156

(51) Int. Cl.
C07D 239/48 (2006.01)
A61K 31/506 (2006.01)
(52) U.S. Cl. ....................................... 514/275; 544/323
(58) Field of Classification Search ................. 544/323; 514/275
See application file for complete search history.

(56) References Cited

U.S. PATENT DOCUMENTS
2005/0176743 A1  8/2005 Luecking et al.

FOREIGN PATENT DOCUMENTS
WO  WO 2005/037800 A  4/2005

OTHER PUBLICATIONS

Simone, Oncology: Introduction, Cecil Textbook of Medicine, 20th Edition, vol. 1, pp. 1004-1010, 1996.*
Cohen et al., Current Opinion in Chemical Biology, 3, 459-465, 1999.*
Dermer et al., Bio/Technology, 1994, 12:320.*
Freshney et al., Culture of Animal Cells, A Manual of Basic Technique, Alan R. Liss, Inc., 1983, New York, pp. 1-6.*
Golub et al., Science, 266, 531-537, 1993.*
Mass, R.D., Int. J. Radiation Oncology Bio Phys. vol. 58(3):932-940, 2004.*
Fabbro et al., Pharmacology & Therapeutics 93 (2002), pp. 79-98.*
Powell et al., British Journal of Dermatology, 141:802-810, 1999.*
Tohru Ueda, et al.; "Nucleosides XVII. Pyrimidinyl Amino Acids"; J. Med Chem.; 1963; Bd. 6; pp. 697-700.
Simon F. Campbell, et al.; "2, 4-Diamino-6,7,-dimethoxyquinazolines.3. 2-(4-heterocyclylpiperazin-1-yl) derivatives . . ." J. Med. Chem.; 1987; Bd. 30; pp. 1794-1798.
Polina I. Svirskaya, et al.; "Fluorinated heterocyclic compounds. 2. 2, 4-difluoro and 4-amino-2-fluoropyrimidines, nucleoside base analogs"; J. Heterocycl. Chem.; 1985; pp. 149-153.
Giorgio Caravatti, et al.; "Structure based design of a non-peptidic antagonist of the SH2 domain of GRB2"; Bioorg. Med. Chem. Lett.; 1999; pp. 1973-1978; Bd. 9.
G.B. Barlin; "Kinetics of reactions in heterocycles"; J. Chem. Soc. (B); 1967; pp. 954-958.
Kondratenko, et al.; "S-trifluoromethyl-S-aryl-N-trifluoromethylsulfonylsulfimides"; Zhurnal Organicheskoi Khimii; 1984; pp. 2599-2604; Bd. 20, Nr. 12; Chemical Abstracts Service, Database accession No. 102:220513.
Kenneth K. Andersen, et al.; "Antimalarial sulfilimines and sulfoximines related to diaminodiphenyl sulfoxide and sulfone"; J. Med. Chem.; 1970; pp. 759-760; Bd. 13, Nr. 4.

* cited by examiner

Primary Examiner — Deepak Rao
(74) Attorney, Agent, or Firm — Millen, White, Zelano & Branigan, P.C.

(57) ABSTRACT

The invention relates to sulphimides as protein kinase inhibitors of the general formula I

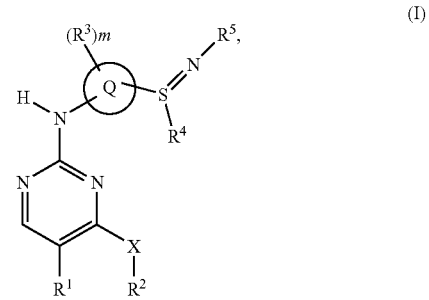

24 Claims, No Drawings

SULPHIMIDES AS PROTEIN KINASE INHIBITORS

This application claims the benefit of the filing date of U.S. Provisional Application Ser. No. 60/814,525 filed Jun. 19, 2006.

The invention relates to sulphimides as protein kinase inhibitors.

Many biological processes such as, for example, DNA replication, energy metabolism, cell growth or cell differentiation in eukaryotic cells are regulated by reversible phosphorylation of proteins. The degree of phosphorylation of a protein has an influence inter alia on the function, localization or stability of proteins. The enzyme families of protein kinases and protein phosphatases are responsible respectively for the phosphorylation and dephosphorylation of proteins.

It is hoped, through inhibition of specific protein kinases or protein phosphatases, to be able to intervene in biological processes in such a way that causal or symptomatic treatment of diseases of the human or animal body is possible.

Protein kinases are of particular interest in this connection, inhibition thereof making the treatment of cancer possible.

The following protein kinase families come under consideration for example as targets for inhibitory molecules:

a) Cell cycle kinases, i.e. kinases whose activity control the progression of the cycle of cell division. Cell cycle kinases include substantially the cyclin-dependent kinases (cdk), the polo-like kinases (Plk), and the Aurora kinases.

b) Receptor tyrosine kinases which regulate angiogenesis (angiogenic receptor tyrosine kinases), such as, for example, the receptor tyrosine kinases which are involved in the vascular endothelial growth factor (VEGF)/VEGF receptor system, fibroblast growth factor (FGF)/FGF receptor system, in the Eph ligand/EphB4 system, and in the Tie ligand/Tie system, c) Receptor tyrosine kinases whose activity contributes to the proliferation of cells (proliferative receptor tyrosine kinases), such as, for example, receptor tyrosine kinases which are involved in the platelet-derived growth factor (PDGF) ligand/PDGF receptor system, c-kit ligand/c-kit receptor system and in the FMS-like tyrosine kinase 3 (Flt-3) ligand/Flt-3 system, d) checkpoint kinases which monitor the ordered progression of cell division, such as, for example, ATM and ATR, Chk1 and Chk2, Mps1, Bub1 and BubR1, e) kinases whose activity protect the cell from apoptosis (anti-apoptotic kinases, kinases in so-called survival pathways, anti-apoptotic kinases), such as, for example, Akt/PKB, PDK1, IkappaB kinase (IKK), PIM1, and integrin-linked kinase (ILK), f) kinases which are necessary for the migration of tumour cells (migratory kinases), such as, for example, focal adhesion kinase (FAK) and Rho kinase (ROCK).

Inhibition of one or more of these protein kinases opens up the possibility of inhibiting tumour growth.

In this connection there is a need in particular for structures which, besides inhibiting cell cycle kinases, inhibit tumour growth through the inhibition of one or more further kinases (multi-target tumour growth inhibitors=MTGI). It is particularly preferred to inhibit in addition receptor tyrosine kinases which regulate angiogenesis.

The structures of the following patent applications form the structurally close prior art:

WO 2002/096888 discloses anilinopyrimidine derivatives as inhibitors of cyclin-dependent kinases. Sulphimide substitutents are not disclosed for the aniline.

WO 2004/026881 discloses macrocyclic anilinopyrimidine derivatives as inhibitors of cyclin-dependent kinases. A possible sulphimide substitutent for the aniline is not disclosed.

WO 2005/037800 discloses open anilinopyrimidine derivatives as inhibitors of cyclin-dependent kinases. Sulphimide substitutents are not disclosed for the aniline.

It is common to all these structures of the prior art that they inhibit cell cycle kinases.

Starting from this prior art, it is the object of the present invention to provide a novel class of protein kinase inhibitors.

In particular, the object of the present invention is to provide inhibitors of protein kinases by which tumour growth can be inhibited.

There is a need in particular for a novel structural class which, besides cell cycle kinases, also inhibits receptor tyrosine kinases which inhibit angiogenesis.

The object of the present application is achieved by compounds of the general formula (I),

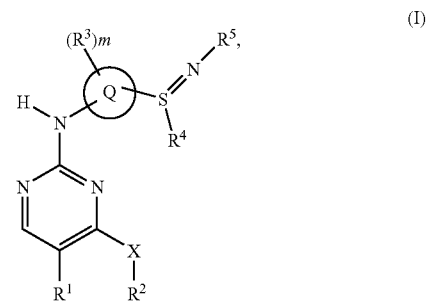

in which
$R^1$ is
(i) hydrogen, halogen, cyano, nitro, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, —$CF_3$ or —$OCF_3$, or
(ii) a $C_1$-$C_6$-alkyl, $C_2$-$C_6$-alkenyl, $C_1$-$C_6$-alkoxy or $C_2$-$C_6$-alkynyl radical which is optionally substituted one or more times, identically or differently, by hydroxy, —$NR^8R^9$, —$NR^7$—C(O)—$R^{12}$, —$NR^7$—C(O)—$OR^{12}$, $NR^7$—C(O)—$NR^8R^9$, —$NR^7$—$SO_2$—$R^{12}$, cyano, halogen, $C_1$-$C_6$-alkoxy, —$CF_3$ and/or —$OCF_3$, or
(iii) a phenyl or monocyclic heteroaryl ring which is optionally substituted one or more times, identically or differently, by hydroxy, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, cyano, halogen, —$CF_3$, $C_1$-$C_6$-alkoxy, —$OCF_3$ and/or $C_1$-$C_6$-alkyl, $R^2$ is
(i) hydrogen or
(ii) a $C_1$-$C_{10}$-alkyl, $C_2$-$C_{10}$-alkenyl or $C_2$-$C_{10}$-alkynyl radical, a $C_3$-$C_7$-cycloalkyl, phenyl or naphthyl ring, a heterocyclyl ring having 3 to 8 ring atoms or a mono- or bicyclic heteroaryl ring,
in each case optionally substituted one or more times, identically or differently, by
a) halogen, hydroxy, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, cyano, —C(O)$R^6$, —O(CO)—$R^{12}$, —$SO_2NR^8R^9$, —$SO_2$—$R^{12}$, —S(O)($NR^8$)$R^{12}$—(N)S(O)$R^{13}R^{14}$, —$CF_3$, —$OCF_3$, —N[(CO)—($C_1$-$C_6$-alkyl)]$_2$ and/or b) $C_1$-$C_6$-alkoxy, $C_1$-$C_6$-alkyl, $C_2$-$C_6$-alkenyl, $C_2$-$C_6$-alkynyl, $C_3$-$C_8$-cycloalkyl, phenyl, naphthyl, heterocyclyl having 3 to 8 ring atoms and/or a monocyclic or bicyclic heteroaryl, in each case optionally themselves substituted one or more times, identically or differently, by halogen, hydroxy, a $C_1$-$C_6$-alkyl, $C_1$-$C_6$-alkoxy,
—$NR^8R^9$, —$C(O)OR^{16}$, —$SO_2NR^8R^9$, —$CF_3$ or —$OCF_3$, $R^3$ is
(i) hydroxy, halogen, cyano, nitro, —$CF_3$, —$OCF_3$, —$C(O)NR^8R^9$, —$C(S)NR^8R^9$, —$NR^8R^9$, —$NR^7$—$C(O)$—$R^{12}$, —$NR^7$—$C(O)$—$OR^{12}$, —$NR^7$—$C(O)$—$NR^8R^9$, —$NR^7$—$SO_2$—$R^{12}$, and/or
(ii) a $C_1$-$C_6$-alkyl and/or $C_1$-$C_6$-alkoxy radical which is optionally substituted one or more times, identically or differently, by halogen, hydroxy, $C_1$-$C_6$-alkoxy, —$CF_3$, —$OCF_3$ or —$NR^8R^9$, and/or
(iii) a $C_3$-$C_7$-cycloalkyl ring which is optionally substituted one or more times, identically or differently, by halogen, hydroxy, $C_1$-$C_6$-alkoxy, —$CF_3$, —$OCF_3$, —$NR^8R^9$ and/or $C_1$-$C_6$-alkyl, m is 0-4, $R^4$ is a $C_1$-$C_6$-alkyl, $C_2$-$C_6$-alkenyl, radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy, —$OCF_3$ and/or $C_1$-$C_6$-alkyl, or $R^3$ and $R^4$ together form a 5 to 7-membered ring which is fused to Q and which is optionally substituted one or more times, identically or differently, by hydroxy, $C_1$-$C_6$-alkyl, $C_1$-$C_6$-alkoxy, halogen or —$NR^8R^9$, and optionally comprises in addition to the double bond from Q a further double bond if the ring is 5-membered, $R^5$ is
—$SO_2$—$(CH_2)_n$—$R^{12}$ where n is 0 or 1, —$C(O)R^{12}$, —$C(O)OR^{12}$, —$C(O)NR^8R^9$, —$C(S)OR^{12}$, —$C(S)NR^8R^9$ or —$R^{12}$,
or
$R^4$ and $R^5$ together form a 5 to 7-membered ring of the formula

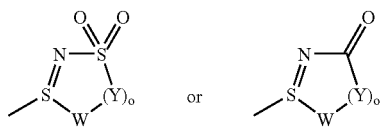

in which
W and Y are each independently of one another a —$CH_2$— group which is optionally substituted one or more times, identically or differently, by hydroxy, $C_1$-$C_6$-alkyl, $C_1$-$C_6$-alkoxy or —$NR^8R^9$, where the $C_1$-$C_6$-alkyl and/or $C_1$-$C_6$-alkoxy substitutent is optionally itself substituted one or more times, identically or differently, by hydroxy, $C_1$-$C_6$-alkoxy or —$NR^8R^9$, and/or optionally comprises in addition to the imide double bond 1 or 2 further double bonds,
and
in which
o is 1-3
X is —O—, —S— or —$NR^{15}$—, where
$R^{15}$ is
(i) hydrogen or
(ii) a $C_1$-$C_6$-alkyl radical, $C_3$-$C_8$-cycloalkyl or phenyl ring, a heterocyclyl ring having 3 to 8 ring atoms or a monocyclic heteroaryl ring, or
(iii) —$C(O)$—$(C_1$-$C_6)$-alkyl, —$C(O)$-phenyl, or —$C(O)$-benzyl, and (ii) and (iii) are optionally substituted one or more times, identically or differently, by hydroxy, —$NR^{10}R^{11}$, cyano, halogen, —$CF_3$, $C_1$-$C_6$-alkoxy and/or —$OCF_3$,
or
if X is —$NR^{15}$—, alternatively
X, $R^{15}$ and $R^2$ together form a 3 to 8 membered ring which optionally comprises in addition to the nitrogen atom one or more further heteroatoms, is optionally substituted one or more times, identically or differently, by hydroxy, $C_1$-$C_6$-alkyl, $C_1$-$C_6$-alkoxy, —$C(O)R^{12}$, —$SO_2R^{12}$, halogen or the group —$NR^8R^9$, optionally comprises 1 to 3 double bonds, and/or is optionally interrupted by one or more —$C(O)$— groups, Q is a phenyl, naphthyl or a monocyclic or bicyclic heteroaryl ring, $R^6$ is
(i) hydrogen or hydroxy, or
(ii) a $C_1$-$C_6$-alkyl, $C_3$-$C_6$-alkenyl, $C_3$-$C_6$-alkynyl or $C_1$-$C_6$-alkoxy radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy and/or —$OCF_3$, $R^7$ is hydrogen or a $C_1$-$C_6$-alkyl radical, $R^8$ and $R^9$ are independently of one another
(i) hydrogen and/or
(ii) a $C_1$-$C_6$-alkyl radical, $C_2$-$C_6$-alkenyl radical, $C_3$-$C_8$-cycloalkyl and/or phenyl ring, a heterocyclyl ring having 3 to 8 ring atoms and/or a monocyclic heteroaryl ring, optionally substituted one or more times, identically or differently, by hydroxy, —$NR^{10}R^{11}$, cyano, halogen, —$CF_3$, $C_1$-$C_6$-alkoxy and/or —$OCF_3$,
or $R^8$ and $R^9$ together with the nitrogen atom form a 5- to 7-membered ring which optionally comprises in addition to the nitrogen atom 1 or 2 further heteroatoms, and which may be substituted one or more times, identically or differently, by hydroxy, —$NR^{10}R^{11}$, cyano, halogen, —$CF_3$, $C_1$-$C_6$-alkoxy and/or —$OCF_3$, $R^{10}$ and $R^{11}$ are independently of one another hydrogen or a $C_1$-$C_6$-alkyl radical which is optionally substituted one or more times, identically or differently, by hydroxy, cyano, halogen, —$CF_3$, $C_1$-$C_6$-alkoxy and/or —$OCF_3$, $R^{12}$, $R^{13}$, $R^{14}$ are independently of one another —$CF_3$,
or
a $C_1$-$C_6$-alkyl, $C_2$-$C_6$-alkenyl and/or $C_2$-$C_6$-alkynyl radical, a $C_3$-$C_7$-cycloalkyl or phenyl ring, a heterocyclyl ring having 3 to 8 ring atoms or a monocyclic heteroaryl ring, which are optionally in each case themselves substituted one or more times, identically or differently, by hydroxy, nitro, —$NR^8R^9$, —NH—$C(O)$—$C_1$-$C_6$-alkyl, cyano, halogen, —$CF_3$, $C_1$-$C_6$-alkyl, $C_1$-$C_6$-alkoxy and/or —$OCF_3$, $R^{16}$ is
(i) hydrogen or
(ii) a $C_1$-$C_6$-alkyl, $C_3$-$C_6$-alkenyl, $C_3$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —NR$^8$R$^9$, cyano, halogen, —CF$_3$, C$_1$-C$_6$-alkoxy and/or —OCF$_3$, and the salts, diastereomers and enantiomers thereof.

No prior art document proposes sulphimide substitutents on anilinopyrimidine derivatives which inhibit protein kinases. Nor are sulphimide substitutents disclosed for other structural classes which inhibit protein kinases.

The following definitions underlie the invention:

C$_n$-Alkyl:

Monovalent, straight-chain or branched, saturated hydrocarbon radical having n carbon atoms.

A C$_1$-C$_6$ alkyl radical includes inter alia for example: methyl-, ethyl-, propyl-, butyl-, pentyl-, hexyl-, iso-propyl-, iso-butyl-, sec-butyl-, tert-butyl-, iso-pentyl-, 2-methylbutyl-, 1-methylbutyl-, 1-ethylpropyl-, 1,2-dimethylpropyl-, neo-pentyl-, 1,1-dimethylpropyl-, 4-methylpentyl-, 3-methylpentyl-, 2-methylpentyl-, 1-methylpentyl-, 2-ethylbutyl-, 1-ethylbutyl-, 3,3-dimethylbutyl-, 2,2-dimethylbutyl-, 1,1-dimethylbutyl-, 2,3-dimethylbutyl-, 1,3-dimethylbutyl-1,2-dimethylbutyl-.

A methyl, ethyl, propyl or isopropyl radical is preferred.

C$_n$-Alkenyl:

monovalent, straight-chain or branched hydrocarbon radical having n carbon atoms and at least one double bond.

A C$_2$-C$_{10}$ alkenyl radical includes inter alia for example: vinyl-, allyl-, (E)-2-methylvinyl-, (Z)-2-methylvinyl-, homoallyl-, (E)-but-2-enyl-, (Z)-but-2-enyl-, (E)-but-1-enyl-, (Z)-but-1-enyl-, pent-4-enyl-, (E)-pent-3-enyl-, (Z)-pent-3-enyl-, (E)-pent-2-enyl-, (Z)-pent-2-enyl-, (E)-pent-1-enyl-, (Z)-pent-1-enyl-, hex-5-enyl-, (E)-hex-4-enyl-, (Z)-hex-4-enyl-, (E)-hex-3-enyl-, (Z)-hex-3-enyl-, (E)-hex-2-enyl-, (Z)-hex-2-enyl-, (E)-hex-1-enyl-, (Z)-hex-1-enyl-, isopropenyl-, 2-methylprop-2-enyl-, 1-methylprop-2-enyl-, 2-methylprop-1-enyl-, (E)-1-methylprop-1-enyl-, (Z)-1-methylprop-1-enyl-, 3-methylbut-3-enyl-, 2-methylbut-3-enyl-, 1-methylbut-3-enyl-, 3-methylbut-2-enyl-, (E)-2-methylbut-2-enyl-, (Z)-2-methylbut-2-enyl-, (E)-1-methylbut-2-enyl-, (Z)-1-methylbut-2-enyl-, (E)-3-methylbut-1-enyl-, (Z)-3-methylbut-1-enyl-, (E)-2-methylbut-1-enyl-, (Z)-2-methylbut-1-enyl-, (E)-1-methylbut-1-enyl-, (Z)-1-methylbut-1-enyl-, 1,1-dimethylprop-2-enyl-, 1-ethylprop-1-enyl-, 1-propylvinyl-, 1-isopropylvinyl-, 4-methylpent-4-enyl-, 3-methylpent-4-enyl-, 2-methylpent-4-enyl-, 1-methylpent-4-enyl-, 4-methylpent-3-enyl-, (E)-3-methylpent-3-enyl-, (Z)-3-methylpent-3-enyl-, (E)-2-methylpent-3-enyl-, (Z)-2-methylpent-3-enyl-, (E)-1-methylpent-3-enyl-, (Z)-1-methylpent-3-enyl-, (E)-4-methylpent-2-enyl-, (Z)-4-methylpent-2-enyl-, (E)-3-methylpent-2-enyl-, (Z)-3-methylpent-2-enyl-, (E)-2-methylpent-2-enyl-, (Z)-2-methylpent-2-enyl-, (E)-1-methylpent-2-enyl-, (Z)-1-methylpent-2-enyl-, (E)-4-methylpent-1-enyl-, (Z)-4-methylpent-1-enyl-, (E)-3-methylpent-1-enyl-, (Z)-3-methylpent-1-enyl-, (E)-2-methylpent-1-enyl-, (Z)-2-methylpent-1-enyl-, (E)-1-methylpent-1-enyl-, (Z)-1-methylpent-1-enyl-, 3-ethylbut-3-enyl-, 2-ethylbut-3-enyl-, 1-ethylbut-3-enyl-, (E)-3-ethylbut-2-enyl-, (Z)-3-ethylbut-2-enyl-, (E)-2-ethylbut-2-enyl-, (Z)-2-ethylbut-2-enyl-, (E)-1-ethylbut-2-enyl-, (Z)-1-ethylbut-2-enyl-, (E)-3-ethylbut-1-enyl-, (Z)-3-ethylbut-1-enyl-, 2-ethylbut-1-enyl-, (E)-1-ethylbut-1-enyl-, (Z)-1-ethylbut-1-enyl, 2-propylprop-2-enyl-, 1-propylprop-2-enyl-, 2-isopropylprop-2-enyl-, 1-isopropylprop-2-enyl-, (E)-2-propylprop-1-enyl-, (Z)-2-propylprop-1-enyl-, (E)-1-propylprop-1-enyl-, (Z)-1-propylprop-1-enyl-, (E)-2-isopropylprop-1-enyl-, (Z)-2-isopropylprop-1-enyl-, (E)-1-isopropylprop-1-enyl-, (Z)-1-isopropylprop-1-enyl-, (E)-3,3-dimethylprop-1-enyl-, (Z)-3,3-dimethylprop-1-enyl-, 1-(1,1-dimethylethyl) ethenyl.

A vinyl or allyl radical is preferred.

C$_n$-Alkynyl:

Monovalent, straight-chain or branched hydrocarbon radical having n carbon atoms and at least one triple bond.

A C$_2$-C$_{10}$ alkynyl radical includes inter alia for example: ethynyl-, prop-1-ynyl-, prop-2-ynyl-, but-1-ynyl-, but-2-ynyl-, but-3-ynyl-, pent-1-ynyl-, pent-2-ynyl-, pent-3-ynyl-, pent-4-ynyl-, hex-1-ynyl-, hex-2-ynyl-, hex-3-ynyl-, hex-4-ynyl-, hex-5-ynyl-, 1-methylprop-2-ynyl-, 2-methylbut-3-ynyl-, 1-methylbut-3-ynyl-, 1-methylbut-2-ynyl-, 3-methylbut-1-ynyl-, 1-ethylprop-2-ynyl-, 3-methylpent-4-ynyl-, 2-methylpent-4-ynyl-, 1-methylpent-4-ynyl-, 2-methylpent-3-ynyl-, 1-methylpent-3-ynyl-, 4-methylpent-2-ynyl-, 1-methylpent-2-ynyl-, 4-methylpent-1-ynyl-, 3-methylpent-1-ynyl-, 2-ethylbut-3-ynyl-, 1-ethylbut-3-ynyl-, 1-ethylbut-2-ynyl-, 1-propylprop-2-ynyl-, 1-isopropylprop-2-ynyl-, 2,2-dimethylbut-3-ynyl-, 1,1-dimethylbut-3-ynyl-, 1,1-dimethylbut-2-ynyl- or a 3,3-dimethylbut-1-ynyl-.

An ethynyl, prop-1-ynyl or prop-2-ynyl radical is preferred.

C$_n$-Cycloalkyl:

Monovalent, cyclic hydrocarbon ring having n carbon atoms.

C$_3$-C$_7$-Cycloalkyl ring includes:

cyclopropyl, cyclobutyl, cyclopentyl, cyclohexyl and cycloheptyl.

A cyclopropyl, cyclopentyl or a cyclohexyl ring is preferred.

C$_n$-Alkoxy:

Straight-chain or branched C$_n$-alkyl ether residue of the formula —OR with R=alkyl.

C$_n$-Aryl

C$_n$-Aryl is a monovalent, aromatic ring system without heteroatom having n carbon atoms.

C$_6$-Aryl is identical to phenyl. C$_{10}$-Aryl is identical to naphthyl.

Phenyl is preferred.

Heteroatoms

Heteroatoms are to be understood to include oxygen, nitrogen or sulphur atoms.

Heteroaryl

Heteroaryl is a monovalent, aromatic ring system having at least one heteroatom different from a carbon. Heteroatoms which may occur are nitrogen atoms, oxygen atoms and/or sulphur atoms. The valence bond may be on any aromatic carbon atom or on a nitrogen atom.

A monocyclic heteroaryl ring according to the present invention has 5 or 6 ring atoms.

Heteroaryl rings having 5 ring atoms include for example the rings:

thienyl, thiazolyl, furanyl, pyrrolyl, oxazolyl, imidazolyl, pyrazolyl, isoxazolyl, isothiazolyl, oxadiazolyl, triazolyl, tetrazolyl and thiadiazolyl.

Heteroaryl rings having 6 ring atoms include for example the rings:

pyridyl, pyridazinyl, pyrimidinyl, pyrazinyl and triazinyl.

A bicyclic heteroaryl ring according to the present invention has 9 or 10 ring atoms.

Heteroaryl rings having 9 ring atoms include for example the rings:

phthalidyl-, thiophthalidyl-, indolyl-, isoindolyl-, indazolyl-, benzothiazolyl-, indolonyl-, isoindolonyl-, benzofuranyl, benzothienyl, benzimidazolyl, benzoxazolyl, azocinyl, indolizinyl, purinyl.

Heteroaryl rings having 10 ring atoms include for example the rings:
isoquinolinyl-, quinolinyl-, benzoxazinonyl-, phthalazinonyl, quinolonyl-, isoquinolonyl-, quinazolinyl-, quinoxalinyl-, cinnolinyl-, phthalazinyl-, 1,7- or 1,8-naphthyridinyl-, quinolinyl-, isoquinolinyl-, quinazolinyl- or quinoxalinyl- Monocyclic heteroaryl rings having 5 or 6 ring atoms are preferred.

Heterocyclyl

Heterocyclyl in the context of the invention is a completely hydrogenated heteroaryl (completely hydrogenated heteroaryl-saturated heterocyclyl), i.e. a non-aromatic ring system having at least one heteroatom different from a carbon. Heteroatoms which may occur are nitrogen atoms, oxygen atoms and/or sulphur atoms. The valence bond may be on any carbon atom or on a nitrogen atom.

Heterocyclyl ring having 3 ring atoms includes for example:
aziridinyl.

Heterocyclyl ring having 4 ring atoms includes for example:
azetidinyl, oxetanyl.

Heterocyclyl rings having 5 ring atoms include for example the rings:
pyrrolidinyl, imidazolidinyl, pyrazolidinyl and tetrahydrofuranyl.

Heterocyclyl rings having 6 ring atoms include for example the rings:
piperidinyl, piperazinyl, morpholinyl, tetrahydropyranyl and thiomorpholinyl.

Heterocyclyl ring having 7 ring atoms includes for example:
azepanyl, oxepanyl, [1,3]-diazepanyl, [1,4]-diazepanyl.

Heterocyclyl ring having 8 ring atoms includes for example: oxocanyl, azocanyl.

Halogen

The term halogen includes fluorine, chlorine, bromine and iodine. Bromine is preferred.

A preferred subgroup are compounds of the general formula (I) in which $R^1$ is halogen, —$CF_3$, —$OCF_3$, $C_1$-$C_4$-alkyl or nitro, $R^2$ is a $C_1$-$C_{10}$-alkyl, $C_2$-$C_{10}$-alkenyl or $C_2$-$C_{10}$-alkynyl radical, a $C_3$-$C_7$-cycloalkyl, phenyl or a mono- or bicyclic heteroaryl ring or a heterocyclyl ring having 3 to 7 ring atoms,
in each case optionally substituted one or more times, identically or differently, by hydroxy, —$NR^8R^9$, —$NR^7$—C(O)—$R^{12}$ and/or a $C_1$-$C_4$-alkyl radical which is optionally itself substituted one or more times by hydroxy $R^3$ is
(i) hydroxy, halogen, cyano, nitro, —$CF_3$, —$OCF_3$, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, and/or
(ii) a $C_1$-$C_3$-alkyl and/or $C_1$-$C_3$-alkoxy radical which is optionally substituted one or more times, identically or differently, by halogen, hydroxy, $C_1$-$C_6$-alkoxy, —$CF_3$, —$OCF_3$ or —$NR^8R^9$, m is 0 or 1, $R^4$ is a $C_1$-$C_5$-alkyl radical, a $C_3$-$C_6$-cycloalkyl or a phenyl ring,
in each case optionally themselves substituted one or more times, identically or differently, by hydroxy, —$NR^8R^9$, cyano, halogen, —$CF_3$, $C_1$-$C_6$-alkoxy, —$OCF_3$ and/or $C_1$-$C_6$-alkyl,
or $R^3$ and $R^4$ together form a 5-membered ring which is fused to Q and which optionally comprises in addition to the double bond from Q a further double bond, $R^5$ is —$SO_2$—$(CH_2)_n$—$R^{12}$, where n is 0 or 1,
where $R^{12}$ is $CF_3$
or a $C_1$-$C_4$-alkyl radical, a $C_3$-$C_6$-cycloalkyl or phenyl ring or a heterocyclyl ring having 3 to 6 ring atoms or a monocyclic heteroaryl ring,
optionally in each case themselves substituted one or more times, identically or differently, by hydroxy, nitro, —$NR^8R^9$, cyano, halogen, —$CF_3$, $C_1$-$C_6$-alkyl, $C_1$-$C_6$-alkoxy and/or —$OCF_3$,
or $R^4$ and $R^5$ together form a 5-membered ring of the formula (I)

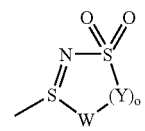

(1)

in which W and Y are each a —$CH_2$— group, and in which o is 1,

X is —O—, —S— or —$NR^{15}$—,
where
$R^{15}$ is
(i) hydrogen or
(ii) a $C_1$-$C_6$-alkyl radical, $C_3$-$C_8$-cycloalkyl or phenyl ring, a heterocyclyl ring having 3 to 8 ring atoms or a monocyclic heteroaryl ring, or
(iii) —C(O)—($C_1$-$C_6$)-alkyl, —C(O)-phenyl, or —C(O)-benzyl,
and (ii) and (iii) are optionally substituted one or more times, identically or differently, by hydroxy, —$NR^{10}R^{11}$, cyano, halogen, —$CF_3$, $C_1$-$C_6$-alkoxy and/or —$OCF_3$,
or
if X is —$NR^{15}$—, alternatively
X, $R^{15}$ and $R^2$ together form a 3 to 8 membered ring which optionally comprises in addition to the nitrogen atom one or more further heteroatoms, is optionally substituted one or more times, identically or differently, by hydroxy, $C_1$-$C_6$-alkyl, $C_1$-$C_6$-alkoxy, —C(O)$R^{12}$, —$SO_2R^{12}$, halogen or the group —$NR^8R^9$, optionally comprises 1 to 3 double bonds, and/or is optionally interrupted by one or more —C(O)— groups, Q is a phenyl, naphthyl or a monocyclic or bicyclic heteroaryl ring, $R^6$ is a $C_2$-$C_5$-alkyl, $C_4$-$C_6$-alkenyl, $C_4$-$C_6$-alkynyl or $C_2$-$C_5$-alkoxy radical, a $C_4$-$C_6$-cycloalkyl or phenyl ring, a heterocyclyl ring having 3 to 5 ring atoms or a monocyclic heteroaryl ring,
in each case optionally themselves substituted one or more times, identically or differently, by hydroxy, —$NR^8R^9$, cyano, halogen, —$CF_3$, $C_1$-$C_6$-alkoxy and/or —$OCF_3$, $R^7$ is hydrogen or a $C_1$-$C_6$-alkyl radical, $R^8$ and $R^9$ are each independently of one another hydrogen and/or a $C_1$-$C_4$-alkyl radical, $C_3$-$C_6$-cycloalkyl and/or phenyl ring, and/or a monocyclic heteroaryl ring, in each case optionally substituted one or more times, identically or differently, by hydroxy, —$NR^{10}R^{11}$ or $C_1$-$C_6$-alkoxy,
or $R^8$ and $R^9$ together with the nitrogen atom form a 5- to 7-membered ring which optionally comprises in addition to the nitrogen atom 1 further heteroatom, and which may be substituted one or more times by hydroxy, $R^{10}$ and $R^{11}$ are independently of one another hydrogen or a $C_1$-$C_6$-alkyl radical which is optionally substituted one or more times, identically or differently, by hydroxy, $R^{12}$ is a $C_1$-$C_6$-alkyl, $C_2$-$C_6$-alkenyl or $C_2$-$C_6$-alkynyl radical, a $C_3$-$C_7$-cycloalkyl or phenyl ring, a heterocyclyl ring having 3 to 8 ring atoms or a monocyclic heteroaryl ring,
in each case optionally themselves substituted one or more times, identically or differently, by hydroxy, halogen, nitro, —$NR^8R^9$, $C_1$-$C_6$-alkyl, and/or $C_1$-$C_6$-alkoxy, $R^{13}$ and $R^{14}$ are independently of one another a $C_1$-$C_6$-alkyl radical, and $R^{16}$ is a $C_1$-$C_6$-alkyl radical, a $C_3$-$C_7$-cycloalkyl or phenyl ring, a heterocyclyl ring having 3 to 8 ring atoms or a monocyclic heteroaryl ring, and the salts, diastereomers and enantiomers thereof.

Compounds from the preferred subgroup which are of particular interest are those in which in formula (I)

$R^4$ is a $C_1$-$C_5$-alkyl radical or a $C_3$-$C_6$-cycloalkyl ring,
in each case themselves optionally substituted one or more times, identically or differently, by hydroxy, —$NR^8R^9$, cyano, halogen, —$CF_3$, $C_1$-$C_6$-alkoxy, —$OCF_3$ and/or $C_1$-$C_6$-alkyl,
or $R^3$ and $R^4$ together form a 5-membered ring which is fused to Q and which optionally comprises in addition to the double bond from Q a further double bond, $R^5$ is —$SO_2R^{12}$,
where $R^{12}$ is a $C_1$-$C_4$-alkyl radical, a $C_3$-$C_6$-cycloalkyl or phenyl ring or a heterocyclyl ring having 3 to 6 ring atoms or a monocyclic heteroaryl ring,
optionally in each case themselves substituted one or more times, identically or differently, by hydroxy, nitro, —$NR^8R^9$, cyano, halogen, —$CF_3$, $C_1$-$C_6$-alkyl, $C_1$-$C_6$-alkoxy and/or —$OCF_3$,
or $R^4$ and $R^5$ together form a 5-membered ring of the formula (I)

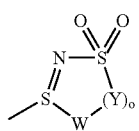

(1)

in which W and Y are each a —$CH_2$ group and in which o is 1, and the salts, diastereomers and enantiomers thereof.

A more preferred subgroup are compounds of the general formula (I) in which $R^1$ is hydrogen, halogen or —$CF_3$ $R^2$ is a $C_1$-$C_{10}$-alkyl radical, a $C_3$-$C_7$-cycloalkyl or phenyl ring, in each case optionally substituted one or more times, identically or differently, by hydroxy or —NH—C(O)—$C_1$-$C_6$-alkyl m is 0, $R^4$ is a $C_1$-$C_6$-alkyl radical, $R^5$ is —$SO_2$—$(CH_2)_n$—$R^{12}$ with n equal to 0 or 1, X is —NH—, Q is a phenyl ring, $R^{12}$ is —$CF_3$
or
is a $C_1$-$C_6$-alkyl radical, a phenyl or a monocyclic heteroaryl ring, which are optionally in each case themselves substituted one or more times, identically or differently, by nitro, halogen, —$CF_3$, $C_1$-$C_6$-alkyl, —NH—C(O)—$C_1$-$C_6$-alkyl, $C_1$-$C_6$-alkoxy and/or —$OCF_3$, and the salts, diastereomers and enantiomers thereof.

In the general formula (I), Q may be:
a phenyl, naphthyl or a monocyclic or bicyclic heteroaryl ring.

Q is preferably a phenyl or a monocyclic heteroaryl ring.

Q is more preferably a phenyl or a monocyclic heteroaryl ring having 6 ring atoms, in particular a pyridyl ring.

Q is particularly preferably a phenyl ring.

In the general formula (I), $R^1$ may be:

(i) hydrogen, halogen, cyano, nitro, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, —$CF_3$ or —$OCF_3$, or (ii) a $C_1$-$C_6$-alkyl, $C_2$-$C_6$-alkenyl, $C_1$-$C_6$-alkoxy or $C_2$-$C_6$-alkynyl radical which is optionally substituted one or more times, identically or differently, by hydroxy, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, cyano, halogen, $C_1$-$C_6$-alkoxy, —$CF_3$ and/or —$OCF_3$, or (iii) a phenyl or monocyclic heteroaryl ring which is optionally substituted one or more times, identically or differently, by hydroxy, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, cyano, halogen, —$CF_3$, $C_1$-$C_6$-alkoxy, —$OCF_3$ and/or $C_1$-$C_6$-alkyl.

$R^1$ is preferably:
halogen, —$CF_3$, —$OCF_3$, $C_1$-$C_4$-alkyl or nitro.

$R^1$ is more preferably halogen, —$CF_3$ or $C_1$-$C_2$-alkyl.

$R^1$ even more preferably is bromine and $CF_3$.

In the general formula (I), $R^2$ may be:

(i) hydrogen or (ii) a $C_1$-$C_{10}$-alkyl, $C_2$-$C_{10}$-alkenyl or $C_2$-$C_{10}$-alkynyl radical, a $C_3$-$C_7$-cycloalkyl, phenyl or naphthyl ring, a heterocyclyl ring having 3 to 8 ring atoms or a mono- or bicyclic heteroaryl ring,
in each case optionally substituted one or more times, identically or differently, by a) halogen, hydroxy, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, cyano, —C(O)$R^6$, —O(CO)—$R^{12}$, —$SO_2NR^8R^9$, —$SO_2$—$R^{12}$, —S(O)($NR^8$)$R^{12}$, —(N)S(O)$R^{13}R^{14}$, —$CF_3$, —$OCF_3$, —N[(CO)—($C_1$-$C_6$-alkyl)]$_2$ and/or b) $C_1$-$C_6$-alkoxy, $C_1$-$C_6$-alkyl, $C_2$-$C_6$-alkenyl, $C_2$-$C_6$-alkynyl, $C_3$-$C_8$-cycloalkyl, phenyl, naphthyl, heterocyclyl having 3 to 8 ring atoms and/or a monocyclic or bicyclic heteroaryl, in each case optionally themselves substituted one or more times, identically or differently, by halogen, hydroxy, a $C_1$-$C_6$-alkyl, $C_1$-$C_6$-alkoxy, —$NR^8R^9$, —C(O)$OR^{16}$, —$SO_2NR^8R^9$, —$CF_3$ or —$OCF_3$.

$R^2$ is preferably:
a $C_1$-$C_{10}$-alkyl, $C_2$-$C_{10}$-alkenyl or $C_2$-$C_{10}$-alkynyl radical, a $C_3$-$C_7$-cycloalkyl, phenyl or a mono- or bicyclic heteroaryl ring, a heterocyclyl ring having 3 to 7 ring atoms, in each case optionally substituted one or more times, identically or differently, by hydroxy, —$NR^8R^9$, —$NR^7$—C(O)—$R^{12}$ and/or a $C_1$-$C_4$-alkyl radical which is optionally itself substituted one or more times by hydroxy.

$R^2$ is more preferably:

a $C_2$-$C_6$-alkyl, $C_2$-$C_8$-alkenyl or $C_2$-$C_8$-alkynyl radical, a $C_3$-$C_6$-cycloalkyl, phenyl ring, a monocyclic heteroaryl ring having 6 ring atoms, a heterocyclyl ring having 5 to 7 ring atoms, in each case optionally substituted one or more times, identically or differently, by hydroxy, —$NR^8R^9$, —$NR^7$—C(O)—$R^{12}$ and/or a $C_1$-$C_4$-alkyl radical which is optionally itself substituted one or more times by hydroxy.

$R^2$ is particularly preferably:

a $C_1$-$C_6$-alkyl radical, a $C_3$-$C_7$-cycloalkyl or phenyl ring, in each case optionally substituted one or more times, identically or differently, by hydroxy and/or —NH—C(O)—$C_1$-$C_6$-alkyl.

In the general formula (I), X may be:

—O—, —S— or —$NR^{15}$—, where $R^{15}$ is (i) hydrogen or (ii) a $C_1$-$C_6$-alkyl radical, $C_3$-$C_8$-cycloalkyl or phenyl ring, a heterocyclyl ring having 3 to 8 ring atoms or a monocyclic heteroaryl ring, or (iii) —C(O)—($C_1$-$C_6$)-alkyl, —C(O)-phenyl, or —C(O)-benzyl, where (ii) and (iii) are optionally substituted one or more times, identically or differently, by hydroxy, —$NR^{10}R^{11}$, cyano, halogen, —$CF_3$, $C_1$-$C_6$-alkoxy and/or —$OCF_3$, or if X is —$NR^{15}$—, alternatively X, $R^{15}$ and $R^2$ together form a 3 to 8 membered ring which optionally comprises in addition to the nitrogen atom one or more further heteroatoms, is optionally substituted one or more times, identically or differently, by hydroxy, $C_1$-$C_6$-alkyl, $C_1$-$C_6$-alkoxy, —C(O)$R^{12}$, —$SO_2R^{12}$, halogen or the group —$NR^8R^9$, optionally comprises 1 to 3 double bonds, and/or is optionally interrupted by one or more —C(O)— groups.

X is preferably:

—O—, —S— or —$NR^{15}$—, where $R^{15}$ is hydrogen or a $C_1$-$C_6$-alkyl radical, $C_3$-$C_8$-cycloalkyl or a heterocyclyl ring having 3 to 8 ring atoms, in each case optionally substituted one or more times, identically or differently, by hydroxy, —$NR^{10}R^{11}$, cyano, halogen, —$CF_3$, $C_1$-$C_6$-alkoxy and/or —$OCF_3$, or if X is —$NR^{15}$—, X, $R^{15}$ and $R^2$ preferably alternatively together form a 3 to 6 membered ring which optionally comprises in addition to the nitrogen atom one further heteroatom, is optionally substituted one or more times, identically or differently, by hydroxy, $C_1$-$C_6$-alkyl, $C_1$-$C_6$-alkoxy, —C(O)$R^{12}$, —$SO_2R^{12}$, halogen or the group —$NR^8R^9$, optionally comprises 1 or 2 double bonds, and/or is interrupted by a —C(O)— group.

X is more preferably —$NR^{15}$—, where $R^{15}$ is hydrogen or a $C_3$-$C_6$-alkyl radical, $C_3$-$C_7$-cycloalkyl or a heterocyclyl ring having 3 to 6 ring atoms, in each case optionally substituted one or more times, identically or differently, by hydroxy, —$NR^{10}R^{11}$, cyano, halogen, —$CF_3$, $C_1$-$C_6$-alkoxy and/or —$OCF_3$, or if X is —$NR^{15}$—, X, $R^{15}$ and $R^2$ more preferably alternatively together form a 5 or 6 membered ring which optionally comprises in addition to the nitrogen a further heteroatom, and which is optionally substituted one or more times, identically or differently, by hydroxy, $C_1$-$C_6$-alkyl, $C_1$-$C_6$-alkoxy, —C(O)$R^{12}$, —$SO_2R^{12}$, halogen or the group —$NR^8R^9$.

X is particularly preferably —$NR^{15}$—, where $R^{15}$ is hydrogen.

In the general formula (I), $R^3$ can be:

(i) hydroxy, halogen, cyano, nitro, —$CF_3$, —$OCF_3$, —C(O)$NR^8R^9$, —C(S)$NR^8R^9$, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, and/or (ii) a $C_1$-$C_6$-alkyl and/or $C_1$-$C_6$-alkoxy radical which is optionally substituted one or more times, identically or differently, by halogen, hydroxy, $C_1$-$C_6$-alkoxy, —$CF_3$, —$OCF_3$ or —$NR^8R^9$ and/or (iii) a $C_3$-$C_7$-cycloalkyl ring which is optionally substituted one or more times, identically or differently, by halogen, hydroxy, $C_1$-$C_6$-alkoxy, —$CF_3$, —$OCF_3$, —$NR^8R^9$ and/or $C_1$-$C_6$-alkyl.

$R^3$ is preferably:

(i) hydroxy, halogen, cyano, nitro, —$CF_3$, —$OCF_3$, —C(O)$NR^8R^9$, —C(S)$NR^8R^9$, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, and/or (ii) a $C_1$-$C_5$-alkyl and/or $C_1$-$C_5$-alkoxy radical which is optionally substituted one or more times, identically or differently, by halogen, hydroxy, $C_1$-$C_6$-alkoxy, —$CF_3$, —$OCF_3$ or —$NR^8R^9$.

$R^3$ is more preferably (i) hydroxy, halogen, cyano, nitro, —$CF_3$, —$OCF_3$, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, and/or (ii) a $C_1$-$C_3$-alkyl and/or $C_1$-$C_3$-alkoxy radical which is optionally substituted one or more times, identically or differently, by halogen, hydroxy, $C_1$-$C_6$-alkoxy, —$CF_3$, —$OCF_3$ or —$NR^8R^9$.

$R^3$ is even more preferably:

(i) hydroxy, halogen, cyano, nitro, —$CF_3$, —$OCF_3$, —$NR^8R^9$ and/or (ii) a $C_1$-$C_3$-alkyl and/or $C_1$-$C_3$-alkoxy radical.

$R^3$ is particularly preferably:

hydroxy, fluorine, chlorine, bromine, cyano, nitro, —$CF_3$, methyl or methoxy.

In the general formula (I), m can be:

0-4, preferably 0 or 1, more preferably 0.

In the general formula (I), $R^4$ can be:

a $C_1$-$C_6$-alkyl, $C_2$-$C_6$-alkenyl, $C_2$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy, —$OCF_3$ and/or $C_1$-$C_6$-alkyl, or $R^3$ and $R^4$ form together a 5 to 7-membered ring which is fused to Q and which is optionally substituted one or more times, identically or differently, by hydroxy, $C_1$-$C_6$-alkyl, $C_1$-$C_6$-alkoxy, halogen or —$NR^8R^9$, and optionally comprises in addition to the double bond from Q a further double bond if the ring is 5-membered.

$R^4$ is preferably:

a $C_1$-$C_6$-alkyl, $C_2$-$C_6$-alkenyl, $C_2$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, halogen, or $R^3$ and $R^4$ form preferably together a 5 to 7-membered ring which is fused to Q and which is optionally substituted one or more times, identically or differently, by hydroxy, halogen or —NR$^8$R$^9$, and optionally comprises a double bond if the ring is 5-membered.

R$^4$ even more preferably is a C$_1$-C$_5$-alkyl radical, a C$_3$-C$_6$-cycloalkyl or a phenyl ring, in each case optionally themselves substituted one or more times, identically or differently, by hydroxy, —NR$^8$R$^9$, cyano, halogen, —CF$_3$, C$_1$-C$_6$-alkoxy, —OCF$_3$ and/or C$_1$-C$_6$-alkyl, or R$^3$ and R$^4$ form preferably together a 5-membered ring which is fused to Q and which optionally comprises in addition to the double bond from Q a further double bond.

R$^4$ is particularly preferably a C$_1$-C$_4$-alkyl radical, a C$_3$-C$_5$-cycloalkyl or a phenyl ring, in each case optionally themselves substituted one or more times, identically or differently, by hydroxy, —NR$^8$R$^9$ or halogen.

R$^4$ is very particularly preferably a C$_1$-C$_3$-alkyl radical.

In the general formula (I), R$^5$ can be:
—SO$_2$—(CH$_2$)$_n$—R$^{12}$ with n equal to 0 or 1, —C(O)R$^{12}$, —C(O)OR$^{12}$, —C(O)NR$^8$R$^9$, —C(S)OR$^{12}$, —C(S)NR$^8$R$^9$ or —R$^{12}$ where R$^{12}$ is —CF$_3$ or is a C$_1$-C$_6$-alkyl, C$_2$-C$_6$-alkenyl and/or C$_2$-C$_6$-alkynyl radical, a C$_3$-C$_7$-cycloalkyl or phenyl ring, a heterocyclyl ring having 3 to 8 ring atoms or a monocyclic heteroaryl ring, optionally in each case themselves substituted one or more times, identically or differently, by hydroxy, nitro, —NR$^8$R$^9$, —NH—C(O)—C$_1$-C$_6$-alkyl, cyano, halogen, —CF$_3$, C$_1$-C$_6$-alkyl, C$_1$-C$_6$-alkoxy and/or —OCF$_3$.

R$^5$ is preferably:
—SO$_2$R$^{12}$, —C(O)R$^{12}$, —C(O)OR$^{12}$, —C(O)NR$^8$R$^9$, —C(S)OR$^{12}$, —C(S)NR$^8$R$^9$ or —R$^{12}$ where R$^{12}$ is a C$_1$-C$_6$-alkyl, C$_2$-C$_6$-alkenyl and/or C$_2$-C$_6$-alkynyl radical, a C$_3$-C$_7$-cycloalkyl or phenyl ring, a heterocyclyl ring having 3 to 8 ring atoms or a monocyclic heteroaryl ring, optionally in each case themselves substituted one or more times, identically or differently, by hydroxy, nitro, —NR$^8$R$^9$, cyano, halogen, —CF$_3$, C$_1$-C$_6$-alkyl, C$_1$-C$_6$-alkoxy and/or —OCF$_3$, or R$^4$ and R$^5$ form together a 5 to 7-membered ring of the formula (I)

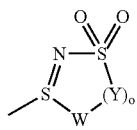

(1)

or of the formula (2)

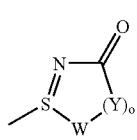

(2)

in which

W and Y are in each case independently of one another a —CH$_2$— group which is optionally substituted one or more times, identically or differently, by hydroxy, C$_1$-C$_6$-alkyl, C$_1$-C$_6$-alkoxy or —NR$^8$R$^9$, where the C$_1$-C$_6$-alkyl and/or C$_1$-C$_6$-alkoxy substitutent is optionally itself substituted one or more times, identically or differently, by hydroxy, C$_1$-C$_6$-alkoxy or —NR$^8$R$^9$, and/or optionally comprises in addition to the imide double bond 1 or 2 further double bonds and in which o is 1-3.

R$^5$ is also preferably —SO$_2$R$^{12}$ or —C(O)R$^{12}$, where R$^{12}$ is a C$_1$-C$_5$-alkyl, C$_2$-C$_5$-alkenyl and/or C$_2$-C$_5$-alkynyl radical, a C$_3$-C$_7$-cycloalkyl or phenyl ring, a heterocyclyl ring having 3 to 6 ring atoms and/or a monocyclic heteroaryl ring, optionally in each case themselves substituted one or more times, identically or differently, by hydroxy, nitro, —NR$^8$R$^9$, cyano, halogen, —CF$_3$, C$_1$-C$_6$-alkyl, C$_1$-C$_6$-alkoxy and/or —OCF$_3$, or R$^4$ and R$^5$ form preferably together a 5 to 7-membered ring of the formula (I)

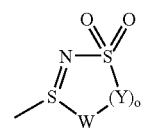

(1)

or of the formula (2)

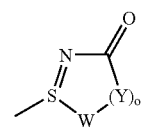

(2)

in which

W and Y are in each case independently of one another a —CH$_2$— group which is optionally substituted one or more times, identically or differently, by hydroxy, C$_1$-C$_6$-alkyl, C$_1$-C$_6$-alkoxy or —NR$^8$R$^9$, and in which o is 1-3.

R$^5$ is more preferably —SO$_2$—(CH$_2$)$_n$—R$^{12}$ with n equal to 0 or 1 where R$^{12}$ is —CF$_3$ or is a C$_1$-C$_6$-alkyl radical, a phenyl or a monocyclic heteroaryl ring, which are optionally in each case themselves substituted one or more times, identically or differently, by nitro, —NH—C(O)—C$_1$-C$_6$-alkyl, halogen, C$_1$-C$_6$-alkyl, C$_1$-C$_6$-alkoxy and/or —OCF$_3$.

R$^5$ is likewise more preferably —SO$_2$R$^{12}$, where R$^{12}$ is —CF$_3$ or is a C$_1$-C$_4$-alkyl radical, a C$_3$-C$_6$-cycloalkyl or phenyl ring or a heterocyclyl ring having 3 to 6 ring atoms or a monocyclic heteroaryl ring, optionally in each case themselves substituted one or more times, identically or differently, by hydroxy, nitro, —NR$^8$R$^9$, cyano, halogen, —CF$_3$, C$_1$-C$_6$-alkyl, C$_1$-C$_6$-alkoxy and/or —OCF$_3$, or R$^4$ and R$^5$ form preferably together a 5-membered ring of the formula (1)

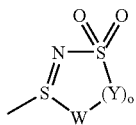

in which W and Y are each a —CH$_2$— group and in which o is 1.

R$^5$ is particularly preferably —SO$_2$—(CH$_2$)$_n$—R$^{12}$ with n equal to 0 or 1 where R$^{12}$ is —CF$_3$ or is a C$_1$-C$_6$-alkyl radical or a phenyl, pyridyl, thienyl or thiadiazolyl ring, which are optionally in each case themselves substituted one or more times, identically or differently, by nitro, —NH—C(O)—C$_1$-C$_6$-alkyl, halogen, C$_1$-C$_6$-alkyl, C$_1$-C$_6$-alkoxy and/or —OCF$_3$.

R$^5$ is likewise particularly preferably —SO$_2$R$^{12}$ where R$^{12}$ is a C$_1$-C$_6$-alkyl radical, a phenyl or a monocyclic heteroaryl ring, optionally in each case themselves substituted one or more times, identically or differently, by nitro, halogen and/or C$_1$-C$_6$-alkyl.

In the general formula (I), R$^6$ can be:

(i) hydrogen or hydroxy, or (ii) a C$_1$-C$_6$-alkyl, C$_3$-C$_6$-alkenyl, C$_3$-C$_6$-alkynyl or C$_1$-C$_6$-alkoxy radical, a C$_3$-C$_7$-cycloalkyl or phenyl ring, a heterocyclyl ring having 3 to 8 ring atoms or a monocyclic heteroaryl ring, in each case optionally themselves substituted one or more times, identically or differently, by hydroxy, —NR$^8$R$^9$, cyano, halogen, —CF$_3$, C$_1$-C$_6$-alkoxy and/or —OCF$_3$.

R$^6$ is preferably:

(i) hydrogen or (ii) a C$_1$-C$_4$-alkyl, C$_3$-C$_5$-alkenyl, C$_3$-C$_5$-alkynyl or C$_1$-C$_5$-alkoxy radical, a C$_3$-C$_6$-cycloalkyl or phenyl ring, a heterocyclyl ring having 3 to 6 ring atoms or a monocyclic heteroaryl ring, in each case optionally themselves substituted one or more times, identically or differently, by hydroxy, —NR$^3$R$^9$, cyano, halogen, —CF$_3$, C$_1$-C$_6$-alkoxy and/or —OCF$_3$.

R$^6$ is more preferably:

a C$_2$-C$_5$-alkyl, C$_4$-C$_6$-alkenyl, C$_4$-C$_6$-alkynyl or C$_2$-C$_5$-alkoxy radical, a C$_4$-C$_6$-cycloalkyl or phenyl ring, a heterocyclyl ring having 3 to 5 ring atoms or a monocyclic heteroaryl ring, in each case optionally themselves substituted one or more times, identically or differently, by hydroxy, —NR$^8$R$^9$, cyano, halogen, —CF$_3$, C$_1$-C$_6$-alkoxy and/or —OCF$_3$.

R$^6$ is particularly preferably:

a C$_1$-C$_6$-alkyl, a C$_1$-C$_6$-alkoxy radical or a C$_3$-C$_7$-cycloalkyl ring, in each case optionally themselves substituted one or more times, identically or differently, by hydroxy, —NR$^8$R$^9$ and/or C$_1$-C$_6$-alkoxy.

In the general formula (I), R$^7$ may be hydrogen or a C$_1$-C$_6$-alkyl radical.

In the general formula (I), R$^8$ and R$^9$ may be independently of one another:

(i) hydrogen and/or (ii) a C$_1$-C$_6$-alkyl radical, C$_2$-C$_6$-alkenyl, C$_3$-C$_8$-cycloalkyl and/or phenyl ring, a heterocyclyl ring having 3 to 8 ring atoms and/or a monocyclic heteroaryl ring, in each case optionally substituted one or more times, identically or differently, by hydroxy, —NR$^{10}$R$^{11}$, cyano, halogen, —CF$_3$, C$_1$-C$_6$-alkoxy and/or —OCF$_3$, or R$^8$ and R$^9$ form together with the nitrogen atom a 5- to 7-membered ring which optionally comprises in addition to the nitrogen atom 1 or 2 further heteroatoms, and which may be substituted one or more times, identically or differently, by hydroxy, —NR$^{10}$R$^{11}$, cyano, halogen, —CF$_3$, C$_1$-C$_6$-alkoxy and/or —OCF$_3$.

R$^8$ and R$^9$ are preferably:

(i) hydrogen and/or (ii) a C$_1$-C$_5$-alkyl, C$_2$-C$_5$-alkenyl radical, a C$_3$-C$_7$-cycloalkyl and/or phenyl ring and/or a monocyclic heteroaryl ring, in each case optionally substituted one or more times, identically or differently, by hydroxy, —NR$^{10}$R$^{11}$ and/or C$_1$-C$_6$-alkoxy, or R$^8$ and R$^9$ form together with the nitrogen atom a 5- to 7-membered ring which optionally comprises in addition to the nitrogen atom 1 further heteroatom and which may be substituted one or more times, identically or differently, by hydroxy, —NR$^{10}$R$^{11}$ and/or C$_1$-C$_6$-alkoxy.

R$^8$ and R$^9$ are more preferably:

(i) hydrogen and/or (ii) a C$_1$-C$_4$-alkyl radical, C$_3$-C$_6$-cycloalkyl and/or phenyl ring, and/or a monocyclic heteroaryl ring, in each case optionally substituted one or more times, identically or differently, by hydroxy, —NR$^{10}$R$^{11}$ or C$_1$-C$_6$-alkoxy, or R$^8$ and R$^9$ form together with the nitrogen atom a 5- to 7-membered ring which optionally comprises in addition to the nitrogen atom 1 further heteroatom, and which may be substituted one or more times by hydroxy.

R$^8$ and R$^9$ are particularly preferably:

(i) hydrogen and/or (ii) a C$_1$-C$_6$-alkyl radical, a C$_3$-C$_6$-cycloalkyl and/or phenyl ring and/or a monocyclic heteroaryl ring, or R$^8$ and R$^9$ form together with the nitrogen atom a 5- or 6-membered ring which optionally comprises in addition to the nitrogen atom 1 further heteroatom.

In the general formula (I), R$^{10}$ and R$^{11}$ may be independently of one another hydrogen or a C$_1$-C$_6$-alkyl radical which is optionally substituted one or more times, identically or differently, by hydroxy, cyano, halogen, —CF$_3$, C$_1$-C$_6$-alkoxy and/or —OCF$_3$.

R$^{10}$ and R$^{11}$ may preferably independently of one another be hydrogen or a C$_1$-C$_6$-alkyl radical which is optionally substituted one or more times, identically or differently, by hydroxy, halogen or C$_1$-C$_6$-alkoxy.

R$^{10}$ and R$^{11}$ may more preferably be independently of one another hydrogen or a C$_1$-C$_6$-alkyl radical which is optionally substituted one or more times, identically or differently, by hydroxy.

R$^{10}$ and R$^{11}$ may particularly preferably be independently of one another hydrogen or a methyl group.

In the general formula (I), R$^{12}$, R$^{13}$, R$^{14}$ may be independently of one another a —CF$_3$ or a C$_1$-C$_6$-alkyl, C$_2$-C$_6$-alkenyl and/or C$_2$-C$_6$-alkynyl radical, a C$_3$-C$_7$-cycloalkyl or phenyl ring, a heterocyclyl ring having 3 to 8 ring atoms or a monocyclic heteroaryl ring, which are optionally in each case themselves substituted one or more times, identically or differently, by hydroxy, nitro, —$NR^8R^9$, —NH—C(O)—$C_1$-$C_6$-alkyl, cyano, halogen, —$CF_3$, $C_1$-$C_6$-alkyl, $C_1$-$C_6$-alkoxy and/or —$OCF_3$.

$R^{12}$, $R^{13}$, $R^{14}$ are preferably independently of one another a $C_1$-$C_6$-alkyl, $C_2$-$C_6$-alkenyl and/or $C_2$-$C_6$-alkynyl radical, a $C_3$-$C_7$-cycloalkyl and/or phenyl ring, a heterocyclyl ring having 3 to 8 ring atoms and/or a monocyclic heteroaryl ring, in each case optionally themselves substituted one or more times, identically or differently, by hydroxy, nitro, —$NR^8R^9$, cyano, halogen, —$CF_3$, $C_1$-$C_6$-alkyl, $C_1$-$C_6$-alkoxy and/or —$OCF_3$.

$R^{12}$ is preferably a $C_1$-$C_6$-alkyl, $C_2$-$C_6$-alkenyl or $C_2$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, halogen, nitro, —$NR^8R^9$, $C_1$-$C_6$-alkyl and/or $C_1$-$C_6$-alkoxy.

$R^{12}$ is more preferably a $C_1$-$C_5$-alkyl, $C_2$-$C_5$-alkenyl, a $C_3$-$C_6$-cycloalkyl or phenyl ring, a heterocyclyl ring having 3 to 6 ring atoms or a monocyclic heteroaryl ring, in each case optionally themselves substituted one or more times, identically or differently, by hydroxy, halogen, nitro, —$NR^8R^9$, $C_1$-$C_6$-alkyl and/or $C_1$-$C_6$-alkoxy.

$R^{12}$ is particularly preferably —$CF_3$ or is a $C_1$-$C_6$-alkyl radical, a phenyl or a monocyclic heteroaryl ring, which are optionally in each case themselves substituted one or more times, identically or differently, by nitro, —NH—C(O)—$C_1$-$C_6$-alkyl, halogen, $C_1$-$C_6$-alkyl, $C_1$-$C_6$-alkoxy and/or —$OCF_3$.

$R^{12}$ is likewise particularly preferably a $C_1$-$C_6$-alkyl radical, a phenyl or monocyclic heteroaryl ring, in each case optionally themselves substituted one or more times, identically or differently, by hydroxy, halogen, nitro or $C_1$-$C_6$-alkyl.

$R^{13}$ and $R^{14}$ are preferably independently of one another a $C_1$-$C_6$-alkyl, $C_2$-$C_6$-alkenyl and/or $C_2$-$C_6$-alkynyl radical, a $C_3$-$C_7$-cycloalkyl and/or phenyl ring, a heterocyclyl ring having 3 to 8 ring atoms and/or a monocyclic heteroaryl ring, in each case optionally themselves substituted one or more times, identically or differently, by hydroxy, —$NR^8R^9$ and/or $C_1$-$C_6$-alkoxy.

$R^{13}$ and $R^{14}$ are more preferably independently of one another a $C_1$-$C_5$-alkyl, $C_2$-$C_5$-alkenyl and/or $C_2$-$C_5$-alkynyl radical, a $C_3$-$C_6$-cycloalkyl and/or phenyl ring, a heterocyclyl ring having 3 to 6 ring atoms and/or a monocyclic heteroaryl ring.

$R^{13}$ and $R^{14}$ are particularly preferably independently of one another a $C_1$-$C_6$-alkyl radical.

In the general formula (I), $R^{16}$ may be:
(i) hydrogen or
(ii) a $C_1$-$C_6$-alkyl, $C_3$-$C_6$-alkenyl, $C_3$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy and/or —$OCF_3$.

$R^{16}$ may preferably be:
a $C_1$-$C_6$-alkyl, $C_3$-$C_6$-alkenyl, $C_3$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy and/or —$OCF_3$.

$R^{16}$ can more preferably be:
a $C_1$-$C_6$-alkyl radical, a $C_3$-$C_7$-cycloalkyl or phenyl ring, a heterocyclyl ring having 3 to 8 ring atoms or a monocyclic heteroaryl ring.

$R^{16}$ may particularly preferably be a $C_1$-$C_6$-alkyl radical.

Likewise to be regarded as encompassed by the present invention are all compounds which result from every possible combination of the abovementioned possible, preferred and particularly preferred meanings of the substituents.

Special embodiments of the invention moreover consist of compounds which result from combination of the meanings disclosed directly in the examples for the substituents.

The compounds according to the invention can be prepared by a process which includes the following steps:
a) reaction of 2-chloropyrimidines of the formula (IV) with nucleophiles of the formula (III) to give compounds of the formula (II)

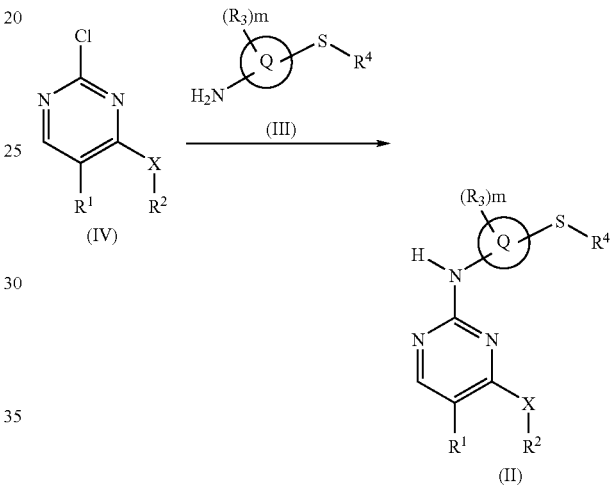

b) imination of the thioethers of the formula (II) to obtain compounds of the formula (I)

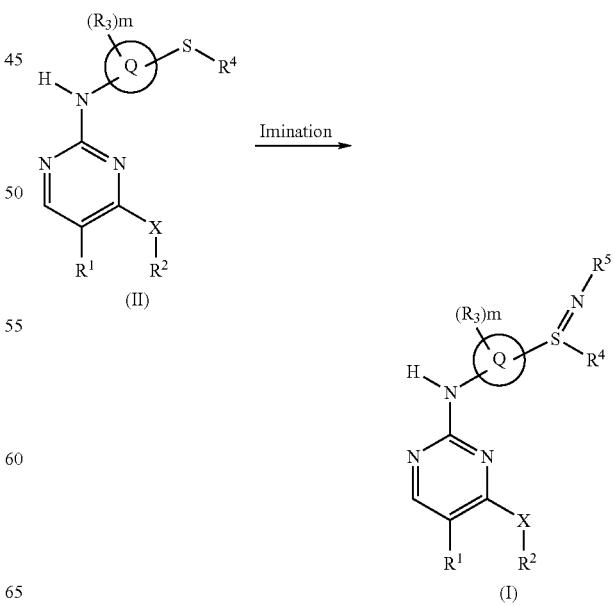

where Q, $R^1$, $R^2$, $R^3$, $R^4$, $R^5$, X and m have the meanings indicated in the general formula (I) according to Claims 1 to 17.

The present invention likewise relates to intermediates of the formula (IV):

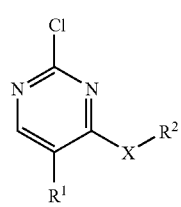

(IV)

where $R^1$, $R^2$ and X have the meanings indicated in the general formula (I) according to Claims 1 to 20.

The intermediates of the formula (IV) can be prepared by reacting 2,4-dichloro-pyrimidines of the formula (VI) with nucleophiles of the formula (V)

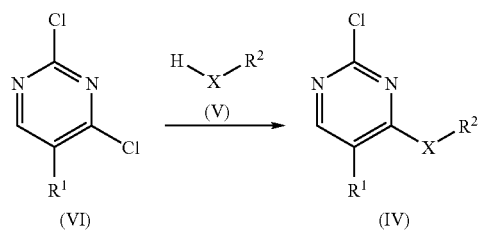

where $R^1$, $R^2$ and X have the meanings indicated in the general formula (I) according to Claims 1 to 20.

Alternatively, the compounds according to the invention can be prepared by reacting 2-chloropyrimidines of the formula (IV) with nucleophiles of the formula (VII),

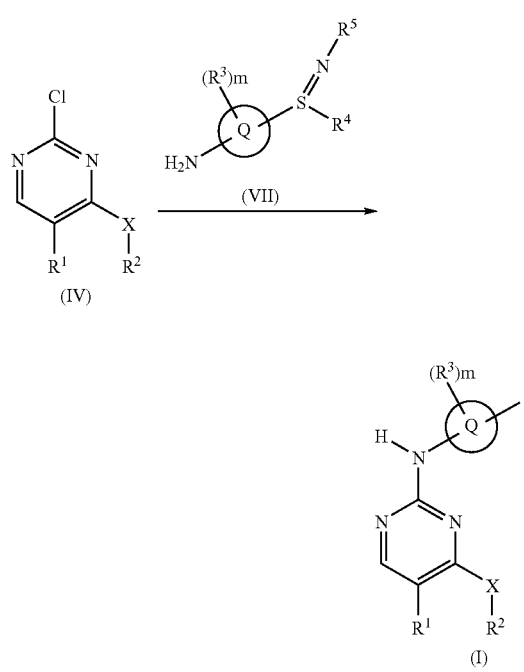

where Q, $R^1$, $R^2$, $R^3$, $R^4$, $R^5$, X and m have the meanings indicated in the general formula (I) according to Claims 1 to 20.

The present invention likewise relates to intermediates of the formula (VII):

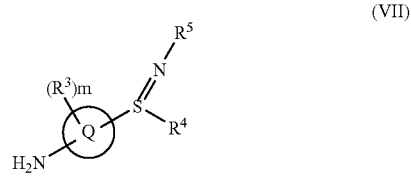

(VII)

where Q, $R^3$, $R^4$ and $R^5$ have the meanings indicated in the general formula (I) according to Claims 1 to 20.

The intermediates of the formula (VII) can be prepared by a process which includes the following steps:

a) imination of a thioether of the formula (IX) to obtain sulphimides of the formula (VII)

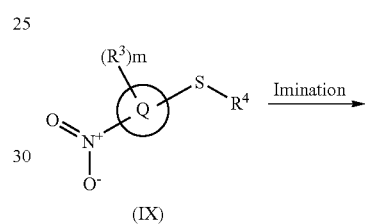

(IX)

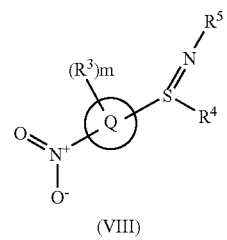

(VIII)

b) reduction of the nitro group to obtain the intermediates of the formula (VII)

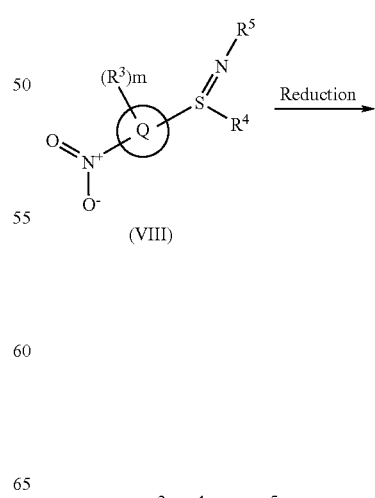

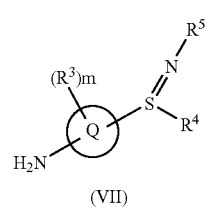

(VII)

where Q, $R^3$, $R^4$ and $R^5$ have the meanings indicated in the general formula (I) according to Claims 1 to 20.

Alternatively, the intermediates of the formula (VII) can also be prepared by a process which includes the following steps:

a) imination of a thioether of the formula (X) to obtain sulphimides of the formula (XI)

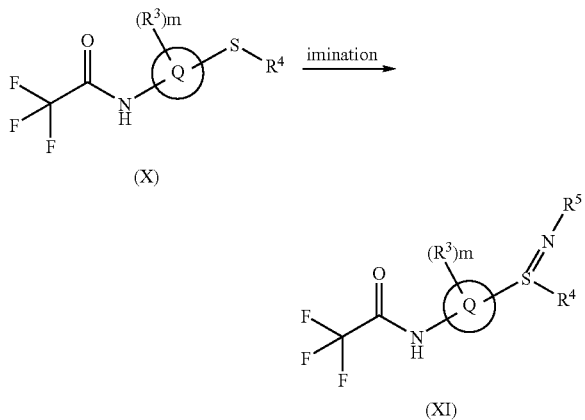

b) elimination of the protective group to obtain the intermediates of the formula (VII)

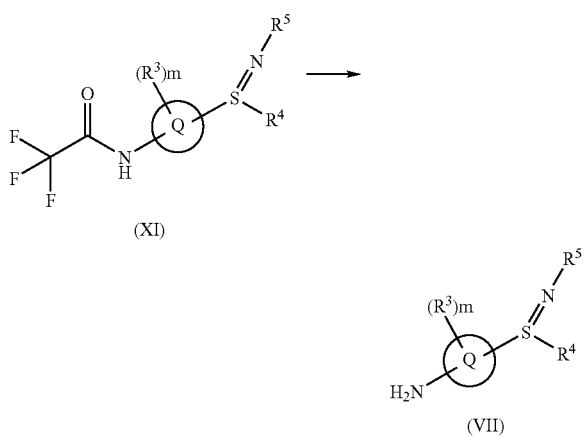

where Q, $R^3$, $R^4$ and $R^5$ have the meanings indicated in the general formula (I) according to Claims 1 to 20.

The following grouping of protein kinases underlies the application:

A. cell cycle kinases: a) CDKS, b) Plk, c) Aurora
B. angiogenic receptor tyrosine kinases: a) VEGF-R, b) Tie, c) FGF-R, d) EphB4
C. proliferative receptor tyrosine kinases: a) PDGF-R, Flt-3, c-Kit
D. checkpoint kinases: a) ATM/ATR, b) Chk ½, c) TTK/hMps1, BubR1, Bub1
E. anti-apoptotic kinases a) AKT/PKB b) IKK c) PIM1, d) ILK
F. migratory kinases a) FAK, b) ROCK A. Cell Cycle Kinases a) CDKs, b) Plk, c) Aurora The eukaryotic cycle of cell division ensures duplication of the genome and its distribution to the daughter cells by passing through a coordinated and regulated sequence of events. The cell cycle is divided into four consecutive phases: the G1 phase represents the time before DNA replication in which the cell grows and is sensitive to external stimuli. In the S phase, the cell replicates its DNA, and in the G2 phase it prepares itself for entry into mitosis. In mitosis (M phase), the replicated DNA is separated and cell division is completed.

The cyclin-dependent kinases (CDKs), a family of serine/threonine kinases whose members require the binding of a cyclin (Cyc) as regulatory subunit for their activation, drive the cell through the cell cycle. Different CDK/Cyc pairs are active in the different phases of the cell cycle. CDK/Cyc pairs which are important for the basic function of the cell cycle are, for example, CDK4(6)/CycD, CDK2/CycE, CDK2/CycA, CDK1/CycA and CDK1/CycB.

Entry into the cell cycle and passing through the restriction point, which marks the independence of a cell from further growth signals for completion of the initiated cell division, are controlled by the activity of the CDK4(6)/CycD and CDK2/CycE complexes. The essential substrate of these CDK complexes is the retinoblastoma protein (Rb), the product of the retinoblastoma tumour suppressor gene. Rb is a transcriptional corepresssor protein. Besides other mechanisms which are still substantially not understood, Rb binds and inactivates transcription factors of the E2F type, and forms transcriptional repressor complexes with histone deacetylases (HDAC) (Zhang H. S. et al. (2000). Exit from G1 and S phase of the cell cycle is regulated by repressor complexes containing HDAC-Rb-hSWI/SNF and Rb-hSWI/SNF. Cell 101, 79-89). Phosphorylation of Rb by CDKs releases bound E2F transcription factors which lead to transcriptional activation of genes whose products are required for DNA synthesis and progression through the S phase. An additional effect of Rb phosphorylation is to break up Rb-HDAC complexes, thus activating further genes. Phosphorylation of Rb by CDKs is to be equated with going beyond the restriction point. The activity of CDK2/CycE and CDK2/CycA complexes is necessary for progression through the S phase and completion thereof. After replication of the DNA is complete, the CDK1 in the complex with CycA or CycB controls the passing through of the G2 phase and the entry of the cell into mitosis (FIG. 1). In the transition from the G2 phase into mitosis, the polo-like kinase Plk1 contributes to activating CDK1. While mitosis is in progress, Plk1 is further involved in the maturation of the centrosomes, the construction of the spindle apparatus, the separation of the chromosomes and the separation of the daughter cells.

The family of Aurora kinases consists in the human body of three members: Aurora-A, Aurora-B and Aurora-C. The Aurora kinases regulate important processes during cell division (mitosis).

Aurora-A is localized on the centrosomes and the spindle microtubules, where it phosphorylates various substrate proteins, inter alia kinesin Eg5, TACC, PP1. The exact mechanisms of the generation of the spindle apparatus and the role of Aurora-A therein are, however, still substantially unclear.

Aurora-B is part of a multiprotein complex which is localized on the centrosome structure of the chromosomes and, besides Aurora-B, comprises inter alia INCENP, survivin and borealin/dasra B (summarizing overview in: Vagnarelli & Earnshaw, Chromosomal passengers: the four-dimensional regulation of mitotic events. Chromosoma. 2004 Nov.; 113 (5):211-22. Epub 2004 Sep. 4). The kinase activity of Aurora-B ensures that all the connections to the microtubulin spindle apparatus are correct before division of the pairs of chromosomes (so-called spindle checkpoint). Substrates of Aurora-B are in this case inter alia histone H3 and MCAK. After separation of the chromosomes, Aurora-B alters its localization and can be found during the last phase of mitosis (cytokinesis) on the still remaining connecting bridge between the two daughter cells. Aurora-B regulates the severance of the daughter cells through phosphorylation of its substrates MgcRacGAP, vimentin, desmin, the light regulatory chain of myosin, and others.

Aurora-C is very similar in its amino acid sequence, localization, substrate specificity and function to Aurora-B (Li X et al. Direct association with inner centromere protein (INCENP) activates the novel chromosomal passenger protein, Aurora-C. J Biol. Chem. 2004 Nov. 5; 279(45):47201-11. Epub 2004 Aug. 16; Chen et al. Overexpression of an Aurora-C kinase-deficient mutant disrupts the Aurora-B/INCENP complex and induces polyploidy. J Biomed Sci. 2005; 12(2):297-310; Yan X et al. Aurora-C is directly associated with Survivin and required for cytokinesis. Genes to ells 2005 10, 617-626). The chief difference between Aurora-B and Aurora-C is the strong overexpression of Aurora-C in the testis (Tseng T C et al. Protein kinase profile of sperm and eggs: cloning and characterization of two novel testis-specific protein kinases (AIE1, AIE2) related to yeast and fly chromosome segregation regulators. DNA Cell Biol. 1998 Oct.; 17(10):823-33.).

The essential function of the Aurora kinases in mitosis makes them target proteins of interest for the development of small inhibitory molecules for the treatment of cancer or other disorders which are caused by disturbances of cell proliferation. Convincing experimental data indicate that inhibition of the Aurora kinases in vitro and in vivo prevents the advance of cellular proliferation and induces programmed cell death (apoptosis). It has been possible to show this by means of (1) siRNA technology (Du & Hannon. Suppression of p160ROCK bypasses cell cycle arrest after Aurora-A/STK15 depletion. Proc Natl Acad Sci USA. 2004 Jun. 15; 101 (24):8975-80. Epub 2004 Jun. 3; Sasai K et al. Aurora-C kinase is a novel chromosomal passenger protein that can complement Aurora-B kinase function in mitotic cells. Cell Motil Cytoskeleton. 2004 December; 59(4):249-63) or (2) overexpression of a dominant-negative Aurora kinase (Honda et al. Exploring the functional interactions between Aurora B, INCENP, and survivin in mitosis. Mol Biol Cell. 2003 Aug.; 14(8):3325-41. Epub 2003 May 29), and (3) with small chemical molecules which specifically inhibit Aurora kinases (Hauf S et al. The small molecule Hesperadin reveals a role for Aurora B in correcting kinetochore-microtubule attachment and in maintaining the spindle assembly checkpoint. J. Cell Biol. 2003 Apr. 28; 161 (2):281-94. Epub 2003 Apr. 21.; Ditchfield C et al. Aurora B couples chromosome alignment with anaphase by targeting BubR1, Mad2, and Cenp-E to kinetochores. J. Cell Biol. 2003 Apr. 28; 161 (2):267-80.).

Inactivation of Aurora kinases leads to (1) faulty or no development of the mitotic spindle apparatus (predominantly with Aurora-A inhibition) and/or (2) faulty or no separation of the sister chromatids through blocking of the spindle checkpoint (predominantly with Aurora-B/-C inhibition) and/or (3) incomplete separation of daughter cells (predominantly with Aurora-B/-C inhibition). These consequences (1-3) of the inactivation of Aurora kinases singly or as combinations lead eventually to aneuploidy and/or polyploidy and ultimately, immediately or after repeated mitoses, to a non-viable state or to programmed cell death of the proliferating cells (mitotic catastrophe).

Specific kinase inhibitors are able to influence the cell cycle at various stages. Thus, for example, blockade of the cell cycle in the G1 phase or in the transition from the G1 phase to the S phase is to be expected with a CDK4 or a CDK2 inhibitor.

B. Angiogenic Receptor Tyrosine Kinases

Receptor tyrosine kinases and their ligands are crucial participants in a large number of cellular processes involved in the regulation of the growth and differentiation of cells. Of particular interest here are the vascular endothelial growth factor (VEGF)/VEGF receptor system, the fibroblast growth factor (FGF)/FGF receptor system, the Eph ligand/Eph receptor system, and the Tie ligand/Tie receptor system. In pathological situations associated with an increased formation of new blood vessels (neovascularization) such as, for example, neoplastic diseases, an increased expression of angiogenic growth factors and their receptors has been found. Inhibitors of the VEGF/VEGF receptor system, FGF/FGF receptor system (Rousseau et al., The tyrp1-Tag/tyrp1-FGFR1-DN bigenic mouse: a model for selective inhibition of tumor development, angiogenesis, and invasion into the neural tissue by blockade of fibroblast growth factor receptor activity. Cancer Res. 64, :2490, 2004), of the EphB4 system (Kertesz et al., The soluble extracellular domain of EphB4 (sEphB4) antagonizes EphB4-EphrinB2 interaction, modulates angiogenesis and inhibits tumor growth. Blood. 2005 Dec. 1; [Epub ahead of print]), and of the Tie ligand/Tie system (Siemeister et al., Two independent mechanisms essential for tumor angiogenesis: inhibition of human melanoma xenograft growth by interfering with either the vascular endothelial growth factor receptor pathway or the Tie-2 pathway. Cancer Res. 59, 3185, 1999) are able to inhibit the development of a vascular system in tumours, thus cut the tumour off from the oxygen and nutrient supply, and therefore inhibit tumour growth.

C. Proliferative Receptor Tyrosine Kinases

Receptor tyrosine kinases and their ligands are crucial participants in the proliferation of cells. Of particular interest here are the platelet-derived growth factor (PDGF) ligand/PDGF receptor system, c-kit ligand/c-kit receptor system and the FMS-like tyrosine kinase 3 (Flt-3) ligand/Flt-3 system. In pathological situations associated with an increased growth of cells such as, for example, neoplastic diseases, an increased expression of proliferative growth factors and their receptors or kinase-activating mutations has been found. Inhibition of the enzymic activity of these receptor tyrosine kinases leads to a reduction of tumour growth. It has been possible to show this for example by studies with the small chemical molecule STI571/Glivec which inhibits inter alia PDGF-R and c-kit (summarizing overviews in: Oestmann A., PDGF receptors-mediators of autocrine tumor growth and regulators of tumor vasculature and stroma, Cytokine Growth Factor Rev. 2004 Aug.; 15(4):275-86; Roskoski R., Signaling by Kit protein-tyrosine kinase—the stem cell factor receptor. Biochem Biophys Res Commun. 2005 Nov. 11; 337(1):1-13.; Markovic A. et al., FLT-3: a new focus in the understanding of acute leukemia. Int J Biochem Cell Biol. 2005 June; 37(6): 1168-72. Epub 2005 Jan. 26.).

D. Checkpoint Kinases

Checkpoint kinases mean in the context of the present application cell cycle kinases which monitor the ordered progression of cell division, such as, for example, ATM and ATR, Chk1 and Chk2, Mps1, Bub1 and BubR1. Of particular importance are the DNA damage checkpoint in the G2 phase and the spindle checkpoint during mitosis.

The ATM, ATR, Chk1 and Chk2 kinases are activated by DNA damage to a cell and leads to arrest of the cell cycle in the G2 phase through inactivation of CDK1. (Chen & Sanchez, Chk1 in the DNA damage response: conserved roles from yeasts to mammals. DNA Repair 3, 1025, 2004). Inactivation of Chk1 causes loss of the G2 arrest induced by DNA damage, to the progression of the cell cycle in the presence of damaged DNA, and finally leads to cell death (Takai et al. Aberrant cell cycle checkpoint function and early embryonic death in Chk1 (−/−) mice.Genes Dev. 2000 Jun. 15; 14(12):

1439-47; Koniaras et al. Inhibition of Chk1-dependent G2 DNA damage checkpoint radiosensitizes p53 mutant human cells. Oncogene. 2001 Nov. 8; 20(51):7453-63.; Liu et al. Chk1 is an essential kinase that is regulated by Atr and required for the G(2)/M DNA damage checkpoint. Genes Dev. 2000 Jun. 15; 14(12):1448-59.). Inactivation of Chk1, Chk2 or Chk1 and Chk2 prevents the G2 arrest caused by DNA damage and makes proliferating cancer cells more sensitive to DNA-damaging therapies such as, for example, chemotherapy or radiotherapy. Chemotherapies leading to DNA damage are, for example, substances inducing DNA strand breaks, DNA-alkylating substances, topoisomerase inhibitors, Aurora kinase inhibitors, substances which influence the construction of the mitotic spindles, hypoxic stress owing to a limited oxygen supply to a tumour (e.g. induced by anti-angiogenic medicaments such as VEGF kinase inhibitors).

A second essential checkpoint within the cell cycle controls the correct construction and attachment of the spindle apparatus to the chromosomes during mitosis. The kinases TTK/hMps1, Bub1, and BubR1 are involved in this so-called spindle checkpoint (summarizing overview in: Kops et al. On the road to cancer: aneuploidy and the mitotic checkpoint. Nat Rev Cancer. 2005 Oct.; 5(10):773-85). These are localized on kinetochores of condensed chromosomes which are not yet attached to the spindle apparatus and inhibit the so-called anaphase-promoting complex/cyclosome (APC/C). Only after complete and correct attachment of the spindle apparatus to the kinetochores are the spindle checkpoint kinases Mps-1, Bub1, and BubR1 inactivated, thus activating APC/C and resulting in separation of the paired chromosomes. Inhibition of the spindle checkpoint kinases leads to separation of the paired chromosomes before all the kinetochores are attached to the spindle apparatus, and consequently to faulty chromosome distributions which are not tolerated by cells and finally lead to cell cycle arrest or cell death.

E. Anti-Apoptotic Kinases

Various mechanisms protect a cell from cell death during non-optimal living conditions. In tumour cells, these mechanisms lead to a survival advantage of the cells in the growing mass of the tumour, which is characterized by deficiency of oxygen, glucose and further nutrients, make it possible for tumour cells to survive without attachment to the extracellular matrix, possibly leading to metastasis, or lead to resistances to therapeutic agents. Essential anti-apoptotic signalling pathways include the PDK1-AKT/PKB signalling pathway (Altomare & Testa. Perturbations of the AKT signaling pathway in human cancer. Oncogene. 24, 7455, 2005), the NFkappaB signalling pathway (Viatour et al. Phosphorylation of NFkB and IkB proteins: implications in cancer and inflammation), the PIM1 signalling pathway (Hammerman et al. Pim and Akt oncogenes are independent regulators of hematopoietic cell growth and survival. Blood. 2005 105, 4477, 2005) and the integrin-linked kinase (ILK) signalling pathway (Persad & Dedhar. The role of integrin-linked kinase (ILK) in cancer progression. Cancer Met. Rev. 22, 375, 2003). Inhibition of the anti-apoptotic kinases such as, for example, AKT/PBK, PDK1, IkappaB kinase (IKK), PIM1, or ILK sensitizes the tumour cells to the effect of therapeutic agents or to unfavourable living conditions in the tumour environment. After inhibition of the anti-apoptotic kinases, tumour cells will react more sensitively to disturbances of mitosis caused by Aurora inhibition and undergo cell death in increased numbers.

F. Migratory Kinases

A precondition for invasive, tissue-infiltrating tumour growth and metastasis is that the tumour cells are able to leave the tissue structure through migration. Various cellular mechanisms are involved in regulating cell migration: integrin-mediated adhesion to proteins of the extracellular matrix regulates via the activity of focal adhesion kinase (FAK); control of the assembling of contractile actin filaments via the RhoA/Rho kinase (ROCK) signalling pathway (summarizing overview in M. C. Frame, Newest findings on the oldest oncogene; how activated src does it. J. Cell Sci. 117, 989, 2004).

The compounds according to the invention are effective for example against cancer such as solid tumours, tumour growth or metastasis growth, especially:

ataxia-telangiectasia, basal cell carcinoma, bladder carcinoma, brain tumour, breast cancer, cervical carcinoma, tumours of the central nervous system, colorectal carcinoma, endometrial carcinoma, stomach carcinoma, gastrointestinal carcinoma, head and neck tumours, acute lymphocytic leukaemia, acute myelogenous leukaemia, chronic lymphocytic leukaemia, chronic myelogenous leukaemia, hairy cell leukaemia, liver carcinoma, lung tumour, non-small-cell lung carcinoma, small-cell lung carcinoma, B-cell lymphoma, Hodgkin's lymphoma, non-Hodgkin's lymphoma, T-cell lymphoma, melanoma, mesothelioma, myeloma, myoma, tumours of the oesophagus, oral tumours, ovarian carcinoma, pancreatic tumours, prostate tumours, renal carcinoma, sarcoma, Kaposi's sarcoma, leiomyosarcoma, skin cancer, squamous cell carcinoma, testicular cancer, thyroid cancer, connective tissue tumour of the gastrointestinal tissue, connective tissue sarcoma of the skin, hypereosinophilic syndrome, mast cell cancer, for cardiovascular disorders such as stenoses, arterioscleroses and restenoses, stent-induced restenosis, for angiofibroma, Crohn's disease, endometriosis, haemangioma.

Formulation of the compounds according to the invention to give pharmaceutical products takes place in a manner known per se by converting the active ingredient(s) with the excepients customary in pharmaceutical technology into the desired administration form.

Excepients which can be employed in this connection are, for example, carrier substances, fillers, disintegrants, binders, humectants, lubricants, absorbents and adsorbents, diluents, solvents, cosolvents, emulsifiers, solubilizers, masking flavours, colorants, preservatives, stabilizers, wetting agents, salts to alter the osmotic pressure or buffers.

Reference should be made in this connection to Remington's Pharmaceutical Science, 15th ed. Mack Publishing Company, East Pennsylvania (1980).

The pharmaceutical formulations may be in solid form, for example as tablets, coated tablets, pills, suppositories, capsules, transdermal systems or in semisolid form, for example as ointments, creams, gels, suppositories, emulsions or in liquid form, for example as solutions, tinctures, suspensions or emulsions.

Excepients in the context of the invention may be, for example, salts, saccharides (mono-, di-, tri-, oligo- and/or polysaccharides), proteins, amino acids, peptides, fats, waxes, oils, hydrocarbons and their derivatives, where the excepients may be of natural origin or may be obtained by synthesis or partial synthesis.

Suitable for oral or peroral administration are in particular tablets, coated tablets, capsules, pills, powders, granules, pastilles, suspensions, emulsions or solutions. Suitable for parenteral administration are in particular suspensions, emulsions and especially solutions.

PREPARATION OF THE COMPOUNDS ACCORDING TO THE INVENTION

Process Variant 1

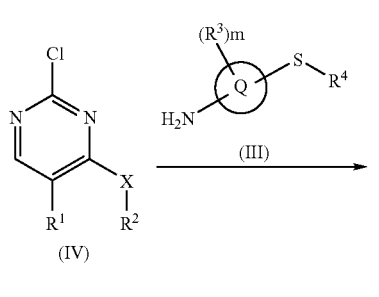

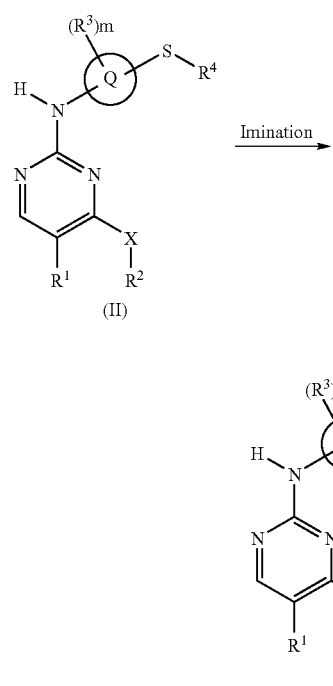

The substitutents Q, $R^1$, $R^2$, $R^3$, $R^4$, $R^5$, X and m have the meanings indicated in the general formula (I).

2-Chloropyrimidines of the formula (IV) can be reacted with nucleophiles of the formula (III) to give compounds of the formula (II). The resulting thioethers of the formula (II) can then be converted by imination into products of the formula (I) (for imination methods, see, for example: a) Johnson et al, *J. Org. Chem.* 1979, 44, 2065; b) Oae et al, *Org. Chem. Sulfur* 1977, 383; c) Kucsman et al, *Phosphorous Sulfur* 1977, 3, 9; d) Sharpless et al, *J. Org. Chem.* 2001, 66, 594; e) Katsuki et al, *Tetrahedron Lett.* 2001, 42, 7071; f) Bolm et al, *Org. Lett.* 2004, 6, 1305; g) Carreira et al, *Helv. Chim. Acta* 2002, 85, 3773; h) Bolm et al, *Org. Lett.* 2006, 8, 2349; i) Bolm et al, Org. Lett. 2005, 7, 4983; j) Bolm et al, *Org. Lett.* 2006, 8, 2349).

Preparation of the Intermediates of the Formula (IV):

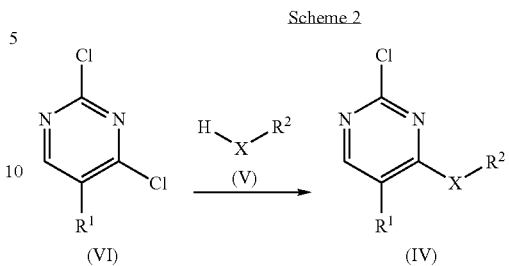

The substitutents $R^1$, $R^2$ and X have the meanings indicated in the general formula (I).

2,4-Dichloropyrimidines of the formula (VI) can be reacted with nucleophiles of the formula (V) to give compounds of the formula (IV) (see, for example: a) U. Lücking et al, WO 2005037800; b) J. Bryant et al, WO 2004048343; c) U. Lücking et al, WO 2003076437; d) T. Brumby et al, WO 2002096888).

Process Variant 2

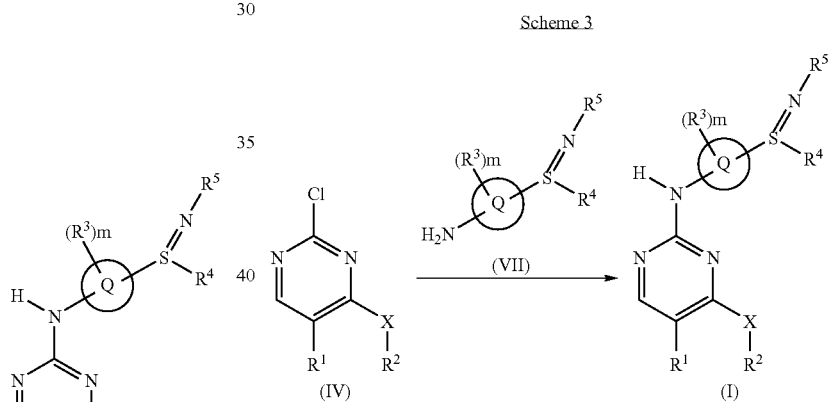

The substitutents Q, $R^1$, $R^2$, $R^3$, $R^4$, $R^5$, X and m have the meanings indicated in the general formula (I).

2-Chloropyrimidines of the formula (IV) can be reacted with nucleophiles of the formula (VII) to give products of the formula I. It is suitable for example to use isopropanol, acetonitrile or 1-butanol as solvent and optionally to add an acid such as, for example, hydrogen chloride.

Preparation of the Intermediates of the Formula (VII):

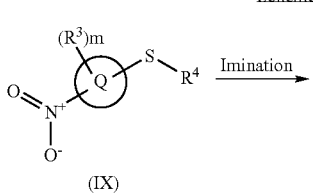

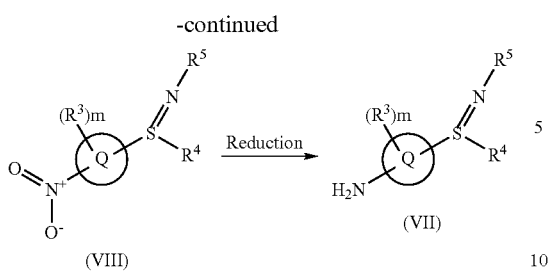

The substitutents Q, R³, R⁴, R⁵ and m have the meanings indicated in the general formula (I).

Thioethers of the formula (IX) can be converted into sulphimides of the formula (VIII) (for imination methods, see, for example: a) Johnson et al, *J Org: Chem.* 1979, 44, 2065; b) Oae et al, *Org. Chem. Sulfur* 1977, 383; c) Kucsman et al, *Phosphorous Sulfur* 1977, 3, 9; d) Sharpless et al, *J. Org. Chem.* 2001, 66, 594; e) Katsuki et al, *Tetrahedron Lett.* 2001, 42, 7071; f) Bolm et al, *Org. Lett.* 2004, 6, 1305; g) Carreira et al, *Helv. Chim. Acta* 2002, 85, 3773; h) Bolm et al, *Org. Lett.* 2006, 8, 2349; i) Bolm et al, *Org. Lett.* 2005, 7, 4983; Bolm et al., Org. Lett. 2006, 8, 2349)).

A number of methods are available for the subsequent reduction of the nitro group (see, for example: R. C. Larock, *Comprehensive Organic Transformations*, VCH, New York, 1989, 411-415). For example, the described hydrogenation using Raney nickel or the use of titanium(III) chloride in THF is suitable.

Alternatively, the intermediates of the formula (VII) can also be prepared by the following process (scheme 5):

Scheme 5

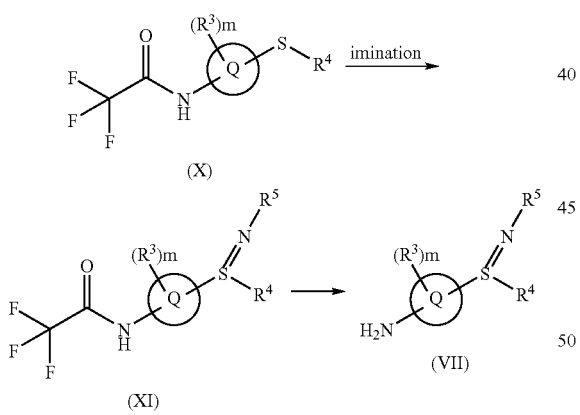

The substitutents Q, R³, R⁴, R⁵ and m have the meanings indicated in the general formula (I)

Thioethers of the formula (X) can be converted into sulphimides of the formula (XI) (for imination methods, see, for example: a) Johnson et al, *J Org: Chem.* 1979, 44, 2065; b) Oae et al, *Org. Chem. Sulfur* 1977, 383; c) Kucsman et al, *Phosphorous Sulfur* 1977, 3, 9; d) Sharpless et al, *J. Org. Chem.* 2001, 66, 594; e) Katsuki et al, *Tetrahedron Lett.* 2001, 42, 7071; f) Bolm et al, *Org. Lett.* 2004, 6, 1305; g) Carreira et al, *Helv. Chim. Acta* 2002, 85, 3773; h) Bolm et al, *Org. Lett.* 2006, 8, 2349; i) Bolm et al, *Org. Lett.* 2005, 7, 4983; Bolm et al, *Org. Lett.* 2006, 8, 2349)).

This is followed by elimination of the protective group to form the intermediates of the formula (VII). It is particularly suitable for example to use potassium carbonate in methanol, as described.

Process Variant 1

Examples 1-22

Example 1

(RS)—S-(4-{[5-Bromo-4-(isopropylamino)pyrimidin-2-yl]amino}phenyl)-S-methyl-N-(tolylsulphonyl)sulphimide

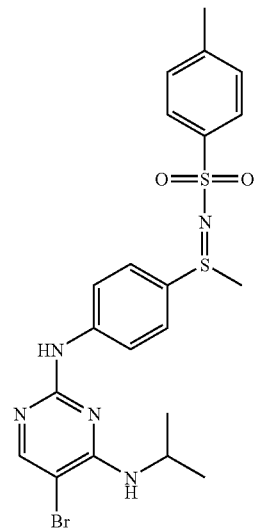

1a) Preparation of the Intermediates
Compound 1.1

(5-Bromo-2-chloropyrimidin-4-yl)isopropylamine

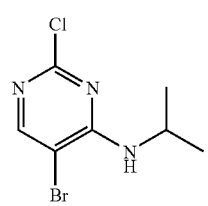

3.3 ml (23.8 mmol) of triethylamine and 2.0 ml (23.3 mmol) of 2-aminopropane are added to a solution of 4.87 g (21.4 mmol) of 5-bromo-2,4-dichloropyrimidine in 23 ml of acetonitrile at 0° C. The reaction mixture is stirred at room temperature overnight and then the solvent is stripped off. The resulting residue is purified by chromatography (dichloromethane/ethanol 8:2). 4.09 g (16.4 mmol; yield: 76%) of the product are obtained.

¹H-NMR (DMSO): 8.21 (s, 1H), 7.30 (d, 1H), 4.25 (m, 1H), 1.15 (d, 6H).

Compound 1.2

5-Bromo-N⁴-isopropyl-N²-(4-methylsulphanylphenyl)pyrimidine-2,4-diamine

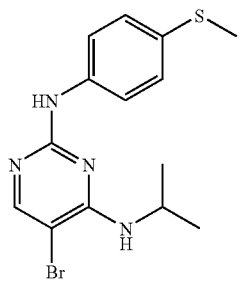

A solution of 2 ml (16.3 mmol) of 4-methylsulphanylphenylamine in 10 ml of acetonitrile is added to a solution of 4.08 g (16.3 mmol) of (5-bromo-2-chloropyrimidin-4-yl)isopropylamine in 20 ml of acetonitrile at room temperature. 4.1 ml of a 4 molar solution of hydrogen chloride in dioxane and 4.1 ml of water are added to the mixture, which is then stirred under reflux for 16 hours. After cooling, the precipitate which has formed is filtered off with suction, washed with water and dried. 4.94 g (12.7 mmol; yield: 78%) of the product are obtained in the form of the hydrochloride.

$^1$H-NMR (DMSO): 10.39 (s, 1H), 8.18 (s, 1H), 7.88 (br, 1H), 7.49 (m, 2H), 7.29 (m, 2H), 4.30 (m, 1H), 2.5 (s, 3H), 1.21 (d, 6H).

MS: 353 (ES).

1b) Preparation of the Final Product 1.36 g (4.8 mmol) of chloramine-T trihydrate (Aldrich) are added to a suspension of 1.56 g (4.0 mmol) of the hydrochloride of 5-bromo-N⁴-isopropyl-N²-(4-methyl-sulphanylphenyl)pyrimidine-2,4-diamine in 20 ml of acetonitrile at room temperature. The mixture is stirred at room temperature for 16 hours and then diluted with ethyl acetate. The mixture is filtered with suction and the filter cake is washed with ethyl acetate. The combined organic phases are dried (Na$_2$SO$_4$), filtered and concentrated. The resulting residue is purified by HPLC:

Column: Purospher Star C18 5µ

Length×ID: 125×25 mm

Eluents: A: H$_2$O+0.2% NH$_3$, B: MeCN

Flow rate: 25 ml/min

Gradient: 50% A+50% B(1')__50->64% B(10')->95% B(0.5')

Detector: UV 254 nm

Temperature: room temperature

RT in min: 7.8-8.

289 mg (0.55 mmol; yield: 14%) of the product are obtained.

$^1$H-NMR (DMSO): 9.64 (s, 1H), 8.08 (s, 1H), 7.88 (m, 2H), 7.59 (m, 2H), 7.51 (m, 2H), 7.19 (m, 2H), 6.58 (d, 1H), 4.30 (m, 1H), 2.87 (s, 3H), 2.28 (s, 3H), 1.22 (d, 6H). $^{13}$C-NMR (DMSO): 158.4 (s), 157.8 (s), 156.3 (d), 145.2 (s), 142.3 (s), 141.5 (s), 129.6 (d), 127.8 (d), 126.4 (s), 126.2 (d), 119.0 (d), 94.4 (s), 43.0 (d), 37.6 (q), 22.4 (q), 21.3 (q).

MS: 522 (ES+).

Example 2

(RS)—S-(3-{[5-Bromo-4-(isopropylamino)pyrimidin-2-yl]amino}phenyl)-S-methyl-N-(tolylsulphonyl)sulphimide

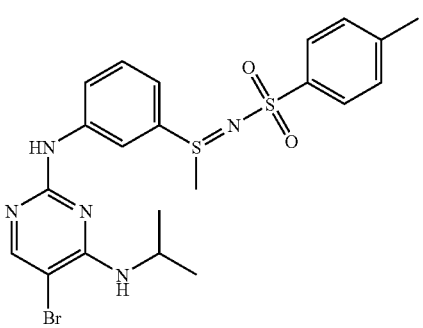

2a) Preparation of the Intermediate

Compound 2.1

5-Bromo-N⁴-isopropyl-N²-(3-methylsulphanylphenyl)pyrimidine-2,4-diamine

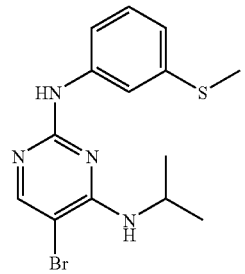

0.14 ml of a 4 molar solution of hydrogen chloride in dioxane and 0.17 ml of water are added to a solution of 0.152 g (0.61 mmol) of (5-bromo-2-chloropyrimidin-4-yl)-isopropylamine and 0.077 g (0.55 mmol) of 3-methylsulphanylphenylamine in 2 ml of acetonitrile, and the mixture is then stirred at 50° C. for 24 hours. After cooling, the mixture is added to saturated sodium bicarbonate solution. It is extracted with ethyl acetate. The combined organic phases are washed with saturated sodium chloride solution and dried over sodium sulphate. Removal of the solvent and recrystallization of the residue from ethyl acetate/hexane 9/1 result in 0.17 g (79% of theory) of the product.

$^1$H-NMR (300 MHz, DMSO): 9.20 (s, 1H), 7.99 (s, 1H), 7.77 (s, 1H), 7.37 (d, 1H), 7.14 (t, 1H), 6.75 (d, 1H), 6.47 (d, 1H), 4.34-4.27 (m, 1H), 2.40 (s, 3H), 1.21 (d, 6H).

2b) Preparation of the Final Product

In analogy to Example 1, 0.15 g (0.42 mmol) of 5-bromo-N⁴-isopropyl-N²-(3-methylsulphanylphenyl)pyrimidine-2,4-diamine is reacted with 0.132 g (0.47 mmol) of chloramine-T trihydrate in 3.0 ml of acetonitrile (24 hours). Purification by chromatography (silica gel, ethyl acetate/hexane with ethyl acetate 0-100%, then ethyl acetate/methanol with methanol 5-10% results in 0.14 g (63% of theory) of the product.

$^1$H-NMR (300 MHz, DMSO): 9.57 (s, 1H), 8.31 (s, 1H), 8.02 (s, 1H), 7.68 (d, 1H), 7.51 (d, 2H), 7.38 (t, 1H), 7.24 (d, 1H), 7.15 (d, 2H), 6.53 (d, 1H), 4.40-4.33 (m, 1H), 2.87 (s, 3H), 2.24 (s, 3H), 1.22-1.18 (m, 6H).

Example 3

(RS)—S-(4-{[5-Bromo-4-(cyclopropylamino)pyrimidin-2-yl]amino}phenyl)-S-methyl-N-(tolylsulphonyl)sulphimide

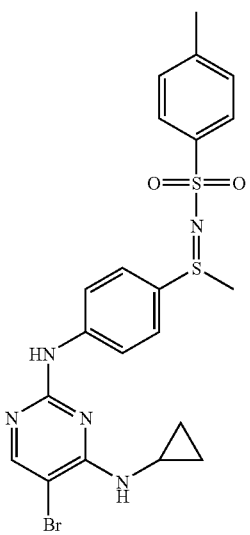

3a) Preparation of the Intermediates

Compound 3.1

(5-Bromo-2-chloropyrimidin-4-yl)cyclopropylamine

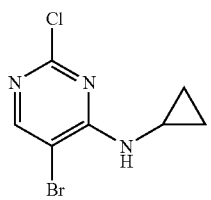

In analogy to compound 1.1, a solution of 1.0 g (4.39 mmol) of 5-bromo-2,4-dichloro-pyrimidine in 15 ml of acetonitrile is reacted with 0.27 g (4.74 mmol) of cyclopropylamine in the presence of 0.74 ml (5.3 mmol) of triethylamine. Purification by chromatography (silica gel, ethyl acetate/hexane with ethyl acetate 0-100%) results in 0.76 g (70% of theory) of the product.

$^1$H-NMR (300 MHz, DMSO): 8.21 (s, 1H), 7.70 (br, 1H), 2.81-2.74 (m, 1H), 0.74-0.59 (m, 4H).

Compound 3.2

5-Bromo-N$^4$-cyclopropyl-N$^2$-(4-methylsulphanylphenyl)pyrimidine-2,4-diamine

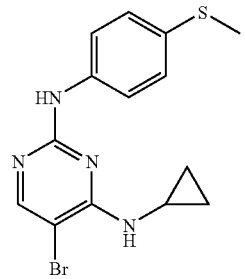

In analogy to compound 2.1, 0.2 g (0.8 mmol) of (5-bromo-2-chloropyrimidin-4-yl)-cyclopropylamine is reacted with 0.102 g (0.73 mmol) of 4-methylsulphanyl-phenylamine in 3 ml of acetonitrile in the presence of 0.18 ml of a 4 molar solution of hydrogen chloride in dioxane, and 0.23 ml of water. 0.25 g (88% of theory) of the product is obtained.

$^1$H-NMR (400 MHz, DMSO): 9.28 (s, 1H), 7.97 (s, 1H), 7.80 (d, 2H), 7.16 (d, 2H), 7.01 (br, 1H), 2.78-2.75 (m, 1H), 2.38 (s, 3H), 0.78-0.76 (m, 2H), 0.62-0.59 (m, 2H).

3b) Preparation of the Final Product

In analogy to Example 1, 0.21 g (0.6 mmol) of 5-bromo-N$^4$-cyclopropyl-N$^2$-(4-methylsulphanylphenyl)pyrimidine-2,4-diamine is reacted with 0.185 g (0.66 mmol) of chloramine-T trihydrate in 5.0 ml of acetonitrile (24 hours). The mixture is diluted with ethyl acetate. The resulting precipitate is filtered off with suction and washed with ethyl acetate. The filtrate is concentrated and the residue is chromatographed (dichloromethane/methanol with methanol 0-15%). 0.23 g (74%) of the product is obtained.

$^1$H-NMR (400 MHz, DMSO): 9.75 (s, 1H), 8.04 (s, 1H), 8.01 (d, 2H), 7.59 (d, 2H), 7.52 (d, 2H), 7.20-7.18 (m, 3H), 2.87 (s, 3H), 2.79-2.74 (m, 1H), 2.27 (s, 3H), 0.80-0.75 (m, 2H), 0.66-0.62 (m, 2H).

Example 4

(RS)—S-(3-{[5-Bromo-4-(cyclopropylamino)pyrimidin-2-yl]amino}phenyl)-S-methyl-N-(tolylsulphonyl)sulphimide

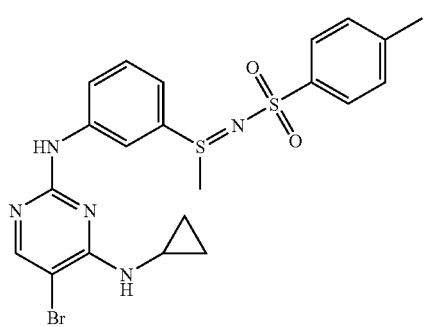

4a) Preparation of the Intermediate
Compound 4.1

5-Bromo-$N^4$-cyclopropyl-$N^2$-(3-methylsulphanylphenyl)pyrimidine-2,4-diamine

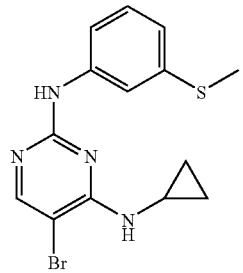

In analogy to compound 2.1, 0.58 g (2.33 mmol) of (5-bromo-2-chloropyrimidin-4-yl)-cyclopropylamine is reacted with 0.296 g (2.12 mmol) of 3-methylsulphanyl-phenylamine in 7.0 ml of acetonitrile in the presence of 0.53 mol of a 4 molar solution of hydrogen chloride in dioxane, and 0.67 ml of water. 0.6 g (73% of theory) of the product is obtained.

$^1$H-NMR (300 MHz, DMSO): 9.28 (s, 1H), 7.99 (s, 1H), 7.94 (s, 1H), 7.51 (dd, 1H), 7.15 (t, 1H), 7.05 (d, 1H), 6.75 (d, 1H), 2.79-2.75 (m, 1H), 2.39 (s, 3H), 0.83-0.79 (m, 2H), 0.64-0.60 (m, 2H).

4b) Preparation of the Final Product

In analogy to Example 1, 0.19 g (0.54 mmol) of 5-bromo-$N^4$-cyclopropyl-$N^2$-(3-methylsulphanylphenyl)pyrimidine-2,4-diamine is reacted with 0.168 g (0.59 mmol) of chloramine-T trihydrate in 5.0 ml of acetonitrile (24 hours). Purification by chromatography (silica gel, ethyl acetate/hexane with ethyl acetate 0-100%, then ethyl acetate/methanol with methanol 5-10%) results in 0.13 g (47% of theory) of the product.

$^1$H-NMR (400 MHz, DMSO): 9.65 (s, 1H), 8.48 (s, 1H), 8.03 (s, 1H), 7.78 (d, 1H), 7.50 (d, 2H), 7.40 (t, 1H), 7.25 (d, 1H), 7.16 (d, 2H), 7.12 (d, 1H), 2.94-2.92 (m, 1H), 2.86 (s, 3H), 2.25 (s, 3H), 0.82-0.79 (m, 2H), 0.67-0.55 (m, 2H).

Example 5

(RS)—S-(4-{[4-(Isopropylamino)pyrimidin-2-yl]amino}phenyl)-S-methyl-N-(tolylsulphonyl)sulphimide

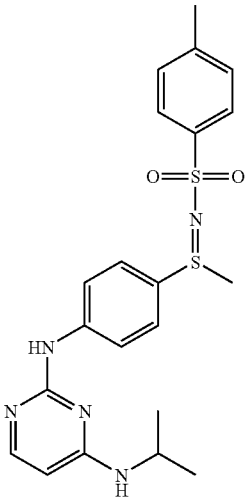

5a) Preparation of the Intermediates

Compound 5.1

(2-Chloropyrimidin-4-yl)isopropylamine

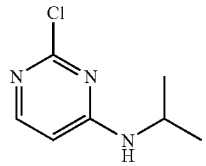

In analogy to compound 1.1, a solution of 0.347 g (2.33 mmol) of 2,4-dichloro-pyrimidine in 15 ml of acetonitrile is reacted with 0.22 ml (2.52 mmol) of isopropylamine in the presence of 0.39 ml (2.83 mmol) of triethylamine. Purification by chromatography (silica gel, ethyl acetate/hexane with ethyl acetate 0-100%) results in 0.26 g (65% of theory) of the product.

$^1$H-NMR (300 MHz, DMSO): 7.81 (br, 2H), 6.35 (br, 1H), 4.00 (br, 1H), 1.09 (d, 6H).

Compound 5.2

$N^4$-Isopropyl-$N^2$-(4-methylsulphanylphenyl)pyrimidine-2,4-diamine

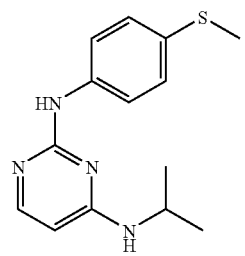

In analogy to compound 2.1, 0.26 g (1.51 mmol) of (2-chloropyrimidin-4-yl)isopropyl-amine is reacted with 0.192 g (1.38 mmol) of 4-methylsulphanylphenylamine in 5 ml of acetonitrile in the presence of 0.34 ml of a 4 molar solution of hydrogen chloride in dioxane, and 0.43 ml of water. 0.31 g (75% of theory) of the product is obtained.

$^1$H-NMR (400 MHz, DMSO): 8.89 (s, 1H), 7.72-7.70 (m, 3H), 7.13 (d, 2H), 6.98 (br, 1H), 5.85 (d, 1H), 4.07 (br, 1H), 2.38 (s, 3H), 1.13 (d, 6H).

5b) Preparation of the Final Product

In analogy to Example 1, 0.28 g (1.02 mmol) of $N^4$-isopropyl-$N^2$-(4-methylsulphanyl-phenyl)pyrimidine-2,4-diamine is reacted with 0.316 g (1.12 mmol) of chloramine-T trihydrate in 9.0 ml of acetonitrile (24 hours). Purification by chromatography (silica gel, ethyl acetate/hexane with ethyl acetate 0-100%, then ethyl acetate/methanol with methanol 5-10%) results in 0.26 g (58% of theory) of the product.

¹H-NMR (300 MHz, DMSO): 9.39 (s, 1H), 7.93 (d, 2H), 7.78 (d, 1H), 7.57-7.50 (m, 4H), 7.21-7.10 (m, 3H), 5.94 (d, 1H), 4.25-3.95 (br, 1H), 2.86 (s, 3H), 2.27 (s, 3H), 1.16-1.14 (m, 6H).

Example 6

(RS)—S-{4-[(4-Anilino-5-bromopyrimidin-2-yl)amino]phenyl}-S-methyl-N-(tolylsulphonyl)sulphimide

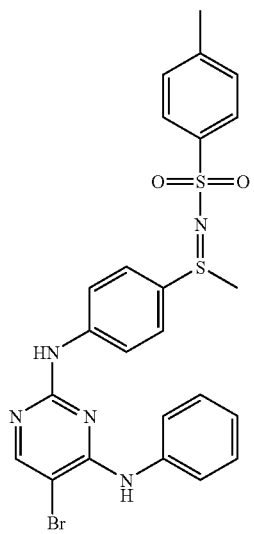

6a) Preparation of the Intermediates

Compound 6.1

(5-Bromo-2-chloropyrimidin-4-yl)phenylamine

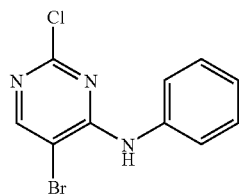

In analogy to compound 1.1, a solution of 0.3 g (1.32 mmol) of 5-bromo-2,4-dichloro-pyrimidine in 5 ml of acetonitrile is reacted with 0.13 ml (1.42 mmol) of aniline in the presence of 0.22 ml (1.6 mmol) of triethylamine. Purification by chromatography (silica gel, ethyl acetate/hexane with ethyl acetate 0-100%) results in 0.289 g (77% of theory) of the product.

¹H-NMR (400 MHz, DMSO): 9.26 (s, 1H), 8.42 (s, 1H), 7.50 (d, 2H), 7.36 (t, 2H), 7.16 (t, 1H).

Compound 6.2

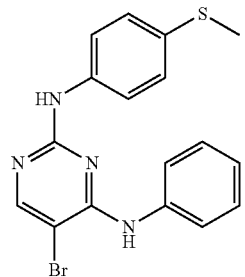

In analogy to compound 2.1, 0.286 g (1.0 mmol) of (5-bromo-2-chloropyrimidin-4-yl)-phenylamine is reacted with 0.127 g (0.91 mmol) of 4-methylsulphanylphenylamine in 3.0 ml of acetonitrile in the presence of 0.23 ml of a 4 molar solution of hydrogen chloride in dioxane, and 0.29 ml of water. Recrystallization from ethyl acetate results in 0.248 g (64% of theory) of the product.

¹H-NMR (400 MHz, DMSO): 9.33 (s, 1H), 8.59 (s, 1H), 8.18 (s, 1H), 7.59-7.51 (m, 4H), 7.34 (t, 2H), 7.14 (t, 1H), 7.05 (d, 2H), 2.37 (s, 3H).

6b) Preparation of the Final Product

In analogy to Example 1, 0.232 g (0.6 mmol) of 5-bromo-$N^2$-(4-methylsulphanyl-phenyl)-$N^4$-phenylpyrimidine-2,4-diamine is reacted with 0.186 g (0.66 mmol) of chloramine-T trihydrate in 5.0 ml of acetonitrile (24 hours). Purification by chromatography (silica gel, ethyl acetate/hexane with ethyl acetate 0-100%, then ethyl acetate/methanol with methanol 5-10%) results in 0.179 g (54% of theory) of the product.

¹H-NMR (400 MHz, DMSO): 9.76 (s, 1H), 8.76 (s, 1H), 8.22 (s, 1H), 7.71 (d, 2H), 7.54 (d, 2H), 7.50 (d, 2H), 7.45 (d, 2H), 7.37 (t, 2H), 7.20-7.17 (m, 3H), 2.86 (s, 3H), 2.26 (s, 3H).

Example 7

(RS)—S-[4-({5-Bromo-4-[(2-hydroxyethyl)amino]pyrimidin-2-yl}amino)phenyl]-S-methyl-N-(tolylsulphonyl)sulphimide

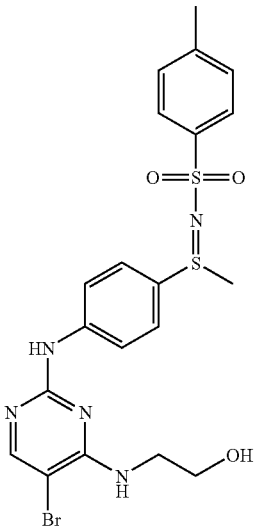

7a) Preparation of the Intermediates

Compound 7.1

2-(5-Bromo-2-chloropyrimidin-4-ylamino)ethanol

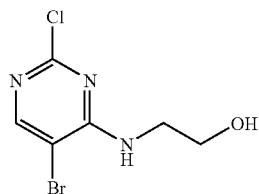

In analogy to compound 1.1, a solution of 0.34 g (1.49 mmol) of 5-bromo-2,4-dichloropyrimidine in 5 ml of acetonitrile is reacted with 0.1 ml (1.61 mmol) of ethanolamine in the presence of 0.25 ml (1.81 mmol) of triethylamine. Recrystallization from hexane/ethyl acetate 7/3 results in 0.28 g (74% of theory) of the product.

$^1$H-NMR (300 MHz, DMSO): 8.20 (s, 1H), 7.52 (t, 1H), 4.77 (t, 1H), 3.52-3.33 (m, 4H).

Compound 7.2

2-[5-Bromo-2-(4-methylsulphanylphenylamino)pyrimidin-4-ylamino]ethanol

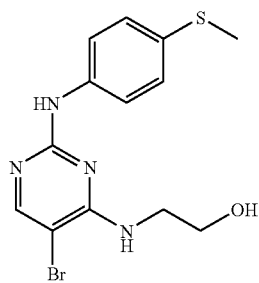

In analogy to compound 2.1, 0.28 g (1.11 mmol) of 2-(5-bromo-2-chloropyrimidin-4-ylamino)ethanol is reacted with 0.14 g (1.01 mmol) of 4-methylsulphanylphenylamine in 4 ml of acetonitrile in the presence of 0.25 ml of a 4 molar solution of hydrogen chloride in dioxane, and 0.32 ml of water. 0.31 g (79% of theory) of the product is obtained.

$^1$H-NMR (400 MHz, DMSO): 9.21 (s, 1H), 7.97 (s, 1H), 7.65 (d, 2H), 7.15 (d, 2H), 6.74 (t, 1H), 4.75 (t, 1H), 3.57-3.53 (m, 2H), 3.47-3.42 (m, 2H), 2.38 (s, 3H).

7b) Preparation of the Final Product:

In analogy to Example 1, 0.28 g (0.79 mmol) of 2-[5-bromo-2-(4-methylsulphanyl-phenylamino)pyrimidin-4-ylamino]ethanol is reacted with 0.244 g (0.87 mmol) of chloramine-T trihydrate in 7.0 ml of acetonitrile (24 hours). Purification by chromatography (silica gel, ethyl acetate/hexane with ethyl acetate 0-100%, then ethyl acetate/methanol with methanol 5-20%) results in 0.25 g (61% of theory) of the product.

$^1$H-NMR (400 MHz, DMSO): 9.67 (s, 1H), 8.05 (s, 1H), 7.87 (d, 2H), 7.59 (d, 2H), 7.52 (d, 2H), 7.20 (d, 2H), 6.90 (t, 1H), 4.79 (t, 1H), 3.59-3.55 (m, 2H), 3.48-3.45 (m, 2H), 2.87 (s, 3H), 2.27 (s, 3H).

Example 8

(RS)—S-{4-[(5-Bromo-4-{[(R)-2-hydroxy-1-methylethyl]amino}pyrimidin-2-yl)-amino]phenyl}-S-methyl-N-(tolylsulphonyl)sulphimide

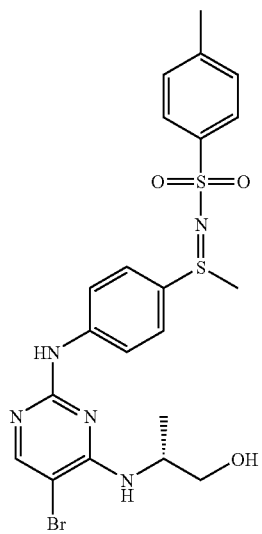

8a) Preparation of the Intermediate

Compound 8.1

(R)-2-[5-Bromo-2-(4-methylsulphanylphenylamino)pyrimidin-4-ylamino]propan-1-ol

In analogy to compound 2.1, 0.27 g (1.01 mmol) of (R)-2-[(5-bromo-2-chloro-pyrimidin-4-yl)amino]propan-1-ol (cf. WO2005037800) is reacted with 0.128 g (0.92 mmol) of 4-methylsulphanylphenylamine in 4 ml of acetonitrile in the presence of 0.23 ml of a 4 molar solution of hydrogen chloride in dioxane, and 0.29 ml of water. 0.25 g (67% of theory) of the product is obtained.

$^1$H-NMR (300 MHz, DMSO): 9.21 (s, 1H), 7.98 (s, 1H), 7.65 (d, 2H), 7.15 (d, 2H), 6.23 (d, 1H), 4.84 (t, 1H), 4.22-4.15 (m, 1H), 3.52-3.44 (m, 2H), 2.38 (s, 3H), 1.15 (d, 3H).

8b) Preparation of the Final Product:

In analogy to Example 1, 0.24 g (0.65 mmol) of (R)-2-[5-bromo-2-(4-methylsulphanyl-phenylamino) pyrimidin-4-ylamino]propan-1-ol is reacted with 0.202 g (0.71 mmol) of chloramine-T trihydrate in 6.0 ml of acetonitrile (24 hours). Purification by chromatography (ethyl acetate/methanol with methanol 10-25%) results in 0.247 g (71% of theory) of the product.

$^1$H-NMR (400 MHz, DMSO): 9.67 (s, 1H), 8.06 (s, 1H), 7.86 (d, 2H), 7.59 (d, 2H), 7.52 (d, 2H), 7.20 (d, 2H), 6.39 (d, 1H), 4.87 (t, 1H), 4.23-4.17 (m, 1H), 3.52-3.43 (m, 2H), 2.87 (s, 3H), 2.27 (s, 3H), 1.17 (d, 3H).

Example 9

(RS)—S-{4-[(5-Bromo-4-{[(R)-2-hydroxy-1,2-dimethylpropyl]amino}pyrimidin-2-yl)amino]phenyl}-S-methyl-N-(tolylsulphonyl)sulphimide

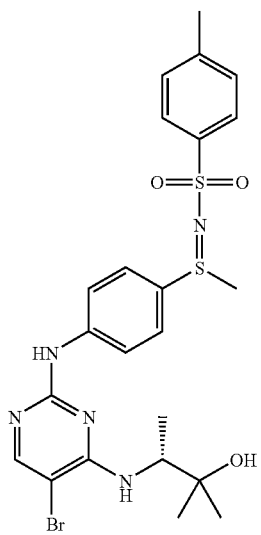

9a) Preparation of the Intermediate

Compound 9.1

(R)-3-[{5-Bromo-2-(4-methylsulphanylphenylamino)pyrimidin-4-yl)}amino]-2-methylbutan-2-ol

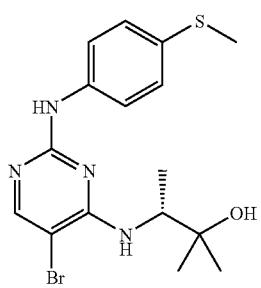

In analogy to compound 2.1, 0.3 g (1.02 mmol) of (R)-3-[(5-bromo-2-chloropyrimidin-4-yl)amino]-2-methylbutan-2-ol (cf. WO2005037800) is reacted with 0.129 g (0.93 mmol) of 4-methylsulphanylphenylamine in 3 ml of acetonitrile in the presence of 0.23 ml of a 4 molar solution of hydrogen chloride in dioxane, and 0.29 ml of water. Purification by chromatography (silica gel, ethyl acetate/hexane with ethyl acetate 0-100%) results in 0.29 g (72% of theory) of the product.

$^1$H-NMR (300 MHz, DMSO): 9.22 (s, 1H), 8.00 (s, 1H), 7.64 (d, 2H), 7.15 (d, 2H), 5.95 (d, 1H), 4.78 (s, 1H), 4.07-3.98 (m, 1H), 2.39 (s, 3H), 1.16-1.08 (m, 9H).

9b) Preparation of the Final Product

In analogy to Example 1, 0.28 g (0.7 mmol) of (R)-3-[{5-bromo-2-(4-methylsulphanyl-phenylamino) pyrimidin-4-yl)}amino]-2-methylbutan-2-ol is reacted with 0.218 g (0.78 mmol) of chloramine-T trihydrate in 6.0 ml of acetonitrile (24 hours). Purification by chromatography (silica gel, ethyl acetate/hexane with ethyl acetate 0-100%, then ethyl acetate/methanol with methanol 5-10%) results in 0.21 g (53% of theory) of the product.

$^1$H-NMR (400 MHz, DMSO): 9.68 (s, 1H), 8.08 (s, 1H), 7.86 (d, 2H), 7.60 (d, 2H), 7.52 (d, 2H), 7.19 (d, 2H), 6.07 (d, 1H), 4.83 (s, 1H), 4.07-4.01 (m, 1H), 2.87 (s, 3H), 2.27 (s, 3H), 1.16-1.14 (m, 6H), 1.10 (s, 3H).

Example 10

(RS)—S-{4-[(5-Bromo-4-{[(R)-2-hydroxy-1,2-dimethylpropyl]amino}pyrimidin-2-yl)amino]phenyl}-S-methyl-N-[(5-methyl-2-pyridyl)sulphonyl]sulphimide

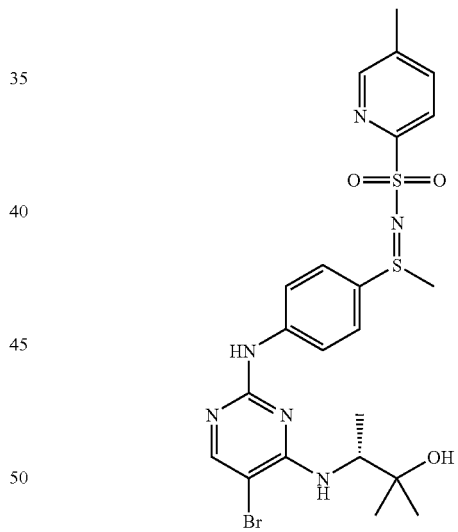

10a) Preparation of the Intermediate

The intermediate is compound 9.1.

10b) Preparation of the Final Product 300 mg (0.76 mmol) of (R)-3-[{5-bromo-2-(4-methylsulphanylphenylamino) pyrimidin-4-yl)}amino]-2-methylbutan-2-ol (compound 9.1), 192 mg (1.12 mmol) of 5-methylpyridine-2-sulphonamide, 265 mg (1.21 mmol) of iodosobenzene and 266 mg (0.76 mmol) of iron(III)acetylacetonate are weighed into a flask, and 8 ml of aceto-nitrile are added. The mixture is stirred at room temperature for 62 hours and then concentrated in a rotary evaporator. The remaining residue is purified by chromatography (dichloromethane/ethanol 8:2). 100 mg (0.18 mmol; yield: 23%) of the product are obtained.

Alternatively, the final product can be prepared in the following way: 300 mg (0.76 mmol) of (R)-3-[{5-bromo-2-(4-methylsulphanylphenylamino) pyrimidin-4-yl)}amino]-2-methylbutan-2-ol (compound 9.1), 260 mg (1.51 mmol) of 5-methyl-pyridine-2-sulphonamide, 121 mg (3.00 mmol) of magnesium oxide, 374 mg (1.16 mmol) of iodobenzene diacetate and 33 mg (0.08 mmol) of rhodium(II) acetate dimer are weighed into a flask, and 10 ml of dichloromethane are added. The mixture is stirred at room temperature for 19 hours and then concentrated in a rotary evaporator. The remaining residue is purified by chromatography (dichloromethane/ethanol 9:1). 42 mg (0.08 mmol; yield: 10%) of the product are obtained.

$^1$H-NMR (400 MHz, DMSO): 9.70 (s, 1H), 8.37 (br, 1H), 8.09 (s, 1H), 7.91 (m, 2H), 7.69 (m, 4H), 6.06 (d, 1H), 4.83 (s, 1H), 4.04 (m, 1H), 2.98 (s, 3H), 2.29 (s, 3H), 1.12 (m, 9H).

MS: 567 (ES+)

Example 11

(RS)—S-{4-[(5-Bromo-4-{[(R)-2-hydroxy-1,2-dimethylpropyl]amino}pyrimidin-2-yl)amino]phenyl}-N-[(4-chloro-3-pyridyl)sulphonyl]-S-methylsulphimide

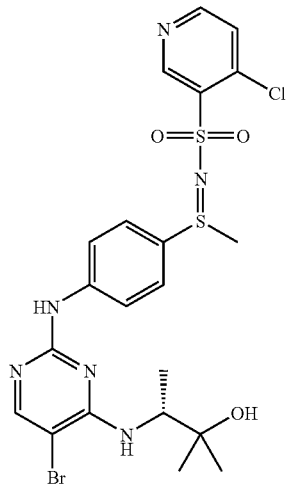

Preparation of the Final Product 285 mg (0.76 mmol) of (R)-3-[{5-bromo-2-(4-methylsulphanylphenylamino) pyrimidin-4-yl)}amino]-2-methylbutan-2-ol (compound 9.1), 207 mg (1.08 mmol) of 4-chloropyridine-3-sulphonamide, 252 mg (1.15 mmol) of iodosobenzene and 253 mg (0.76 mmol) of iron(III)acetylacetonate are weighed into a flask, and 8 ml of aceto-nitrile are added. The mixture is stirred at room temperature for 144 hours and then concentrated in a rotary evaporator. The remaining residue is purified by chromatography (dichloromethane/ethanol 8:2). 38 mg (0.07 mmol; yield 9%) of the product are obtained.

$^1$H-NMR (DMSO): 9.70 (s, 1H), 8.86 (m, 1H), 8.53 (m, 1H), 8.09 (s, 1H), 7.84 (m, 2H), 7.63 (m, 2H), 7.54 (m, 1H), 6.07 (d, 1H), 4.83 (s, 1H), 4.04 (m, 1H), 3.00 (s, 3H), 1.12 (m, 9H)

MS: 587 (ES+).

Example 12

(RS)—S-{4-[(5-Bromo-4-{[(R)-2-hydroxy-1,2-dimethylpropyl]amino}pyrimidin-2-yl)amino]phenyl}-N-[(4-methoxyphenyl)sulphonyl]-S-methylsulphimide

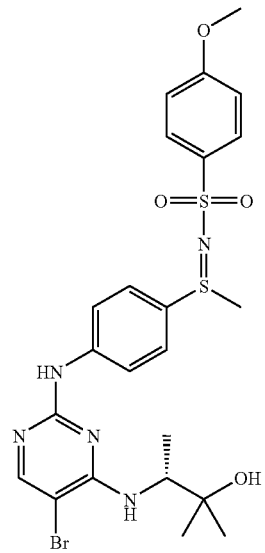

Preparation of the Final Product 287 mg (0.76 mmol) of (R)-3-[{5-bromo-2-(4-methylsulphanylphenylamino) pyrimidin-4-yl)}amino]-2-methylbutan-2-ol (compound 9.1), 202 mg (1.08 mmol) of 4-methoxybenzenesulphonamide, 254 mg (1.16 mmol) of iodosobenzene and 255 mg (0.72 mmol) of iron(III)acetylacetonate are weighed into a flask, and 8 ml of aceto-nitrile are added. The mixture is stirred at room temperature for 90 hours and then concentrated in a rotary evaporator. The remaining residue is purified by chromatography (dichloromethane/ethanol 8:2). 23 mg (0.04 mmol; yield: 6%) of the product are obtained.

$^1$H-NMR (DMSO): 9.69 (s, 1H), 8.08 (s, 1H), 7.87 (m, 2H), 7.59 (m, 4H), 6.92 (m, 2H), 6.07 (d, 1H), 4.84 (s, 1H), 4.03 (m, 1H), 3.72 (s, 3H), 2.87 (s, 3H), 1.12 (m, 9H).

MS: 582 (ES+).

Example 13

(RS)—N—(Benzylsulphonyl)-S-{4-[(5-bromo-4-{[(R)-2-hydroxy-1,2-dimethylpropyl]-amino}pyrimidin-2-yl)amino]phenyl}-S-methylsulphimide

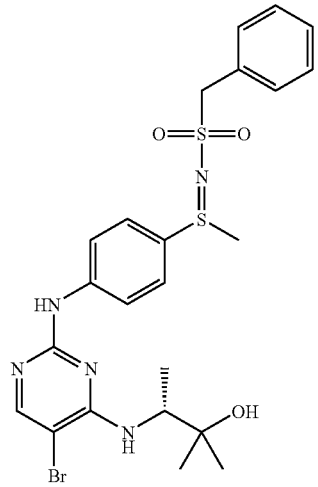

Preparation of the Final Product 287 mg (0.72 mmol) of (R)-3-[{5-bromo-2-(4-methylsulphanylphenylamino) pyrimidin-4-yl)}amino]-2-methylbutan-2-ol (compound 9.1), 185 mg (1.08 mmol) of phenylmethanesulphonamide, 254 mg (1.16 mmol) of iodosobenzene and 255 mg (0.72 mmol) of iron(III)acetylacetonate are weighed into a flask, and 8 ml of aceto-nitrile are added. The mixture is stirred at room temperature for 142 hours and then concentrated in a rotary evaporator. The remaining residue is purified by chromatography (dichloromethane/ethanol 8:2). 54 mg (0.10 mmol; yield: 13%) of the product are obtained.

$^1$H-NMR (DMSO): 9.69 (s, 1H), 8.08 (s, 1H), 7.90 (m, 2H), 7.62 (m, 2H), 7.26 (m, 5H), 6.07 (d, 1H), 4.82 (s, 1H), 4.13 (s, 2H), 4.03 (m, 1H), 2.77 (s, 3H), 1.12 (m, 9H).

MS: 566 (ES+).

Example 14

(RS)—S-{4-[(5-Bromo-4-{[(R)-2-hydroxy-1,2-dimethylpropyl]amino}pyrimidin-2-yl)amino]phenyl}-S-methyl-N-[(trifluoromethyl)sulphonyl]sulphimide

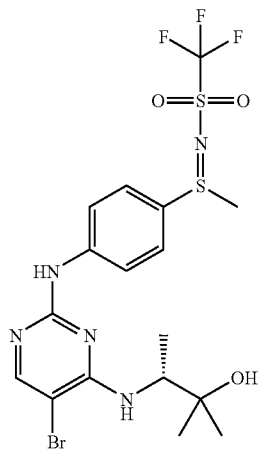

Preparation of the Final Product 294 mg (0.74 mmol) of (R)-3-[{5-bromo-2-(4-methylsulphanylphenylamino) pyrimidin-4-yl)}amino]-2-methylbutan-2-ol (compound 9.1), 165 mg (1.11 mmol) of trifluoromethylsulphonamide, 260 mg (1.18 mmol) of iodosobenzene and 261 mg (0.74 mmol) of iron(III)acetylacetonate are weighed into a flask, and 8 ml of aceto-nitrile are added. The mixture is stirred at room temperature for 142 hours and then concentrated in a rotary evaporator. The remaining residue is purified by chromatography (dichloromethane/ethanol 8:2). 12 mg (0.02 mmol; yield: 3%) of the product are obtained.

Alternatively, the final product can be prepared in the following way: 200 mg (0.50 mmol) of (R)-3-[{5-bromo-2-(4-methylsulphanylphenylamino) pyrimidin-4-yl)}amino]-2-methylbutan-2-ol (compound 9.1) and 150 mg (1.01 mmol) of trifluoromethylsulphonamide are mixed with 7.2 ml of dichloromethane. 101 mg (2.52 mmol) of magnesium oxide, 22 mg (0.05 mmol) of rhodium(II)acetate dimer and 324 mg (1.01 mmol) of iodobenzene diacetate are added to the mixture. The mixture is stirred at room temperature for 2 hours and then concentrated in a rotary evaporator. The remaining residue is initially purified by chromatography (dichloromethane/ethanol 9:1). 28 mg (0.05 mmol; yield: 10%) of the product are obtained.

$^1$H-NMR (DMSO): 9.81 (s, 1H), 8.11 (s, 1H), 7.97 (m, 2H), 7.82 (m, 2H), 6.09 (d, 1H), 4.62 (br, 1H), 4.05 (m, 1H), 3.17 (s, 3H), 1.12 (m, 9H).

MS: 544 (ES+).

Example 15

(RS)—S-{4-[(5-Bromo-4-{[(R)-2-hydroxy-1,2-dimethylpropyl]amino}pyrimidin-2-yl)amino]phenyl}-S-methyl-N-(phenylsulphonyl)sulphimide

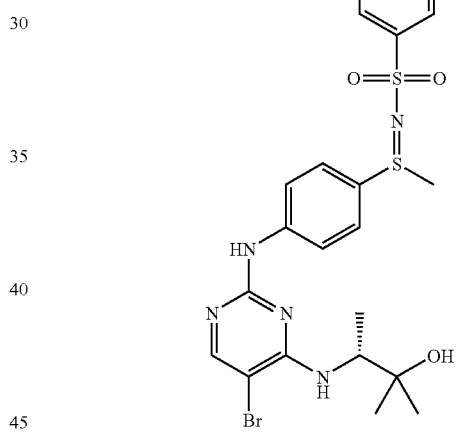

Preparation of the Final Product 294 mg (0.74 mmol) of (R)-3-[{5-bromo-2-(4-methylsulphanylphenylamino) pyrimidin-4-yl)}amino]-2-methylbutan-2-ol (compound 9.1), 174 mg (1.08 mmol) of phenylsulphonamide, 260 mg (1.18 mmol) of iodosobenzene and 261 mg (0.74 mmol) of iron(III)acetylacetonate are weighed into a flask, and 8 ml of acetonitrile are added. The mixture is stirred at room temperature for 91 hours and then concentrated in a rotary evaporator. The remaining residue is purified by chromatography (dichloromethane/ethanol 8:2). 64 mg (0.12 mmol; yield: 16%) of the product are obtained.

$^1$H-NMR (DMSO): 9.68 (s, 1H), 8.08 (s, 1H), 7.88 (m, 2H), 7.61 (m, 4H), 7.41 (m, 3H), 6.06 (d, 1H), 4.82 (s, 1H), 4.03 (m, 1H), 2.89 (s, 3H), 1.11 (m, 9H).

MS: 552 (ES+).

Example 16

(RS)—S-{4-[(5-Bromo-4-{[(R)-2-hydroxy-1,2-dimethylpropyl]-amino}pyrimidin-2-yl)amino]phenyl}-S-methyl-N-{[4-(trifluoromethoxy)phenyl]-sulphonyl}sulphimide

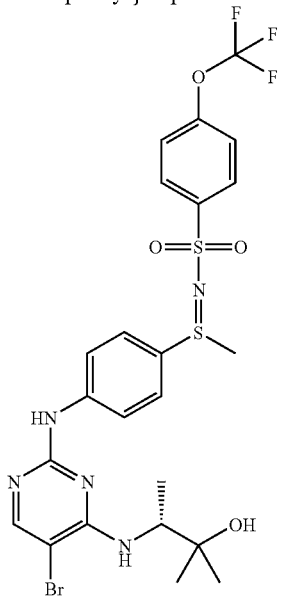

Preparation of the Final Product 246 mg (0.62 mmol) of (R)-3-[{5-bromo-2-(4-methylsulphanylphenylamino) pyrimidin-4-yl)}amino]-2-methylbutan-2-ol (compound 9.1), 224 mg (0.93 mmol) of 4-trifluoromethoxybenzenesulphonamide, 217 mg (1.00 mmol) of iodosobenzene and 218 mg (0.62 mmol) of iron(III)acetylacetonate are weighed into a flask, and 7 ml of acetonitrile are added. The mixture is stirred at room temperature for 91 hours and then concentrated in a rotary evaporator. The remaining residue is purified by chromatography (dichloromethane/ethanol 8:2). 27 mg (0.12 mmol; yield: 7%) of the product are obtained.

$^1$H-NMR (DMSO): 9.73 (s, 1H), 8.13 (s, 1H), 7.89 (m, 2H), 7.78 (m, 2H), 7.63 (m, 2H), 7.39 (m, 2H), 6.11 (d, 1H), 4.87 (s, 1H), 4.07 (m, 1H), 2.99 (s, 3H), 1.11 (m, 9H).

MS: 636 (ES+).

Example 17

(RS)—S-{4-[(5-Bromo-4-{[(R)-2-hydroxy-1,2-dimethylpropyl]amino}pyrimidin-2-yl)amino]phenyl}-N-[(5-chloro-2-thienyl)sulphonyl]-S-methylsulphimide

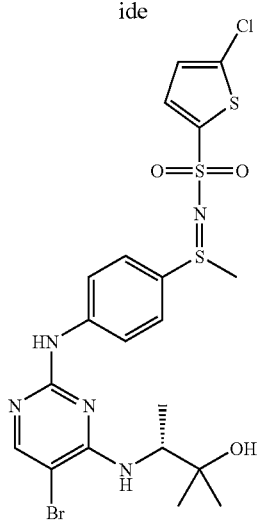

Preparation of the Final Product 246 mg (0.62 mmol) of (R)-3-[{5-bromo-2-(4-methylsulphanylphenylamino) pyrimidin-4-yl)}amino]-2-methylbutan-2-ol (compound 9.1), 184 mg (0.93 mmol) of 5-chlorothiophen-2-sulphonamide, 218 mg (1.00 mmol) of iodosobenzene and 218 mg (0.62 mmol) of iron(III)acetylacetonate are weighed into a flask, and 7 ml of aceto-nitrile are added. The mixture is stirred at room temperature for 91 hours and then concentrated in a rotary evaporator. The remaining residue is purified by chromatography (dichloromethane/ethanol 8:2). 1 mg (0.02 mmol; yield: 3%) of the product are obtained.

$^1$H-NMR (DMSO): 9.73 (s, 1H), 8.09 (s, 1H), 7.91 (m, 2H), 7.67 (m, 2H), 7.18 (m, 1H), 7.01 (m, 1H), 6.07 (d, 1H), 4.83 (s, 1H), 4.04 (m, 1H), 2.99 (s, 3H), 1.11 (m, 9H).

MS: 592 (ES+).

Example 18

(RS)—S-{4-[(5-Bromo-4-{[(R)-2-hydroxy-1,2-dimethylpropyl]amino}pyrimidin-2-yl)amino]phenyl}-N-mesyl-S-methylsulphimide

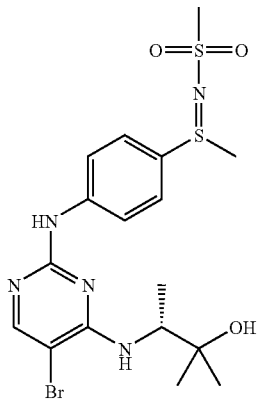

Preparation of the Final Product 287 mg (0.72 mmol) of (R)-3-[{5-bromo-2-(4-methylsulphanylphenylamino) pyrimidin-4-yl)}amino]-2-methylbutan-2-ol (compound 9.1), 103 mg (1.08 mmol) of methylsulphonamide, 254 mg (1.16 mmol) of iodosobenzene and 255 mg (0.72 mmol) of iron(III)acetylacetonate are weighed into a flask, and 8 ml of acetonitrile are added. The mixture is stirred at room temperature for 88 hours and then concentrated in a rotary evaporator. The remaining residue is purified by chromatography (dichloromethane/ethanol 8:2). 12 mg (0.03 mmol; yield: 3%) of the product are obtained.

$^1$H-NMR (DMSO): 9.70 (s, 1H), 8.08 (s, 1H), 7.94 (m, 2H), 7.73 (m, 2H), 6.07 (d, 1H), 4.82 (s, 1H), 4.05 (m, 1H), 2.95 (s, 3H), 2.71 (s, 3H), 1.11 (m, 9H).

MS: 490 (ES+).

Example 19

(RS)—N-{[5-(Acetylamino)-1,3,4-thiadiazol-2-yl]sulphonyl}-S-{4-[(5-bromo-4-{[(R)-2-hydroxy-1,2-dimethylpropyl]amino}pyrimidin-2-yl)amino]phenyl}-S-methyl-sulphimide

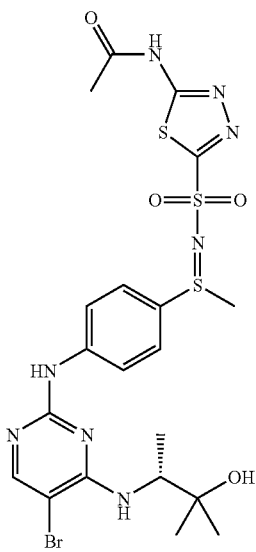

Preparation of the Final Product 250 mg (0.63 mmol) of (R)-3-[{5-bromo-2-(4-methylsulphanylphenylamino) pyrimidin-4-yl)}amino]-2-methylbutan-2-ol (compound 9.1), 210 mg (0.94 mmol) of N-(5-sulphamoyl[1,3,4]thiadiazol-2-yl)acetamide, 221 mg (1.01 mmol) of iodosobenzene and 222 mg (0.63 mmol) of iron(III)acetylacetonate are weighed into a flask, and 6 ml of acetonitrile are added. The mixture is stirred at room temperature for 96 hours and then concentrated in a rotary evaporator. The remaining residue is purified by chromatography (dichloromethane/ethanol 8:2). 9 mg (0.02 mmol; yield: 2%) of the product are obtained.

$^1$H-NMR (DMSO): 12.84 (s, 1H), 9.81 (s, 1H), 8.15 (s, 1H), 7.97 (m, 2H), 7.77 (m, 2H), 6.17 (d, 1H), 4.05 (m, 1H), 3.12 (s, 3H), 2.20 (s, 3H), 1.11 (m, 9H).

Example 20

(RS)—S-{4-[(5-Bromo-4-{[(R)-2-hydroxy-1,2-dimethylpropyl]amino}pyrimidin-2-yl)amino]phenyl}-N-(ethylsulphonyl)-S-methylsulphimide

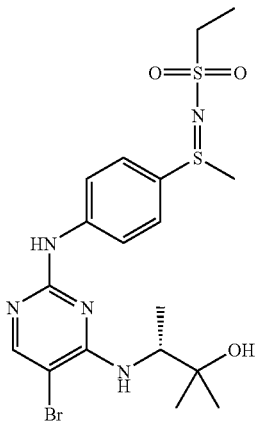

Preparation of the Final Product 250 mg (0.63 mmol) of (R)-3-[{5-bromo-2-(4-methylsulphanylphenylamino) pyrimidin-4-yl)}amino]-2-methylbutan-2-ol (compound 9.1), 103 mg (0.94 mmol) of ethylsulphonamide, 221 mg (1.01 mmol) of iodosobenzene and 222 mg (0.63 mmol) of iron(III)acetylacetonate are weighed into a flask, and 6 ml of acetonitrile are added. The mixture is stirred at room temperature for 130 hours and then concentrated in a rotary evaporator. The remaining residue is purified by chromatography (dichloromethane/ethanol 8:2). 24 mg (0.05 mmol; yield: 8%) of the product are obtained.

$^1$H-NMR (DMSO): 9.74 (s, 1H), 8.13 (s, 1H), 7.97 (m, 2H), 7.77 (m, 2H), 6.13 (d, 1H), 4.85 (br, 1H), 4.09 (m, 1H), 3.00 (s, 3H), 2.82 (q, 2H), 1.11 (m, 12H).

Example 21

(RS)—S-{4-[(5-Bromo-4-{[(R)-2-hydroxy-1,2-dimethylpropyl]amino}pyrimidin-2-yl)amino]phenyl}-S-methyl-N-(propylsulphonyl)sulphimide

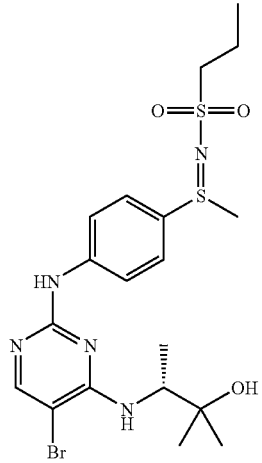

Preparation of the Final Product 250 mg (0.63 mmol) of (R)-3-[{5-bromo-2-(4-methylsulphanylphenylamino) pyrimidin-4-yl)}amino]-2-methylbutan-2-ol (compound 9.1), 116 mg (0.94 mmol) of 1-propylsulphonamide, 221 mg (1.01 mmol) of iodosobenzene and 222 mg (0.63 mmol) of iron(III)acetylacetonate are weighed into a flask, and 6 ml of acetonitrile are added. The mixture is stirred at room temperature for 250 hours and then concentrated in a rotary evaporator. The remaining residue is purified by chromatography (dichloromethane/ethanol 8:2). 55 mg (0.11 mmol; yield: 17%) of the product are obtained.

$^1$H-NMR (DMSO): 9.85 (s, 1H), 8.12 (s, 1H), 7.91 (m, 2H), 7.75 (m, 2H), 6.27 (d, 1H), 4.04 (m, 1H), 2.95 (s, 3H), 2.75 (m, 2H), 1.56 (m, 2H), 1.11 (m, 9H), 0.85 (tr, 3H).

Example 22

(RS)—S-{4-[(5-Bromo-4-{[(R)-2-hydroxy-1,2-dimethylpropyl]amino}pyrimidin-2-yl)amino]phenyl}-N-(tert-butylsulphonyl)-S-methylsulphimide

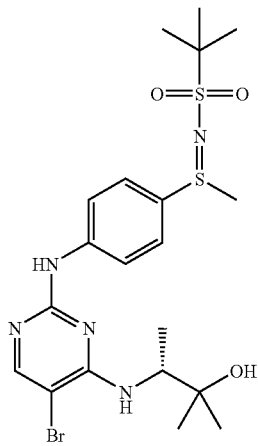

Preparation of the Final Product 250 mg (0.63 mmol) of (R)-3-[{5-bromo-2-(4-methylsulphanylphenylamino) pyrimidin-4-yl)}amino]-2-methylbutan-2-ol (compound 9.1), 129 mg (0.94 mmol) of tert-butylsulphonamide, 221 mg (1.01 mmol) of iodosobenzene and 222 mg (0.63 mmol) of iron(III)acetylacetonate are weighed into a flask, and 6 ml of acetonitrile are added. The mixture is stirred at room temperature for 250 hours and then concentrated in a rotary evaporator. The remaining residue is purified by chromatography (dichloromethane/ethanol 8:2). 15 mg (0.03 mmol; yield: 4%) of the product are obtained.

$^1$H-NMR (DMSO): 9.74 (s, 1H), 8.09 (s, 1H), 7.92 (m, 2H), 7.74 (m, 2H), 6.11 (d, 1H), 4.04 (m, 1H), 2.94 (s, 3H), 1.11 (m, 18H).

Process Variant 2

Examples 23 to 34

Example 23

(RS)—S-{4-[(4-{[2-(Acetylamino)ethyl]amino}-5-bromopyrimidin-2-yl)amino]-phenyl}-S-methyl-N-(tolylsulphonyl)sulphimide

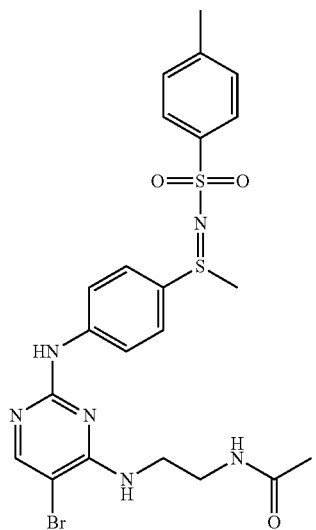

23a) Preparation of the Intermediates

Compound 23.1

N-[2-(5-Bromo-2-chloropyrimidin-4-ylamino)ethyl]acetamide

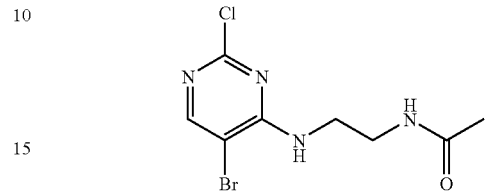

0.14 ml (1.42 mmol) of N-(2-aminoethyl)acetamide and 0.22 ml (1.60 mmol) of triethylamine are added to a solution of 300 mg (1.32 mmol) of 5-bromo-2,4-dichloro-pyrimidine in 4.2 ml of acetonitrile at room temperature. The mixture is stirred at room temperature for 24 hours and then diluted with ethyl acetate. It is washed with saturated NaCl solution, 10% strength citric acid solution and saturated NaHCO$_3$ solution. The organic phase is dried (Na$_2$SO$_4$), filtered and concentrated. The resulting residue is recrystallized from ethyl acetate. 294 mg (1.00 mmol; yield: 75%) of the product are obtained.

$^1$H-NMR (DMSO): 8.21 (s, 1H), 7.98 (tr, 1H), 7.74 (tr, 1H), 3.37 (m, 2H), 3.20 (m, 2H), 1.76 (s, 3H).

Compound 23.2

(RS)—S-Methyl-S-(4-nitrophenyl)-N-tosylsulphimide

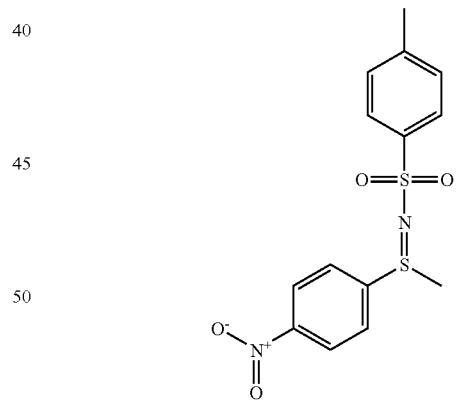

10.0 g (35.3 mmol) of chloramine-T trihydrate (Aldrich) are added to 5.0 g (29.6 mmol) of 1-methylsulphanyl-4-nitrobenzene in 120 ml of acetonitrile at room temperature. The mixture is stirred at room temperature for 4 hours and then diluted with ethyl acetate. The mixture is filtered with suction and the filter cake is washed with ethyl acetate. The combined organic phases are dried (Na$_2$SO$_4$), filtered and concentrated. The resulting residue is recrystallized from methanol. 2.2 g (6.5 mmol; yield: 22%) of the product are obtained.

$^1$H-NMR (DMSO):. 8.39 (m, 2H), 8.03 (m, 2H), 7.57 (m, 2H), 7.21 (m, 2H), 3.01 (s, 3H), 2.27 (s, 3H).

MS: 338 (EI).

Compound 23.3

(RS)—S-(4-Aminophenyl)-S-methyl-N-tosylsulphimide

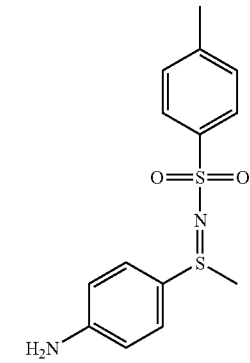

A solution of 500 mg (1.48 mmol) of (RS)—S-methyl-S-(4-nitrophenyl)-N-tosylsulphimide in 60 ml of ethanol is mixed with 500 mg of Raney nickel (50%, water-moist) and hydrogenated under an atmosphere of hydrogen at atmospheric pressure and room temperature for 2 hours. The hydrogen uptake amounts to 110 ml. The mixture is filtered and concentrated. The resulting residue is purified by chromatography (dichloromethane/ethanol 9:1). 124 mg (0.40 mmol; yield: 27%) of the product are obtained.

$^1$H-NMR (DMSO): 7.49 (m, 2H), 7.33 (m, 2H), 7.19 (m, 2H), 6.57 (m, 2H), 5.94 (s, 2H), 2.78 (s, 3H), 2.29 (s, 3H).

MS: 309 (ES).

23b) Preparation of the Final Product

A mixture of 65 mg (0.22 mmol) of N-[2-(5-bromo-2-chloropyrimidin-4-ylamino)-ethyl]acetamide and 62 mg (0.20 mmol) of (RS)—S-(4-aminophenyl)-S-methyl-N-tosylsulphimide in 3 ml of isopropanol is mixed with 0.005 ml of a 4 molar solution of hydrogen chloride in dioxane and stirred at 70° C. for 18 hours. The mixture is mixed with a further 0.005 ml of the 4 molar solution of hydrogen chloride in dioxane and stirred at 70° C. for a further 72 hours. The mixture is concentrated in a rotary evaporator, and the resulting residue is purified by chromatography (dichloro-methane/ethanol 8:2). 28 mg (0.05 mmol; yield: 25%) of the product are obtained.

$^1$H-NMR (DMSO): 9.64 (s, 1H), 8.08 (s, 1H), 7.88 (m, 2H), 7.59 (m, 2H), 7.51 (m, 2H), 7.19 (m, 2H), 6.58 (d, 1H), 4.30 (m, 1H), 2.87 (s, 3H), 2.28 (s, 3H), 1.22 (d, 6H).

MS: 522 (ES+).

Examples 24 to 32

A) Preparation of Intermediates

Compound 24.1

(RS)—S-Methyl-S-(4-nitrophenyl)-N-[(5-methyl-2-pyridyl)sulphonyl]sulphimide

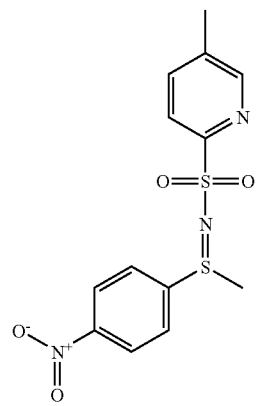

879 mg (2.73 mmol) of iodosobenzene diacetate are added to a suspension of 300 mg (1.77 mmol) of 1-methylsulphanyl-4-nitrobenzene, 610 mg (3.55 mmol) of 5-methyl-2-pyridine-sulphonamide, 285 mg (7.10 mmol) of magnesium oxide and 78 mg (0.18 mmol) of rhodium(II) acetate dimer in 12 ml of dichloromethane at room temperature. The mixture is stirred for 24 h and then concentrated. The resulting residue is purified by chromatography (dichloromethane/ethanol 95:5). 326 mg (0.96 mmol; yield: 54%) of the product are obtained.

$^1$H-NMR (DMSO): 8.41 (m, 2H), 8.31 (m, 1H), 8.12 (m, 2H), 7.76 (m, 1H), 7.70 (m, 1H), 3.11 (s, 3H), 2.29 (s, 3H).

MS: 340 (ES+).

Compound 24.2

(RS)—S-Methyl-S-(4-nitrophenyl)-N-[(4-chloro-3-pyridyl)sulphonyl]sulphimide

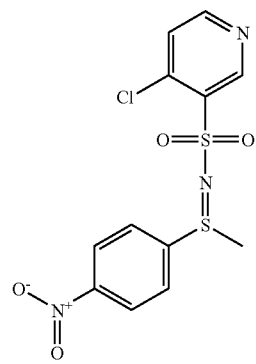

879 mg (2.73 mmol) of iodosobenzene diacetate are added to a suspension of 300 mg (1.77 mmol) of 1-methylsulphanyl-4-nitrobenzene, 683 mg (3.55 mmol) of 5-chloro-3-pyridine-sulphonamide, 285 mg (7.10 mmol) of magnesium oxide and 78 mg (0.18 mmol) of rhodium(II) acetate dimer in 12 ml of dichloromethane at room temperature. The mixture is stirred for 24 h and then concentrated. The resulting residue is purified by chromatography (dichloromethane/ethanol 95:5). 294 mg (0.82 mmol; yield: 46%) of the product are obtained.

¹H-NMR (DMSO): 8.94 (s, 1H), 8.61 (m, 1H), 8.39 (m, 2H), 8.11 (m, 2H), 7.64 (m, 1H), 3.12 (s, 3H).

MS: 360 (ES+).

Compound 24.3

(RS)—S-Methyl-S-(4-nitrophenyl)-N-[(4-nitrophenyl)sulphonyl]sulphimide

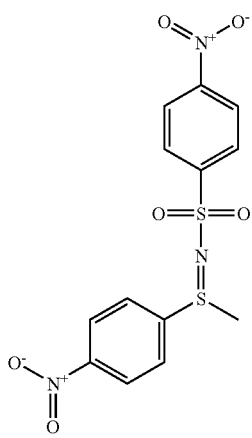

879 mg (2.73 mmol) of iodosobenzene diacetate are added to a suspension of 300 mg (1.77 mmol) of 1-methylsulphanyl-4-nitrobenzene, 716 mg (3.55 mmol) of 4-nitrobenzenesulphonamide, 285 mg (7.10 mmol) of magnesium oxide and 78 mg (0.18 mmol) of rhodium(II) acetate dimer in 12 ml of dichloromethane at room temperature. The mixture is stirred for 24 h and then concentrated. The resulting residue is purified by chromatography (dichloromethane/ethanol 95:5). 484 mg (1.31 mmol; yield: 74%) of the product are obtained.

¹H-NMR (DMSO): 8.37 (m, 2H), 8.25 (m, 2H), 8.06 (m, 2H), 7.93 (m, 2H), 3.09 (s, 3H).

MS: 370 (ES+).

Compound 24.4

(RS)—S-(4-Nitrophenyl)-S-methyl-N-mesylsulphimide

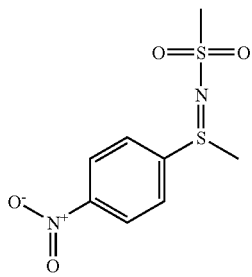

879 mg (2.73 mmol) of iodosobenzene diacetate are added to a suspension of 300 mg (1.77 mmol) of 1-methylsulphanyl-4-nitrobenzene, 337 mg (3.55 mmol) of methanesulphonamide, 285 mg (7.10 mmol) of magnesium oxide and 78 mg (0.18 mmol) of rhodium(II) acetate dimer in 12 ml of dichloromethane at room temperature. The mixture is stirred for 24 h and then concentrated. The resulting residue is purified by chromatography (dichloromethane/ethanol 95:5). 133 mg (0.51 mmol; yield: 29%) of the product are obtained.

¹H-NMR (DMSO): 8.43 (m, 2H), 8.14 (m, 2H), 3.06 (s, 3H), 2.86 (s, 3H).

MS: 263 (ES+).

Compound 24.5

(RS)—S-Methyl-S-(4-nitrophenyl)-N-[(4-methoxyphenyl)sulphonyl]sulphimide

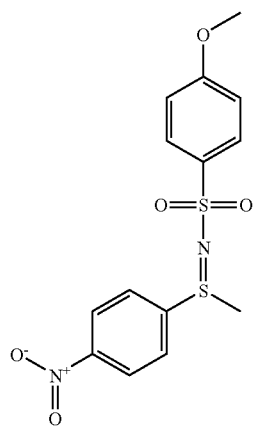

879 mg (2.73 mmol) of iodosobenzene diacetate are added to a suspension of 300 mg (1.77 mmol) of 1-methylsulphanyl-4-nitrobenzene, 663 mg (3.55 mmol) of 4-methoxybenzenesulphonamide, 285 mg (7.10 mmol) of magnesium oxide and 78 mg (0.18 mmol) of rhodium(II) acetate dimer in 12 ml of dichloromethane at room temperature. The mixture is stirred for 24 h and then concentrated. The resulting residue is purified by chromatography (dichloromethane/ethanol 95:5). 119 mg (0.34 mmol; yield: 19%) of the product are obtained.

¹H-NMR (DMSO): 8.36 (m, 2H), 8.04 (m, 2H), 7.61 (m, 2H), 6.94 (m, 2H), 3.74 (s, 3H), 3.01 (s, 3H).

MS: 355 (ES+).

B) Preparation of the Final Products

In analogy to Example 23 it is possible to prepare from the intermediates 24.1-24.5 for example the following final products:

| Example | Structure |
|---|---|
| 24 (identical to Example 11) | (structure) |
| 25 | (structure) |
| 26 | (structure) |
| 27 (identical to Example 12) | (structure) |
| 28 | (structure) |
| 29 | (structure) |

| Example | Structure |
|---------|-----------|
| 30 | 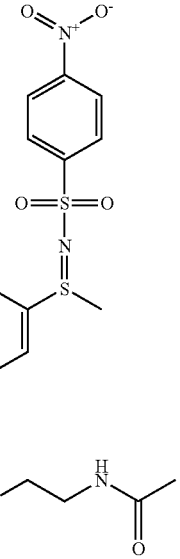 |
| 31 | 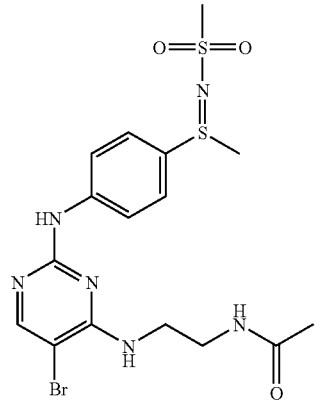 |
| 32 | 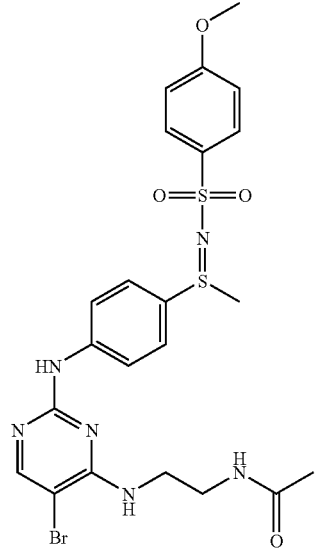 |

Example 33

Identical to Example 14

(RS)—S-{4-[(5-Bromo-4-{[(R)-2-hydroxy-1,2-dimethylpropyl]amino}pyrimidin-2-yl)amino]phenyl}-S-methyl-N-[(trifluoromethyl)sulphonyl]sulphimide

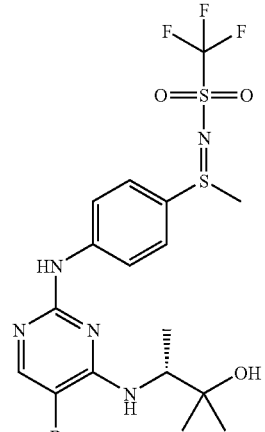

33a) Preparation of the Intermediates

Compound 33.1 (RS)—S-Methyl-S-{4-[(trifluoroacetyl)amino]phenyl}-N-[(trifluoromethyl)sulphonyl]sulphimide

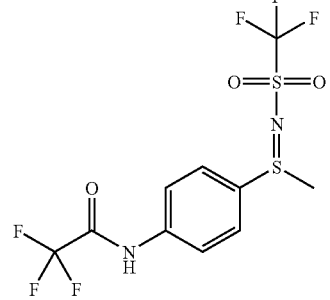

2.44 g (10.4 mmol) of 2,2,2-trifluoro-N-(4-methylsulphanylphenyl)acetamide and 2.80 g (18.8 mmol) of trifluoromethylsulphonamide are mixed with 145 ml of dichloromethane. 2.09 g (51.9 mmol) of magnesium oxide, 460 mg (1.04 mmol) of rhodium(II) acetate dimer and 6.68 g (20.75 mmol) of iodobenzene diacetate are added to the mixture. The mixture is stirred at room temperature for 1 hour and then filtered, and the filter cake is washed with dichloromethane. On concentration of the filtrate, crystals separate out and are filtered off with suction and washed with a little dichloromethane. Drying results in 3.60 g (9.42 mmol; yield: 91%) of the product.

$^1$H-NMR (DMSO): 11.65 (br, 1H), 7.93 (m, 4H), 3.21 (s, 3H).

Compound 33.2 (RS)—S-(4-Aminophenyl)-S-methyl-N-[(trifluoromethyl)-sulphonyl]sulphimide

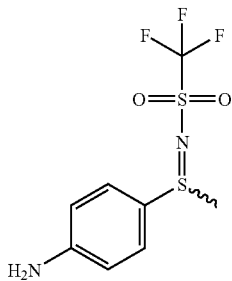

A solution of 1000 mg (2.62 mmol) of (RS)—S-methyl-S-{4-[(trifluoroacetyl)amino]-phenyl}-N-[(trifluoromethyl)sulphonyl]sulphimide in 25 ml of methanol is mixed with 361 mg (2.62 mmol) of potassium carbonate and stirred at room temperature for 23 hours. A further 360 mg (2.62 mmol) of potassium carbonate are added, and the mixture is stirred at room temperature for a further 22 hours. The mixture is diluted with water and extracted with ethyl acetate (twice). The combined organic phases are washed with saturated NaCl solution, filtered through a Whatman filter and concentrated. The resulting residue is purified by chromatography (hexane/ethyl acetate 1:4). 193 mg (0.67 mmol; yield: 26%) of the product are obtained.

$^1$H-NMR (DMSO): 7.52 (m, 2H), 6.66 (m, 2H), 6.18 (s, 2H), 3.08 (s, 3H).

33b) Preparation of the Final Product 50 mg (0.17 mmol) of (RS)—S-(4-aminophenyl)-S-methyl-N-[(trifluoromethyl)-sulphonyl]sulphimide and 51 mg (0.17 mmol) of (R)-3-[(5-bromo-2-chloropyrimidin-4-yl)amino]-2-methylbutan-2-ol (cf. WO2005037800) are stirred in 2 ml of 1-butanol at 90° C. for 74 hours and then concentrated in a rotary evaporator. The remaining residue is purified by chromatography (dichloromethane/ethanol 8:2). 6 mg (0.01 mmol; yield: 6%) of the product are obtained.

Example 34

(RS)—S-(4-{[4-{[(1R,2R)-2-Hydroxy-1-methylpropyl]amino}-5-(trifluoromethyl)-pyrimidin-2-yl]amino}phenyl)-S-methyl-N-[(trifluoromethyl)sulphonyl]-sulphimide

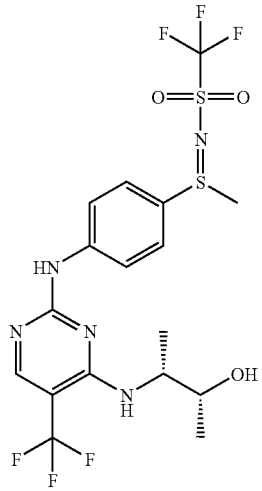

34a) Preparation of the Intermediates

Compound 34.1

(2R,3R)-3-(2-Chloro-5-trifluoromethylpyrimidin-4-ylamino)butan-2-ol

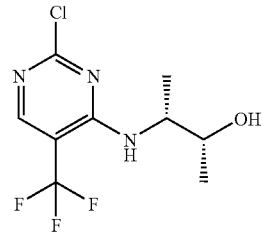

4.8 ml (34.8 mmol) of triethylamine are added dropwise to 3.78 g (17.4 mmol) of 2,4-dichloro-5-trifluoromethylpyrimidine and 2.19 g (17.4 mmol) of (2R,3R)-3-amino-butan-2-ol hydrochloride in 70 ml of acetonitrile at 0° C. The mixture is slowly warmed to room temperature and then stirred for 48 hours. The mixture is added to half-concentrated NaCl solution and extracted with ethyl acetate. The combined organic phases are dried (Na$_2$SO$_4$), filtered and concentrated. The resulting residue is purified by HPLC. 1.45 g (5.4 mmol; 31% yield) of the product are obtained.

Column: XBridge C18 5µ
Length×ID: 100×30 mm
Eluents: A:H$_2$O B:Acetonitrile
Buffer: A/0.1% TFA
Gradient: 60% A+40% B(2')_40->70% B(10')->99% B(0.5')
Flow rate: 40.0 ml/min
Detection: DAD (210-500 nm) TAC; MS-ESI+(125-800 m/z) TIC
Temperature: Room temperature
RT in min: 5.0-6.0

34b) Preparation of the Final Product 50 mg (0.19 mmol) of (2R,3R)-3-(2-chloro-5-trifluoromethylpyrimidin-4-ylamino)-butan-2-ol and 53 mg (0.94 mmol) of (RS)—S-(4-aminophenyl)-S-methyl-N-[(trifluoromethyl)sulphonyl]sulphimide are stirred in 2 ml of 1-butanol at room temperature for 4 hours. The mixture is concentrated in a rotary evaporator, and the remaining residue is purified by chromatography (dichloromethane/ethanol 95:5). 40 mg (0.19 mmol; yield: 42%) of the product are obtained.

$^1$H-NMR (DMSO): 10.20 (s, 1H), 8.32 (s, 1H), 8.06 (m, 2H), 7.90 (m, 2H), 6.14 (d, 1H), 5.11 (br, 1H), 4.16 (m, 1H), 3.80 (m, 1H), 3.23 (s, 3H), 1.25 (d, 3H), 1.09 (d, 3H).

MS: 520 (ES+)

Assay 1

Aurora-C Kinase Assay

Recombinant Aurora-C protein was expressed in transiently transfected HEK293 cells and then purified. The kinase substrate used was the biotinylated peptide having the amino acid sequence biotin-FMRLRRLSTKYRT, which was purchased from Jerini AG in Berlin.

Aurora-C [5 nM in the test mixture, test volume 5 µl] was incubated in the presence of various concentrations of test substances (0 µM and 10 measurement points within the range 0.001-20 µM in duplicate) in assay buffer [25 mM HEPES pH 7.4, 0.5 mM MnCl$_2$, 0.1 mM Na ortho-vanadate, 2.0 mM dithiothreitol, 0.05% bovine serum albumin (BSA), 0.01% Triton X-100, 3 µM adenosine trisphosphate (ATP), 0.67 nCi/µl gamma-$^{33}$P-ATP, 2.0 µM substrate peptide biotin-FMRLRRLSTKYRT, 1.0% dimethyl sulphoxide] at 22° C. for 90 min. The reaction was stopped by adding 12.5 µl of an EDTA/detection solution [16 mM EDTA, 40 mM ATP, 0.08% Triton X-100, 4 mg/ml PVT streptavidin SPA beads (from Amersham)]. After incubation for 10 minutes, the SPA beads were pelleted by centrifugation at 1000×G for 10 minutes. Measurement took place in a PerkinElmer Topcount scintillation counter. The measured data were normalized to 0% inhibition (enzyme reaction without inhibitor) and 100% inhibition (enzyme reaction in the presence of 0.1 µM staurosporine (from Sigma)). The IC50 values were determined by means of a 4-parameter fit using the company's own software.

Assay 2

CDK1/CycB Kinase Assay

Recombinant CDK1- and CycB-GST fusion proteins, purified from baculovirus-infected insect cells (Sf9), were purchased from ProQinase GmbH, Freiburg. The histone IIIS used as kinase substrate can be purchased from Sigma. CDK1/CycB (200 ng/measurement point) was incubated in the presence of various concentrations of test substances (0 µM, and within the range 0.01-100 µM) in assay buffer [50 mM Tris/HCl pH 8.0, 10 mM MgCl$_2$, 0.1 mM Na ortho-vanadate, 1.0 mM dithiothreitol, 0.5 µM ATP, 10 µg/measurement point histone IIIS, 0.2 µCi/measurement point $^{33}$P-gamma-ATP, 0.05% NP40, 1.25% dimethyl sulphoxide] at 22° C. for 10 min. The reaction was stopped by adding EDTA solution (250 mM, pH 8.0, 15 µl/measurement point).

15 µl of each reaction mixture were loaded onto P30 filter strips (from Wallac), and non-incorporated $^{33}$P-ATP was removed by washing the filter strips three times in 0.5% strength phosphoric acid for 10 min each time. After the filter strips had been dried at 70° C. for 1 hour, the filter strips were covered with scintillator strips (MeltiLex™ A, from Wallac) and baked at 90° C. for 1 hour. The amount of incorporated $^{33}$P (substrate phosphorylation) was determined by scintillation measurement in a gamma radiation counter (Wallac).

Assay 3

CDK2/CycE Kinase Assay

Recombinant CDK2- and CycE-GST fusion proteins, purified from baculovirus-infected insect cells (Sf9), were purchased from ProQinase GmbH, Freiburg. The histone IIIS used as kinase substrate was purchased from Sigma.

CDK2/CycE (50 ng/measurement point) was incubated in the presence of various concentrations of test substances (0 µM, and within the range 0.01-100 µM) in assay buffer [50 mM Tris/HCl pH 8.0, 10 mM MgCl$_2$, 0.1 mM Na ortho-vanadate, 1.0 mM dithiothreitol, 0.5 µM ATP, 10 µg/measurement point histone IIIS, 0.2 µCi/measurement point $^{33}$P-gamma-ATP, 0.05% NP40, 1.25% dimethyl sulphoxide] at 22° C. for 10 min. The reaction was stopped by adding EDTA solution (250 mM, pH 8.0, 15 µl/measurement point).

15 µl of each reaction mixture were loaded onto P30 filter strips (from Wallac), and non-incorporated $^{33}$P-ATP was removed by washing the filter strips three times in 0.5% strength phosphoric acid for 10 min each time.

After the filter strips had been dried at 70° C. for 1 hour, the filter strips were covered with scintillator strips (MeltiLex™ A, from Wallac) and baked at 90° C. for 1 hour. The amount of incorporated $^{33}$P (substrate phosphorylation) was determined by scintillation measurement in a gamma radiation counter (Wallac).

Assay 4

KDR Kinase Assay

Recombinant KDR protein was expressed in *E. coli* and then purified. The kinase substrate used was the biotinylated peptide having the amino acid sequence biotin-DF-GLARDMYDKEYYSVG, which was purchased from Biosynthan. KDR [test volume 5 µl] was incubated in the presence of various concentrations of test substances (0 µM, and 10 measurement points within the range 0.001-20 µM in duplicate) in assay buffer [50 mM HEPES pH 7.0, 25.0 mM MgCl$_2$, 1.0 mM MgCl$_2$, 0.1 mM Na ortho-vanadate, 1.0 mM dithiothreitol, 0.001% NP40, 10 µM ATP, 0.03 µM substrate peptide biotin-poly GluTyr, 1.0% dimethyl sulphoxide] at 22° C. for 45 min. The reaction was stopped by adding 5 µl of an EDTA/detection solution [50 mM HEPES pH 7.5, 125 mM EDTA, 0.2% BSA, 0.1 µM streptavidin-XLent (from Cis-Bio), 2 nM PT66-Eu (from PerkinElmer)]. The fluorescence emission at 620 nm and 665 nm after excitation with light of the wavelength 350 nm was measured in a Rubystar HTRF instrument from BMG Labsystems.

The measured data (ratio of emission 665 divided by emission 620 multiplied by 10 000) were normalized to 0% inhibition (enzyme reaction without inhibitor) and 100% inhibition (all assay components apart from enzyme). The IC50 values were determined by means of a 4-parameter fit using the company's own software.

Assay 5

MCF7 Proliferation Assay

Cultivated human MCF7 breast tumour cells (ATCC HTB-22) were plated out in a density of 5000 cells/measurement point in 200 µl of growth medium (RPMI1640, 10% foetal calf serum, 2 mU/mL insulin, 0.1 nM oestradiol) in a 96-well multititre plate. After 24 hours, the cells from a plate (zero plate) were stained with crystal violet (see below), while the medium in the other plates was replaced by fresh culture medium (200 µl) to which the test substances had been added in various concentrations (0 µM, and in the range 0.1-30 µM; the final concentration of the solvent dimethyl sulphoxide was 0.5%). The cells were incubated in the presence of the test substances for 4 days. The cell proliferation was determined by staining the cells with crystal violet: the cells were fixed by adding 20 µl/measurement point of an 11% strength glutaraldehyde solution at room temperature for 15 min. After the fixed cells had been washed three times with water, the plates were dried at room temperature. The cells were stained by adding 100 µl/measurement point of a 0.1% strength crystal violet solution (pH adjusted to pH 3 by adding acetic acid). After the stained cells had been washed three times with water, the plates were dried at room temperature. The dye was dissolved by adding 100 µl/measurement point of a 10% strength acetic acid solution, and the extinction was determined by photometry at a wavelength of 595 nm. The percentage change in cell growth was calculated by normalizing the measurements to the extinctions of the zero point plate (=0%) and the extinction of the untreated (0 µM) cells (=100%). The IC50 values were determined by means of a 4-parameter fit using the company's own software.

Example 35

The compounds of Examples 1 to 9 and 11-23 were tested in the various kinase assays for their inhibitory effect (Tab. 1)

TABLE 1

| Ex. | Aurora C IC50 [nM] | CDK1/CycB IC50 [nM] | CDK2/CycE IC50 [nM] | KDR (VEGFR2) IC50 [nM] |
|---|---|---|---|---|
| 1 | 240 | >1000 | 900 | 37 |
| 2 |  | >1000 | >1000 | 200 |
| 3 | 90 | >1000 | 1000 | 13 |
| 4 |  | >1000 | >1000 | 170 |
| 5 | 4600 | >1000 | >1000 | 760 |
| 6 |  | >1000 | >1000 | 120 |
| 7 | 680 | >1000 | >1000 | 43 |
| 8 | 360 | 620 | 99 | 22 |
| 9 | 360 | 150 | 28 | 36 |
| 11 | 370 | 90 | 14 | 44 |
| 12 | 480 | 160 | 39 | 38 |
| 13 | 660 | 140 | 28 | 15 |
| 14 | 990 | 120 | 39 | 70 |
| 15 | 570 | 110 | 21 | 37 |
| 16 | 1800 | 260 | 72 | 150 |
| 17 | nd | nd | nd | nd |
| 18 | 400 | 50 | 6 | 35 |
| 19 | 1100 | 98 | 25 | 320 |
| 20 | 250 | 31 | 10 | 35 |
| 21 | 390 | 36 | 12 | 49 |
| 22 | 390 | 46 | 22 | 44 |
| 23 | 36 | 990 | 1000 | 35 |

It is possible to prepare from the structural class of sulphimide-substituted aminopyrimidines both selective and multi-target kinase inhibitors. Ex. 7 represents a selective inhibitor of the VEGF-R2 tyrosine kinase, whereas Ex. 8 also inhibits Aurora C kinase besides VEGF-R2, Ex. 3 inhibits VEGF-R2 and Aurora C, and Ex. 11 is active on the serine/threonine kinases Aurora C and CDK2 besides VEGF-R2. Ex. 9 shows inhibition of the VEGF-R2 and CDK2 kinase.

Example 36

Some compounds of the examples were tested for their antiproliferative effect in the MCF7 proliferation assay (Tab. 2). The tested compounds showed a potent inhibition of the proliferation of MCF7 human breast tumour cells at micromolar and submicro-molar concentration. In particular, Examples Nos 9, 10, 13, 14, 15, 16, and 17 showed excellent antiproliferative activity.

TABLE 2

| Ex. | MCF7 IC50 [µM] |
|---|---|
| 1 | 2.2 |
| 2 | — |
| 3 | 0.34 |
| 4 | — |
| 5 | — |
| 6 | — |
| 7 | — |
| 8 | 0.9 |
| 9 | <0.1 |
| 11 | <0.1 |
| 12 | 0.2 |
| 13 | 0.11 |
| 14 | 0.11 |
| 15 | 0.11 |
| 16 | 0.17 |
| 17 | — |
| 18 | 0.17 |
| 19 | 1.8 |
| 20 | 0.35 |
| 21 | 0.31 |
| 22 | 0.33 |
| 23 | 2.2 |

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102006027156, filed Jun. 8, 2006, and U.S. Provisional Application Ser. No. 60/814,525, filed Jun. 19, 2006, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula I,

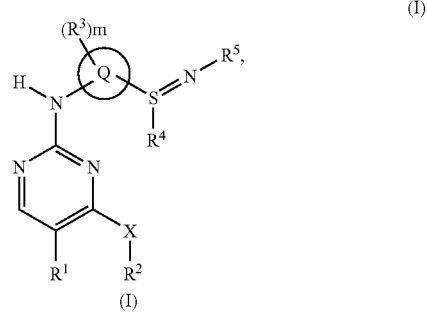

(I)

in which
R$^1$ is
(i) hydrogen, halogen, cyano, nitro, —NR$^8$R$^9$, —NR$^7$—C(O)—R$^{12}$, —NR$^7$—C(O)—OR$^{12}$, —NR$^7$—C(O)—NR$^8$R$^9$, —NR$^7$—SO$_2$—R$^{12}$, —CF$_3$ or —OCF$_3$, or
(ii) a C$_1$-C$_6$-alkyl, C$_2$-C$_6$-alkenyl, C$_1$-C$_6$-alkoxy or C$_2$-C$_6$-alkynyl radical which is optionally substituted one or more times, identically or differently, by hydroxy, —NR$^8$R$^9$, —NR$^7$—C(O)—R$^{12}$, —NR$^7$—

$C(O)$—$OR^{12}$, —$NR^7$—$C(O)$—$NR^8R^9$, —$NR^7$—$SO_2$—$R^{12}$, cyano, halogen, $C_1$-$C_6$-alkoxy, —$CF_3$ and/or —$OCF_3$, or (iii) a phenyl or monocyclic heteroaryl ring which is optionally substituted one or more times, identically or differently, by hydroxy, —$NR^8R^9$, —$NR^7$—$C(O)$—$R^{12}$, —$NR^7$—$C(O)$—$OR^{12}$, —$NR^7$—$C(O)$—$NR^8R^9$, —$NR^7$—$SO_2$—$R^{12}$, cyano, halogen, —$CF_3$, $C_1$-$C_6$-alkoxy, —$OCF_3$ and/or $C_1$-$C_6$-alkyl, $R^2$ is (i) hydrogen or (ii) a $C_1$-$C_{10}$-alkyl, $C_2$-$C_{10}$-alkenyl or $C_2$-$C_{10}$-alkynyl radical, a $C_3$-$C_7$-cycloalkyl, phenyl or naphthyl ring, a heterocyclyl ring having 3 to 8 ring atoms or a mono- or bicyclic heteroaryl ring, in each case optionally substituted one or more times, identically or differently, by a) halogen, hydroxy, —$NR^8R^9$, —$NR^7$—$C(O)$—$R^{12}$, —$NR^7$—$C(O)$—$OR^{12}$, —$NR^7$—$C(O)$—$NR^8R^9$, —$NR^7$—$SO_2$—$R^{12}$, cyano, —$C(O)R^6$, —$O(CO)$—$R^{12}$, —$SO_2NR^8R^9$, —$SO_2$—$R^{12}$, —$S(O)(NR^8)R^{12}$, —$(N)S(O)R^{13}R^{14}$, —$CF_3$, —$OCF_3$, —$N[(CO)$—$(C_1$-$C_6$-alkyl)]_2$ and/or b) $C_1$-$C_6$-alkoxy, $C_1$-$C_6$-alkyl, $C_2$-$C_6$-alkenyl, $C_2$-$C_6$-alkynyl, $C_3$-$C_8$-cycloalkyl, phenyl, naphthyl, heterocyclyl having 3 to 8 ring atoms and/or a monocyclic or bicyclic heteroaryl, in each case optionally themselves substituted one or more times, identically or differently, by halogen, hydroxy, a $C_1$-$C_6$-alkyl, $C_1$-$C_6$-alkoxy, —$NR^8R^9$, —$C(O)OR^{16}$, —$SO_2NR^8R^9$, —$CF_3$ or —$OCF_3$, $R^3$ is (i) hydroxy, halogen, cyano, nitro, —$CF_3$, —$OCF_3$, —$C(O)NR^8R^9$, —$C(S)NR^8R^9$, —$NR^8R^9$, —$NR^7$—$C(O)$—$R^{12}$, —$NR^7$—$C(O)$—$OR^{12}$, —$NR^7$—$C(O)$—$NR^8R^9$, —$NR^7$—$SO_2$—$R^{12}$, and/or (ii) a $C_1$-$C_6$-alkyl and/or $C_1$-$C_6$-alkoxy radical which is optionally substituted one or more times, identically or differently, by halogen, hydroxy, $C_1$-$C_6$-alkoxy, —$CF_3$, —$OCF_3$ or —$NR^8R^9$, and/or (iii) a $C_3$-$C_7$-cycloalkyl ring which is optionally substituted one or more times, identically or differently, by halogen, hydroxy, $C_1$-$C_6$-alkoxy, —$CF_3$, —$OCF_3$, —$NR^8R^9$ and/or $C_1$-$C_6$-alkyl, m is 0-4, $R^4$ is a $C_1$-$C_6$-alkyl, $C_2$-$C_6$-alkenyl, $C_2$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy, —$OCF_3$ and/or $C_1$-$C_6$-alkyl, or $R^3$ and $R^4$ together form a 5 to 7-membered ring which is fused to Q and which is optionally substituted one or more times, identically or differently, by hydroxy, $C_1$-$C_6$-alkyl, $C_1$-$C_6$-alkoxy, halogen or —$NR^8R^9$, and optionally comprises in addition to the double bond from Q a further double bond if the ring is 5-membered, $R^5$ is —$SO_2$—$(CH_2)_n$—$R^{12}$ where n is 0 or 1,
—$C(O)R^{12}$, —$C(O)OR^{12}$, —$C(O)NR^8R^9$, —$C(S)OR^{12}$, —$C(S)NR^8R^9$ or —$R^{12}$, or $R^4$ and $R^5$ together form a 5 to 7-membered ring of the formula

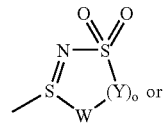 or 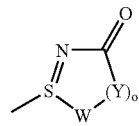

in which

W and Y are each independently of one another a —$CH_2$— group which is optionally substituted one or more times, identically or differently, by hydroxy, $C_1$-$C_6$-alkyl, $C_1$-$C_6$-alkoxy or —$NR^8R^9$, where the $C_1$-$C_6$-alkyl and/or $C_1$-$C_6$-alkoxy substituent is optionally itself substituted one or more times, identically or differently, by hydroxy, $C_1$-$C_6$-alkoxy or —$NR^8R^9$, and/or optionally comprises in addition to the imide double bond 1 or 2 further double bonds, and in which o is 1-3

X is —$O$—, —$S$— or —$NR^{15}$, where $R^{15}$ is (i) hydrogen or (ii) a $C_1$-$C_6$-alkyl radical, $C_3$-$C_8$-cycloalkyl or phenyl ring, a heterocyclyl ring having 3 to 8 ring atoms or a monocyclic heteroaryl ring, or (iii) —$C(O)$—$(C_1$-$C_6)$-alkyl, —$C(O)$-phenyl, or —$C(O)$-benzyl and (ii) and (iii) are optionally substituted one or more times, identically or differently, by hydroxy, —$NR^{10}R^{11}$, cyano, halogen, —$CF_3$, $C_1$-$C_6$-alkoxy and/or —$OCF_3$, or if X is —$NR^{15}$—, alternatively X, $R^{15}$ and $R^2$ together form a 3 to 8 membered ring which optionally comprises in addition to the nitrogen atom one or more further heteroatoms, is optionally substituted one or more times, identically or differently, by hydroxy, $C_1$-$C_6$-alkyl, $C_1$-$C_6$-alkoxy, —$C(O)R^{12}$, —$SO_2R^{12}$, halogen or the group —$NR^8R^9$, optionally comprises 1 to 3 double bonds, and/or is optionally interrupted by one or more —$C(O)$— groups, Q is a phenyl, naphthyl or a monocyclic or bicyclic heteroaryl ring, $R^6$ is (i) hydrogen or hydroxy, or (ii) a $C_1$-$C_6$-alkyl, $C_3$-$C_6$-alkenyl, $C_3$-$C_6$-alkynyl or $C_1$-$C_6$-alkoxy radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy and/or —$OCF_3$, $R^7$ is hydrogen or a $C_1$-$C_6$-alkyl radical, $R^8$ and $R^9$ are independently of one another (i) hydrogen and/or (ii) a $C_1$-$C_6$-alkyl radical, $C_2$-$C_6$-alkenyl, $C_3$-$C_8$-cycloalkyl and/or phenyl ring, a heterocyclyl ring having 3 to 8 ring atoms and/or a monocyclic heteroaryl ring, optionally substituted one or more times, identically or differently, by hydroxy, —$NR^{10}R^{11}$, cyano, halogen, —$CF_3$, $C_1$-$C_6$-alkoxy and/or —$OCF_3$, or $R^8$ and $R^9$ together with the nitrogen atom form a 5- to 7-membered ring which optionally comprises in addition to the nitrogen atom 1 or 2 further heteroatoms, and which may be substituted one or more times, identically or differently, by hydroxy, —$NR^{10}R^{11}$, cyano, halogen, —$CF_3$, $C_1$-$C_6$-alkoxy and/or —$OCF_3$, $R^{10}$ and $R^{11}$ are independently of one another hydrogen or a $C_1$-$C_6$-alkyl radical which is optionally substituted one or more times, identically or differently, by hydroxy, cyano, halogen, —$CF_3$, $C_1$-$C_6$-alkoxy and/or —$OCF_3$, $R^{12}$, $R^{13}$, $R^{14}$ are independently of one another —$CF_3$ or a $C_1$-$C_6$-alkyl, $C_2$-$C_6$-alkenyl and/or $C_2$-$C_6$-alkynyl radical, a $C_3$-$C_7$-cycloalkyl or phenyl ring, a heterocyclyl ring having 3 to 8 ring atoms or a monocyclic heteroaryl ring, which are optionally in each case themselves substituted one or more times, identically or differently, by hydroxy, nitro, —$NR^8R^9$, —NH—C(O)—$C_1$-$C_6$-alkyl, cyano, halogen, —$CF_3$, $C_1$-$C_6$-alkyl, $C_1$-$C_6$-alkoxy and/or —$OCF_3$, $R^{16}$ is (i) hydrogen or (ii) a $C_1$-$C_6$-alkyl, $C_3$-$C_6$-alkenyl, $C_3$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy and/or —$OCF_3$, or a salt, diastereomer or enantiomer thereof.

2. A compound of formula I according to claim 1, in which $R^1$ is halogen, —$CF_3$, —$OCF_3$, $C_1$-$C_4$-alkyl or nitro, $R^2$ is a $C_1$-$C_{10}$-alkyl, $C_2$-$C_{10}$-alkenyl or $C_2$-$C_{10}$-alkynyl radical, a $C_3$-$C_7$-cycloalkyl, phenyl or a mono- or bicyclic heteroaryl ring or a heterocyclyl ring having 3 to 7 ring atoms, in each case optionally substituted one or more times, identically or differently, by hydroxy, —$NR^8R^9$, —$NR^7$—C(O)—$R^{12}$ and/or a $C_1$-$C_4$-alkyl radical which is optionally itself substituted one or more times by hydroxy $R^3$ is (i) hydroxy, halogen, cyano, nitro, —$CF_3$, —$OCF_3$, —$NR^8R^9$, —$NR^7$—C(O)—$R^{12}$, —$NR^7$—C(O)—$OR^{12}$, —$NR^7$—C(O)—$NR^8R^9$, —$NR^7$—$SO_2$—$R^{12}$, and/or (ii) a $C_1$-$C_3$-alkyl and/or $C_1$-$C_3$-alkoxy radical which is optionally substituted one or more times, identically or differently, by halogen, hydroxy, $C_1$-$C_6$-alkoxy, —$CF_3$, —$OCF_3$ or —$NR^8R^9$, m is 0 or 1, $R^4$ is a $C_1$-$C_5$-alkyl radical, a $C_3$-$C_6$-cycloalkyl or a phenyl ring, in each case optionally themselves substituted one or more times, identically or differently, by hydroxy, —$NR^8R^9$, cyano, halogen, —$CF_3$, $C_1$-$C_6$-alkoxy, —$OCF_3$ and/or $C_1$-$C_6$-alkyl, or $R^3$ and $R^4$ together form a 5-membered ring which is fused to Q and which optionally comprises in addition to the double bond from Q a further double bond, $R^5$ is —$SO_2$—$(CH_2)_n$—$R^{12}$ where n is 0 or 1, where $R^{12}$ is $CF_3$ or is a $C_1$-$C_4$-alkyl radical, a $C_3$-$C_6$-cycloalkyl or phenyl ring or a heterocyclyl ring having 3 to 6 ring atoms or a monocyclic heteroaryl ring, optionally in each case themselves substituted one or more times, identically or differently, by hydroxy, nitro, —$NR^8R^9$, cyano, halogen, —$CF_3$, $C_1$-$C_6$-alkyl, $C_1$-$C_6$-alkoxy and/or —$OCF_3$, or $R^4$ and $R^5$ together form a 5-membered ring of the formula (1)

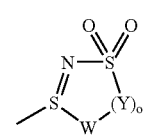

(1)

in which W and Y are each a —$CH_2$— group, and in which o is 1,

X is —O—, —S— or —$NR^{15}$—, where $R^{15}$ is (i) hydrogen or (ii) a $C_1$-$C_6$-alkyl radical, $C_3$-$C_8$-cycloalkyl or phenyl ring, a heterocyclyl ring having 3 to 8 ring atoms or a monocyclic heteroaryl ring, or (iii) —C(O)—$(C_1$-$C_6)$-alkyl, —C(O)-phenyl, or —C(O)-benzyl, and (ii) and (iii) are optionally substituted one or more times, identically or differently, by hydroxy, —$NR^{10}R^{11}$, cyano, halogen, —$CF_3$, $C_1$-$C_6$-alkoxy and/or —$OCF_3$, or if X is —$NR^{15}$—, alternatively X, $R^{15}$ and $R^2$ together form a 3 to 8 membered ring which optionally comprises in addition to the nitrogen atom one or more further heteroatoms, is optionally substituted one or more times, identically or differently, by hydroxy, $C_1$-$C_6$-alkyl, $C_1$-$C_6$-alkoxy, —$C(O)R^{12}$, —$SO_2R^{12}$, halogen or the group —$NR^8R^9$, optionally comprises 1 to 3 double bonds, and/or is optionally interrupted by one or more —C(O)— groups, Q is a phenyl, naphthyl or a monocyclic or bicyclic heteroaryl ring, $R^6$ is a $C_2$-$C_5$-alkyl, $C_4$-$C_6$-alkenyl, $C_4$-$C_6$-alkynyl or $C_2$-$C_5$-alkoxy radical, a $C_4$-$C_6$-cycloalkyl or phenyl ring, a heterocyclyl ring having 3 to 5 ring atoms or a monocyclic heteroaryl ring, in each case optionally themselves substituted one or more times, identically or differently, by hydroxy, —$NR^8R^9$, cyano, halogen, —$CF_3$, $C_1$-$C_6$-alkoxy and/or —$OCF_3$, $R^7$ is hydrogen or a $C_1$-$C_6$-alkyl radical, $R^8$ and $R^9$ are each independently of one another hydrogen and/or a $C_1$-$C_4$-alkyl radical, $C_3$-$C_6$-cycloalkyl and/or phenyl ring, and/or a monocyclic heteroaryl ring, in each case optionally substituted one or more times, identically or differently, by hydroxy, —$NR^{10}R^{11}$ or $C_1$-$C_6$-alkoxy, or $R^8$ and $R^9$ together with the nitrogen atom form a 5- to 7-membered ring which optionally comprises in addition to the nitrogen atom 1 further heteroatom, and which may be substituted one or more times by hydroxy, $R^{10}$ and $R^{11}$ are independently of one another hydrogen or a $C_1$-$C_6$-alkyl radical which is optionally substituted one or more times, identically or differently, by hydroxy, $R^{12}$ is $CF_3$ or is a $C_1$-$C_6$-alkyl, $C_2$-$C_6$-alkenyl or $C_2$-$C_6$-alkynyl radical, a $C_3$-$C_7$-cycloalkyl or phenyl ring, a heterocyclyl ring having 3 to 8 ring atoms or a monocyclic heteroaryl ring, in each case optionally themselves substituted one or more times, identically or differently, by hydroxy, halogen, nitro, —$NR^8R^9$, $C_1$-$C_6$-alkyl, and/or $C_1$-$C_6$-alkoxy, $R^{13}$ and $R^{14}$ are independently of one another a $C_1$-$C_6$-alkyl radical, and $R^{16}$ is a $C_1$-$C_6$-alkyl radical, a $C_3$-$C_7$-cycloalkyl or phenyl ring, a heterocyclyl ring having 3 to 8 ring atoms or a monocyclic heteroaryl ring, or a salt, diastereomer or enantiomer thereof.

3. A compound of formula (I) according to claim 1, in which

Q is a phenyl ring, or a salt, diastereomer or enantiomer thereof.

4. A compound of formula (I) according to claim 1, in which $R^1$ is bromine or $CF_3$, or a salt, diastereomer or enantiomer thereof.

5. A compound of formula (I) according to claim 1, in which $R^2$ is a $C_1$-$C_6$-alkyl radical, a $C_3$-$C_7$-cycloalkyl or phenyl ring, in each case optionally substituted one or more times, identically or differently, by hydroxy and/or —NH—C(O)—$C_1$-$C_6$-alkyl, or a salt, diastereomer or enantiomer thereof.

6. A compound of formula (I) according to claim 1, in which

X is —$NR^{15}$—, where $R^{15}$ is hydrogen, or a salt, diastereomer or enantiomer thereof.

7. A compound of formula (I) according to claim 1, in which $R^3$ is hydroxy, fluorine, chlorine, bromine, cyano, nitro, —$CF_3$, methyl or methoxy, or a salt, diastereomer or enantiomer thereof.

8. A compound of formula (I) according to claim 1, in which m is 0, or a salt, diastereomer or enantiomer thereof.

9. A compound of formula (I) according to claim 1, in which $R^4$ is a $C_1$-$C_4$-alkyl radical or a $C_3$-$C_5$-cycloalkyl ring, in each case optionally itself substituted one or more times, identically or differently, by hydroxy, —$NR^8R^9$ or halogen, or a salt, diastereomer or enantiomer thereof.

10. A compound of formula (I) according to claim 1, in which $R^5$ is —$SO_2R^{12}$, where $R^{12}$ is a $C_1$-$C_6$-alkyl radical, a phenyl or a monocyclic heteroaryl ring, optionally in each case themselves substituted one or more times, identically or differently, by nitro, halogen and/or $C_1$-$C_6$-alkyl, or a salt, diastereomer or enantiomer thereof.

11. A compound of formula (I) according to claim 1, in which $R^5$ is —$SO_2$—$(CH_2)_n$—$R^{12}$ where n is 0 or 1, where $R^{12}$ is —$CF_3$ or is a $C_1$-$C_6$-alkyl radical, a phenyl or a monocyclic heteroaryl ring, which are optionally in each case themselves substituted one or more times, identically or differently, by nitro, —NH—C(O)—$C_1$-$C_6$-alkyl, halogen, $C_1$-$C_6$-alkyl, $C_1$-$C_6$-alkoxy and/or —$OCF_3$, or a salt, diastereomer or enantiomer thereof.

12. A compound of formula (I) according to claim 1, in which $R^6$ is a $C_1$-$C_6$-alkyl, a $C_1$-$C_6$-alkoxy radical or a $C_3$-$C_7$-cycloalkyl ring, in each case optionally themselves substituted one or more times, identically or differently, by hydroxy, —$NR^8R^9$ and/or $C_1$-$C_6$-alkoxy, or a salt, diastereomer or enantiomer thereof.

13. A compound of Compounds of the general formula (I) according to claim 1, in which $R^7$ is hydrogen or a $C_1$-$C_6$-alkyl radical, or a salt, diastereomer or enantiomer thereof.

14. A compound of formula (I) according to claim 1, in which $R^8$ and $R^9$ are hydrogen and/or a $C_1$-$C_6$-alkyl radical, a $C_3$-$C_6$-cycloalkyl and/or phenyl ring, and/or a monocyclic heteroaryl ring, or $R^8$ and $R^9$ form together with the nitrogen atom a 5- or 6-membered ring which optionally comprises in addition to the nitrogen atom 1 further heteroatom, or a salt, diastereomer or enantiomer thereof.

15. A compound of formula (I) according to claim 1, in which $R^{10}$ and $R^{11}$ are independently of one another hydrogen or a methyl group, or a salt, diastereomer or enantiomer thereof.

16. A compound of formula (I) according to claim 1, in which $R^{12}$ is a $C_1$-$C_6$-alkyl radical, a phenyl or monocyclic heteroaryl ring, in each case optionally themselves substituted one or more times, identically or differently, by hydroxy, halogen, nitro or $C_1$-$C_6$-alkyl, or a salt, diastereomer or enantiomer thereof.

17. A compound of formula (I) according to claim 1, in which $R^{13}$ and $R^{14}$ are independently of one another a $C_1$-$C_6$-alkyl radical, or a salt, diastereomer or enantiomer thereof.

18. A compound of formula (I) according to claim 1, in which $R^{16}$ is a $C_1$-$C_6$-alkyl radical, or a salt, diastereomer or enantiomer thereof.

19. A compound according to formula (I) of claim 1, in which $R^1$ is hydrogen, halogen or —$CF_3$, $R^2$ is a $C_1$-$C_{10}$-alkyl radical, a $C_3$-$C_7$-cycloalkyl or phenyl ring, in each case optionally substituted one or more times, identically or differently, by hydroxy or —NH—C(O)—$C_1$-$C_6$-alkyl m is 0, $R^4$ is a $C_1$-$C_6$-alkyl radical, $R^5$ is —$SO_2$—$(CH_2)_n$—$R^{12}$ where n is 0 or 1, X is —NH—, Q is a phenyl ring, $R^{12}$ is —$CF_3$ or is a $C_1$-$C_6$-alkyl radical, a phenyl or a monocyclic heteroaryl ring, which are in each case optionally themselves substituted one or more times, identically or differently, by nitro, halogen, —$CF_3$, $C_1$-$C_6$-alkyl, —NH—C(O)—$C_1$-$C_6$-alkyl, $C_1$-$C_6$-alkoxy and/or —$OCF_3$, or a salt, diastereomer or enantiomer thereof.

20. A compound according to formula (I) of claim 1, in which $R^1$ is hydrogen or halogen, $R^2$ is a $C_1$-$C_{10}$-alkyl radical, a $C_3$-$C_7$-cycloalkyl or phenyl ring, in each case optionally substituted one or more times, identically or differently, by hydroxy, $C_1$-$C_6$-alkyl radical or —$NR^7$—C(O)—$R^{12}$, m is 0, $R^4$ is a $C_1$-$C_6$-alkyl radical, $R^5$ is —$SO_2R^{12}$, X is —$NR^{15}$—, where $R^{15}$ is hydrogen, Q is a phenyl ring, $R^{12}$ is a $C_1$-$C_6$-alkyl radical, a phenyl or a monocyclic heteroaryl ring, in each case optionally themselves substituted one or more times, identically or differently, by nitro, halogen or $C_1$-$C_6$-alkyl, or a salt, diastereomer or enantiomer thereof.

21. A process for preparing a compound according to claim 1, comprising a) reacting a 2-chloropyrimidine of formula (IV) with a nucleophiles of the formula (III) to give a compound of formula (II)

b) iminating of a thioethers of a formula (II) to obtain a compound of formula (I)

where Q, $R^1$, $R^2$, $R^3$, $R^4$, $R^5$, X and m have the meanings indicated in formula (I) according to claims 1.

22. A process for preparing a compounds of formula (I) according to claim 1, comprising reacting a 2 chloropyrimidine of formula (IV) with a nucleophiles of formula (VII)

where Q, $R^1$, $R^2$, $R^3$, $R^4$, $R^5$, X and m have the meanings indicated in the general formula (I) according to claim 1.

23. A method for the treatment of breast cancer, comprising administering to a host in need thereof an effective amount of a compound according to claim 1.

24. A pharmaceutical composition comprising a compound according to claim 1 and a pharmaceutically acceptable carrier.

* * * * *